(12) United States Patent
Basile

(10) Patent No.: US 9,878,012 B2
(45) Date of Patent: Jan. 30, 2018

(54) IL-12 FORMULATIONS FOR ENHANCING HEMATOPOIESIS

(75) Inventor: Lena A. Basile, Tujunga, CA (US)

(73) Assignee: Neumedicines, Inc., Pasadena, CA (US)

( * ) Notice: Subject to any disclaimer, the term of this patent is extended or adjusted under 35 U.S.C. 154(b) by 0 days.

(21) Appl. No.: 13/697,940

(22) PCT Filed: May 18, 2011

(86) PCT No.: PCT/US2011/036936
§ 371 (c)(1),
(2), (4) Date: Jan. 30, 2013

(87) PCT Pub. No.: WO2011/146574
PCT Pub. Date: Nov. 24, 2011

(65) Prior Publication Data
US 2013/0129674 A1 May 23, 2013

Related U.S. Application Data

(60) Provisional application No. 61/345,986, filed on May 18, 2010.

(51) Int. Cl.
| | | |
|---|---|---|
| A61K 38/00 | (2006.01) | |
| A61K 38/20 | (2006.01) | |
| A61K 9/00 | (2006.01) | |
| A61K 47/02 | (2006.01) | |
| A61K 47/10 | (2017.01) | |
| A61N 5/10 | (2006.01) | |

(52) U.S. Cl.
CPC .......... *A61K 38/208* (2013.01); *A61K 9/0019* (2013.01); *A61K 47/02* (2013.01); *A61K 47/10* (2013.01); *A61N 2005/1098* (2013.01)

(58) Field of Classification Search
None
See application file for complete search history.

(56) References Cited

U.S. PATENT DOCUMENTS

| | | |
|---|---|---|
| 3,773,919 A | 11/1973 | Boswell et al. |
| 4,179,337 A | 12/1979 | Davies et al. |
| 4,301,144 A | 11/1981 | Iwashita et al. |
| 4,485,045 A | 11/1984 | Regen |
| 4,496,689 A | 1/1985 | Mitra |
| 4,640,835 A | 3/1987 | Shimizu et al. |
| 4,670,417 A | 6/1987 | Iwasaki et al. |
| 4,791,192 A | 12/1988 | Nakagawa et al. |
| 5,013,556 A | 5/1991 | Woodle et al. |
| 4,544,545 A | 10/1995 | Ryan et al. |
| 5,573,764 A | 11/1996 | Sykes et al. |
| 5,648,072 A | 7/1997 | Trinchieri et al. |
| 5,648,467 A | 7/1997 | Trinchieri et al. |
| 5,744,132 A | 4/1998 | Warne et al. |
| 5,756,085 A | 5/1998 | Sykes et al. |
| 5,851,984 A | 12/1998 | Matthews et al. |
| 5,853,714 A | 12/1998 | Deetz et al. |
| 5,968,513 A | 10/1999 | Gallo et al. |
| 6,159,462 A | 12/2000 | Matthews et al. |
| 6,683,046 B1 | 1/2004 | Gately et al. |
| 2009/0312236 A1* | 12/2009 | Beals et al. .......... 514/3 |

FOREIGN PATENT DOCUMENTS

| | | |
|---|---|---|
| WO | WO 2005/007093 A2 | 1/2005 |
| WO | WO 2006/131515 A2 | 12/2006 |
| WO | WO 2007/016562 | 2/2007 |

OTHER PUBLICATIONS

Kolchanov, 1988, Journal of Molecular Evolution, vol. 27, pp. 154-162.*
Pasquo, 2012, PLoS ONE, vol. 7, Issue 2, e32555.*
Zagozdzon et al., "Effective Chemo-Immunotherapy of L 1210 Leukemia In Vivo Using Interleukin-12 Combined with Doxorubicin But not with Cyclophosphamide, Paclitaxel or Cisplatin," *Int. J. Cancer*, vol. 77, pp. 720-727 (1998).
Jackson et al., "Interleukin-12 Enhances Peripheral Hematopoiesis In Vivo," *Blood*, vol. 85, No. 9, pp. 2371-2376 (1995).
Ohno et al, "A Dose-Escalation and Pharmacokinetic Study of Subcutaneously Administered Recombinant Human Interleukin 12 and Its Biological Effects in Japanese Patients with Advanced Malignancies,"*Clinical Cancer Research*, vol. 6, pp. 2661-2669 (2000).
International Search Report issued in related International Patent Application No. PCT/US2011/036936, completed Jul. 22, 2011.
Abrams et al., "Mononuclear Cell Collections from the Peripheral Blood: Potential for Use in Autotransplantation," *J. Cell. Biochem.*, Suppl. 7 A, p. 53 (1983).
Airoldi et al., Expression and Function of IL-12 and IL-18 Receptors on Human Tonsillar B Cells, 2000, Journal of Immunology., 165:6880-6888.
Atkins, Dose-dense chemotherapy as adjuvant treatment for breast cancer, J Clin Oncol., 2004, 22(4):749-750.
Basile et al., "Multilineage hematopoietic recovery with concomitant antitumor effects using low dose interleukin-12 in myelosuppressed tumor-bearing mice," *J. Transl. Med.*, vol. 6, No. 26, pp. 1-27 (2008).
Brunda et al., Antitumor and antimetastic activity of interleukin 12 against murine tumors, 1993, J. Exp. Med., 178:1223-1230.
Buchwald et al., Long-term continuous intravenous heparin administration by an implantable infusion pump in ambulatory patients with recurrent venous thrombosis, Surgery, 88(4):507-516 (1980).
Chen et al., "IL-12 Facilitates Both the Recovery of Endogenous hematopoiesis and the Engraftment of Stem Cells after Ionizing Radiation," *Exp. Hematol.*, vol. J5, No. 2, pp. 203-213 (2007).
Cain et al, Myasthenia gravis and polymyositis in a dog following fetal hematopoietic cell transplantation, 1986, Transplantation, vol. 41, pp. 21-25 (1986), (Abstract).
Car et al., Role of interferon-gamma in interleukin 12-induced pathology in mice, 1995, American Journal of Pathology, 147:1693-1707.

(Continued)

*Primary Examiner* — Christine J Saoud
*Assistant Examiner* — Jegatheesan Seharaseyon
(74) *Attorney, Agent, or Firm* — Foley & Lardner LLP

(57) ABSTRACT

Provided are formulations for proteins to be injected into mammals. Specifically, formulations for recombinant IL-12 in mice and primates.

8 Claims, 12 Drawing Sheets

(56) References Cited

OTHER PUBLICATIONS

Car et al., "The Toxicology of Interleukin-12: A Review," *The Toxicol. Pathol.*, vol. 27, pp. 58-63 (1999).
Chi et al., "Physical Stability of Proteins in Aqueous Solution: Mechanism and Driving Forces in Nonnative Protein Aggregation," *Pharm. Res.*, vol. 20, No. 9, pp. 1325-1336 (2003).
Cleland et al., "The Development of Stable Protein Formulations: A Close Look at Protein Aggregation, Deamidation, and Oxidation," *Crit. Rev. Ther. Drug Carrier Syst.,*, vol. 70, No. 4, pp. 307-377 (1993).
Colombo, M. et al. "Interleukin-12 in Anti-tumor Immunity and Immunotherapy." Cytokine & Growth *Factor Reviews*, vol. 13, 155-168 (2002).
Cui et al., Requirements for Valpha14 NKT cells in IL-12-mediated rejection of tumors. 1997, Science, 278:1623-1626.
Dalod et al., Interferon alpha/beta and interleukin 12 responses to viral infections: pathways regulating dendritic cell cytokine expression in vivo, 2002, J. Exp. Med., 195:517-528.
During et al., Controlled release of dopamine from a polymeric brain implant: in vivo characterization., Ann. Neurol., 25:351-356 (1989).
Eng et al., The stimulatory effects of interleukin (IL)-12 on hematopoiesis are antagonized by IL-12-induced interferon gamma in vivo, 1995, J. Exp Med., 181:1893-1898.
Eppstein et al., Biological activity of liposome-encapsulated murine interferon gamma is mediated by a cell membrane receptor, PNAS, 82:3688-3692 (1985).
Kobayashi et al., "Identification and Purification of National Killer Cell Stimulatory Factor (NKSF), a Cytokine with Multiple Biologic Effects on Human Lymphocytes," *J. Exp. Med.*, vol. 170, pp. 827-845 (1989).
Freireich, E.J. et al., "Quantitative Comparison of Toxicity of Anticancer Agents in Mouse, Rat, Hamster, Dog, Monkey, and Man." Cancer Chemotherapy Reports, vol. 50, pp. 219-(1966).
Gazzinelli et al., Parasite-induced IL-12 stimulates early IFN-gamma synthesis and resistance during acute infection with Toxoplasma gondii, 1994, J. Immunol., 153:2533-2543 [Abstract].
Nanni et al., "Combined Allogentic Tumor Cell Vaccination and Systemtic Interleukin 12 Prevents Mammary Carcinogeneisis in HER-2/neu Transgenic Mice," *J. Exp. Med.,*, vol. 194, pp. 1195-1206 (2001).
Goldman et al., Haematological reconstitution after autografting for chronic granulocytic leukaemia in transformation: the influence of previous splenectomy, Br. J. Haematol., 45:223-231 (1980) [Abstract].
Goodson, "The Scope of Dental Therapy," *Medical Applications of Controlled Release*, vol. 2, pp. 115-138 (1984).
Hayes et al., Interferon-gamma-dependent inducible expression of the human interleukin-12 p35 gene in monocytes initiates from a TATA-containing promoter distinct from the CpG-rich promoter active in Epstein-Barr virus-transformed lymphoblastoid cells., Blood, 91:4645-4651 (1998).
Herodin et al., "Revisiting therapeutic strategies in radiation casualties," Exp. Hematol., vol. 55, pp. 28-33 (2007).
Hershko et al., Cure of aplastic anaemia in paroxysmal nocturnal haemoglobinuria by marrow transfusion from identical twin: Failure of peripheral-leucocyte transfusion to correct marrow aplasia, 1979, Lancet, 1:945-947 [Abstract].
Hirao et al. Synergism of interleukin 12, interleukin 3 and serum factor on primitive human hamatopoietic progenitor cells, 1995, Stem Cells, 13:47-53.
Hirokawa et al., "Restoration of impaired Immune Functions in Aging Animals, " *Clin. Immunol. Immunopathol.*, vol. 22, pp. 297-304 (1982).
Howard et al., Interacerebral drug delivery in rats with lesion-induced memory deficits. J. Neurosurg, 71:105-112 (1989) [Abstract].
Hsieh et al., Development of TH1 CD4+ T cells through IL-12 produced by Listeria-induced macrophages, 1993, Science, 260:547-549.

Hudis, C., et al. "Dose-Dense Chemotherapy in Breast Cancer and Lymphoma." Seminars in Oncology, vol. 31, No. 3, Suppl 8 (Jun.), 2004, 19-26.
Hwang et al., Hepatic uptake and degradation of unilamellar sphingomyelin/cholesterol liposomes: a kinetic study, *PNAS*, 77, pp. 4030-4034 (1980).
Jacobsen et al., Cytotoxic lymphocyte maturation factor (interleukin 12) is a synergistic growth factor for hamatopoietic stem cells, *J. Exp Med.*, 178(2), pp. 413-418 (1993).
Juttner et al., Circulating autologous stem cells collected in very early remission from acute non-lymphoblastic leukaemia produce prompt but incomplete haemopoietic reconstitution after high dose melphalan or supralethal chemoradiotherapy, Brit. J. Haematol., 61:739-745 (1985) [Abstract].
Keith et al., Improved outcome with dose-dense chemotherapy, J. Clin. Oncol., Feb. 15, 22(4), pp. 749-750 (2004).
Koenigsmann et al., Fludarabine and bendamustine in refractory and relapsed indolent lymphoma—a multicenter phase I/II Trial of the east german society of hematology and oncology (OSHO)., *Leuk Lymphoma*, 45(9), pp. 821-1827 (2004), (Abstract).
Korbling et al, Autologous transplantation of blood-derived hemopoietic stem cells after myeloablative therapy in a patient with Burkitt's lymphoma, *Blood*, vol. 67, pp. 529-532 (1986).
Lajtha L.G., "Haemopoietic Stem Cells: Concepts and Definitions," *Blood Cells*, vol. 5, pp. 447-455 (1979).
Langer, New methods of drug delivery, Science, vol. 249, pp. 1527-1533 (1990).
Lenzi et al., Phase I study of intraperitoneal recombinant human interleukin 12 in patients with Müllerian carcinoma, gastrointestinal primary malignancies, and mesothelioma, *Clinical Cancer Research*, vol. 8, pp. 3686-3695 (2002).
Lertmemongkotchai et al., Bystander activation of CD8+ T cells contributes to the rapid production of IFN-gamma in response to bacterial pathogens, *Journal of Immunology.*, 166:1097-1105 (2001).
Levy et al., Inhibition of calcification of bioprosthetic heart valves by local controlled-release diphosphonate, Science, 228:190-192 (1985).
Manetti et al., Natural killer cell stimulatory factor (interleukin 12 [IL-12]) induces T helper type 1 (Th1)-specific immune responses and inhibits the development of IL-4-producing Th cells, J. Exp. Med., vol. 177, pp. 1199-1204 (1993).
Maurel et al, Sequential dose-dense doxorubicin and ifosfamide for advanced soft tissue sarcomas: a Phase II trial by the Spanish Group for Research on Sarcomas (GEIS), Cancer, 2004, 100(7):1498-1506.
Neta et al., "IL-12 Protects Bone Marrow from and Sensitizes Intestinal Tract to Ionizing Radiation," *J. Immonol.*, vol. 153, pp. 4230-4237 (1994).
Noguchi et al., Effect of interleukin 12 on tumor induction by 3-methylcholanthrene, 1996, PNAS, 93:11798-11801.
Northdurft et al., Studies on the regeneration of th CFU-C population in blood and bone marrow of lethally irradiated dogs after autologous transfusion of cryopreserved mononuclear blood cells, Scand. J. Haematol., 1977, 19(5):470-481 [Abstract].
OCHS et al., "Immune Reconstitution in Adenosine Dearninase Deficient Severe Combined Imune Deficiency," *Pediatr. Res.*, vol. 15, p. 601 (1981) (Abstract).
Ohteki et al., Interleukin 12-dependent interferon gamma production by CD8alpha+ lymphoid dendritic cells, 1999, J. Exp. Med., 189:1981-1986.
Paige et al., Precursors of murine B lymphocytes. Physical and functional characterization, and distinctions from myeloid stem cells, 1981, J. Exp. Med., 153: 154-165.
Pillow et al., "Treatment of Bone-Marrow Failure by Isogeneic Marrow Infusion," *N. Engl. J. Med.*, vol. 275, pp. 94-97 (1966).
Ploemacher, R., et al. "Interleukin-12 Enhances Interleukin-3 Dependent Mulilineage Hematopoietic Colony Formation Stimulated by Interleukin-11 or Steel Factor." *Leukemia*, vol. 7, No. 9, pp. 1374-1380 (1993).
Presky et al., A functional interleukin 12 receptor complex is composed of two beta-type cytokine receptor subunits., 1996, PNAS, 93:14002-14007.

(56) References Cited

OTHER PUBLICATIONS

Prummer et al., Recovery of immune functions in dogs after total body irradiation and transplantation of autologous blood or bone marrow cells. 1985, Exp. Hematol., 13:891-898 [Abstract].

Ragharachar et al., "Comparison of the Repopulating Potential of Stem Cells Derived from Blood and Bone Marrow; Autotransplants in Dogs," *J. Cell Biochem.*, Suppl. 7A, p. 78 (1983).

Langer et al., "Chemical and Physical Structure of Polymers as Carriers for Controlled Release of Bioactive Agents: A Review," *J. Macromol. Sci. Rev. Macromol. Chem.*, vol. 23, pp. 61-126 (1938).

Reis de Sousa et al, In vivo microbial stimulation induces rapid CD40 ligand-independent production of interleukin 12 by dendritic cells and their redistribution to T cell areas, 1997, J. Exp. Med., 186:1819-1829.

Robertson et al, Immunological effects of interleukin 12 administered by bolus intravenous injection to patients with cancer, 1999, Clinical Cancer Research, 5:9-16.

Ryffel, B. "Interleukin-12: Role of Interferon-y in IL-12 Adverse Effects." Clinical Immunology and Immunopathology, vol. 83, No. 1, Apr. 18-20, 1997.

Sarpel et al., "The Collection, Preservation and Function of Peripheral Blood Hematopoietic Cells in Dogs," *Exp. Hematol.*, vol. 7, pp. 113-120 (1779).

Saudek et al., A preliminary trial of the programmable implantable medication system for insulin delivery, N. Engl. J. Med., 321:574-579, (1989).

Sefton, Implantable pumps, Crit Rev Biomed Eng. 14:201-240 (1987).

Strober et al., "Efficacy of Total Lymphoid Irradiation in Intractable Rheumatoid Arthritis," Annals of Internal Medicine, vol. 102, pp. 441-449 (1985).

Strober et al., "Treatment of Intractable Lupus Nephritis with Total Lymphoid Irradiation," Annals of Internal Medicine, vol. 102, 450-458 (1985).

Thomas et al., "Aplastic Anemia Treated By Marrow Transplantation," *The Lancet*, pp. 284-289 (1972).

Tilly et al., "Haemopoietic Reconstitiution after Autotogous Peripheral Blood Stem Cell Transplantation in Acute leukaemia," *The Lancet*, pp. 154-155 (1986).

To et al., Peripheral Blood Stem Cell Autografting: A New Therapeutic Option for AML, Brit. J. Haematol., vol. 66, pp. 285-288 (1987).

Touraine, European Experience with Fetal Tissue Transplantation in Severe Combined Immunodeficiency (SCID), *J.L., Birth Defects*, vol. 19, pp. 139-142 (1983).

Touraine, "Transplantation of Both Fetal Liver and Thymus in Severe Combined Immuodeficiencies," Excerpta Med., vol. 514, p. 277-283, (1980).

Treat et al., In Liposomes in the Therapy of Infectious Disease and Cancer, Lopez-Berestein and Fidler (eds.), Liss, New York, pp. 353-365 (1989); LopezBerestein, ibid., pp. 317-327; see generally ibid.).

Tsukuda et al., "Phase I Trial of Combined Chemotherapy with Docetaxel, Cisplatin, and 5-fluorouracil for patients with locally advanced squarmous cell carcinoma of the head and neck." *Int. J. Clin. Oncol.*, vol. 9, No. 3, pp. 161-166 (2004).

Vickery et al.,"Effect of Immune Reconstitution on Resistance to Brugia Pahangi in Congenitially Athymic Nude Mice," *J. Parasitol*, vol. 69, No. 3. pp. 478-485 (1983).

Wang, "Instability, stabilization, and formulation of liquid protein pharmaceuticals," *Int. J. Pharm.*, vol. 7S5, No. 2, pp. 129-188 (1999).

Wang, "Lyophilization and development of solid protein pharmaceuticals," *Int. J. Pharm.*, vol. 203, No. 1-2, pp. 1-60 (2000).

Harrison's Principles of Internal Medicine, $6^{th}$ Ed., McGraw-Hill, pp. 798-1044 (1970) [Table of Contents Only].

Wu et al., "Biological function and distribution of human interleukin-12 receptor β chain," *Eur. J. Immunol.*, vol. 26, pp. 345-350 (1996).

Wu et al, Receptor-mediated in vitro gene transformation by soluble DNA carrier system, *J. Biol. Chem.*, vol. 262, pp. 4429-4432 (1987).

Yao et al., Effective targeting of tumor vasculature by the angiogenesis inhibitors vasostatin and interleukin-12, Blood, 96:1900-1905 (2000).

Tulunay et al., "Protection of Lethally irradiated mice with allogeneic fetal liver cells: Influence of irradiation dose on immunologic reconstitution," *Proc. Natl. Acad. Sci.*, vol. 72, pp. 4100-4104 (1974).

Notice of Reasons for Rejection issued in related Japanese Patent Application No. 2013-511320, dated May 7, 2015.

\* cited by examiner

IL-12 FORMULATIONS FOR ENHANCING HEMATOPOIESIS

CROSS-REFERENCE TO RELATED APPLICATIONS

This application claims priority to U.S. Provisional Patent Application No. 61/345,986, filed on May 18, 2010, the entirety of which is incorporated by reference.

BACKGROUND OF THE INVENTION

It is known that administration of Interleukin-12 (IL-12) facilitates both the recovery of endogenous hematopoiesis and the engraftment of stem cells after ionizing radiation. Burke et al., *Exp. Hematol.*, 35(2):203-13 (February 2007). In addition, it is known that low dose IL-12 can result in multilineage hematopoietic recovery with concomitant antitumor effects in myelosuppressed tumor-bearing mice. Basile et al., *J. Transl. Med.*, 6:26 (May 2008). See also Herodin et al., *Exp Hematol.*, 35:28-33 (2007).

There remains a need in the art for new formulations and methods for treating deficiencies in hematopoiesis. The present invention satisfies this need.

SUMMARY OF THE INVENTION

Embodiments of the present invention provide for various compositions of Interleukin-12 (IL-12) or an IL-12 variant in a formulation that includes a stabilizer and a surfactant in a buffered solution. Uses of such formulations in hematopoiesis, particular for stimulating or enhancing hematopoiesis in a mammal in need, are also encompassed by the invention. The present invention includes various compositions and approaches to using IL-12 or an IL-12 variant to increase the production of hematopoietic cell types or lineages.

A particular embodiment of the present invention is directed to treating a disease state in a mammal, where treatment modalities themselves generally produce decreases or deficiencies in hematopoiesis as a limiting toxicity to the treatment modality. Other embodiments of the invention provide for methods of generally treating a mammal for a deficiency in one or more hematopoietic cell types or lineages, methods for stimulating or enhancing hematopoiesis, and methods of preservation and recovery cells that comprise bone marrow.

An indication of the therapeutic effectiveness of the therapeutic methods of the present invention is demonstrated by the ability of these methods to confer survival on lethally irradiated animals as illustrated below. Recovery from lethal irradiation provides an extreme indication of the therapeutic effectiveness of the methods of the present invention. However, as shown in the examples below, the therapeutic methods of the present invention can promote hematopoiesis and hematopoietic recovery in the face of less than lethal doses of irradiation, or less than lethal doses of chemotherapeutic agents, or in disease states where increased hematopoiesis is of therapeutic benefit.

The first embodiment of the methods of the invention involves treating the mammal for a general treatment-induced deficiency in hematopoiesis. The second embodiment of the methods of the invention involves treating the mammal for a deficiency in hematopoiesis where the deficiency is substantially the result of a disease state, but may be exacerbated by treatment modalities. Both embodiments of the invention provide for enhanced hematopoiesis and/or hematopoietic recovery by administering interleukin-12, or a substantial equivalent thereof, to the mammal.

Other embodiments of the present invention provide methods of using IL-12 to promote, stimulate or enhance hematopoiesis and/or hematopoietic recovery in mammals suffering from a deficiency or defect in hematopoiesis. Still other embodiments provide for preservation or recovery of bone marrow by administering IL-12 in accordance with the methods provided herein. Moreover, in all embodiments of the invention, IL-12 promoted, stimulated or enhanced hematopoiesis appears to be largely generated from the level of the hematopoietic repopulating, hematopoietic stem or hematopoietic progenitor cell compartment. Further, the uses of IL-12 in embodiments of the invention are particularly useful as methods of treatment in the medical fields of oncology and hematology.

In one embodiment of the invention, encompassed is a pharmaceutical IL-12 composition comprising: (a) about 0.01 to about 250 ng/ml IL-12 or an IL-12 variant; (b) about 0.01% to about 40% at least one stabilizer; (c) about 0.001% to about 20% surfactant; and (d) water, wherein the IL-12 is solubilized and the solution has a pH of about 3.0 up to about 9. In another embodiment, the pH is selected from the group consisting of about 3.5 to about 8.5, about 4 to about 8, about 4.5 to about 7.5, about 5.0 to about 7.0, and about 5.5 to about 6.5, about 6.0.

The composition can comprises IL-12 or an IL-12 variant in an amount: (a) selected from the group consisting of less than about 2000 ng/ml, less than about 1500 ng/ml, less than about 1000 ng/ml, less than about 500 ng/ml, less than about 250 ng/ml, less than about 240 ng/ml, less than about 230 ng/ml, less than about 220 ng/ml, less than about 210 ng/ml, less than about 200 ng/ml, less than about 190 ng/ml, less than about 180 ng/ml, less than about 170 ng/ml, less than about 160 ng/ml, less than about 150 ng/ml, less than about 140 ng/ml, less than about 130 ng/ml, less than about 120 ng/ml, less than about 110 ng/ml, less than about 100 ng/ml, less than about 90 ng/ml, less than about 80 ng/ml, less than about 70 ng/ml, less than about 60 ng/ml, less than about 55 ng/ml, less than about 50 ng/ml, less than about 45 ng/ml, less than about 40 ng/ml, less than about 35 ng/ml, less than about 30 ng/ml, less than about 25 ng/ml, less than about 20 ng/ml, less than about 15 ng/ml, less than about 10 ng/ml, and less than about 5 ng/ml; or, (b) selected from the group consisting of a range from 2 to 5 µg/ml, 1 to 10 µg/ml, 0.5 to 20 µg/ml, and 0.1 to 50 µg/ml.

The stabilizer can be present in the IL-12 composition in an amount selected from the group consisting of less than about 40%, less than about 30%, less than about 25%, less than about 20%, less than about 15%, less than about 10%, less than about 9%, less than about 8%, less than about 7%, less than about 6%, less than about 5%, less than about 4%, less than about 3%, less than about 2%, less than about 1%, and less than about 0.05%. In one embodiment, the stabilizer is a salt, such as sodium chloride.

The surfactant can be present in the IL-12 composition in an amount selected from the group consisting of less than about 20%, less than about 15%, less than about 10%, less than about 9%, less than about 8%, less than about 7%, less than about 6%, less than about 5%, less than about 4%, less than about 3%, less than about 2%, less than about 1%, less than about 0.05%, less than about 0.01%, and less than about 0.005%. In one embodiment, the surfactant is a poloxamer, such as poloxamer 188.

In another embodiment of the invention, the IL-12 composition can comprise about 150 mM sodium chloride and about 0.1% poloxamer 188, wherein the composition has a pH of at least pH 5.5 and less than pH 6.5.

Also encompassed by the invention is a method of treating a disease state in a mammal comprising: (a) administering to the mammal a treatment having an associated hematopoietic toxicity; and (b) administering one or more therapeutically effective dose(s) of an IL-12 composition according to the invention near the time of administration of the treatment, wherein the administration of the IL-12 composition to the mammal reduces the hematopoietic toxicity of the treatment. The mammal can be a human. In addition, the treatment can comprise chemotherapy, radiation therapy, or a combination thereof.

In such a method, the treatment can comprise one or more high dose treatment modalities, the treatment can be administered in a dose dense treatment regimen, or a combination thereof. In addition, administration of the composition can result in protection of bone marrow cells from the associated hematopoietic toxicity of the treatment. Administration of the composition can also result in chemoprotection of bone marrow cells. The bone marrow cells can comprise hematopoietic repopulating cells, hematopoietic stem cells, hematopoietic progenitor cells, or any combination thereof.

The treatment can be targeted: (a) to treat one or more solid tumors; (b) to treat one or more hematopoietic cell disorders; or (c) to treat virus infection. In one embodiment of the invention, where the treatment is targeted to treating one or more solid tumors, the method results in an increased remission of the one or more solid tumors, as compared with the treatment intended to target the disease state alone. In another embodiment, where the treatment is targeted to treating one or more hematopoietic cell disorders, the method results in an increased remission of the one or more hematopoietic cell disorders, as compared with the treatment intended to target the disease state alone. In yet another embodiment, where the treatment is targeted to treating virus infection, (a) the method results in a decrease in the virus infection or its associated symptoms; (b) the white blood cell count of the mammal is increased; (c) the T-cell count of the mammal is increased; or (d) any combination thereof.

In one embodiment of the invention, the treatment comprises chemotherapy and the chemotherapy leads to a deficiency in one or more hematopoietic cell types or lineages and the administration of the composition ameliorates the deficiency. In another embodiment, the chemotherapy treatment comprises administration of more than one chemotherapy.

In the methods of the invention, the composition can be administered before the chemotherapy, the composition can be administered after the chemotherapy, the composition can be administered before or after the chemotherapy, and the composition can be administered before and after chemotherapy.

In another embodiment of the invention, the treatment comprises radiation therapy and (a) administration of the composition results in radioprotection of bone marrow cells; (b) administration of the composition results in radioprotection of bone marrow cells and the bone marrow cells comprise hematopoietic repopulating cells, hematopoietic stem cells hematopoietic progenitor cells, or any combination thereof; or any combination thereof.

In the methods of the invention, the radiation therapy can comprise a near-lethal dose of radiation, or the radiation therapy can comprise a sub-lethal dose of radiation. In addition, the radiation therapy can be administered in a dose dense treatment regimen.

The IL-12 composition can be administered before the radiation therapy, the IL-12 composition can be administered after the radiation therapy, the IL-12 composition can be administered before or after the radiation therapy, and the IL-12 composition can be administered before and after the radiation therapy. Also in the methods of the invention, the radiation therapy can lead to a deficiency in one or more hematopoietic cell types or lineages and the administration of the IL-12 composition ameliorates the deficiency.

In the methods of the invention, one or more therapeutically effective dose(s) of the IL-12 composition can be administered at various time intervals before, before and after, or after the administration of the treatment.

In yet another embodiment of the invention, encompassed is a method of treating a mammal for a deficiency in hematopoiesis comprising administering one or more therapeutically effective dose(s) of an IL-12 composition according to the invention as needed to ameliorate the deficiency. The deficiency in hematopoiesis can comprise a deficiency in one or more hematopoietic cell types or lineages. In addition, the mammal can be a human. The deficiency (a) can be ameliorated by the IL-12 or IL-12 variant facilitated proliferation of one or more types of bone marrow cells; (b) can be ameliorated by the IL-12 or IL-12 variant facilitated proliferation of hematopoietic repopulating cells, hematopoietic stem cells, hematopoietic progenitor cells, or any combination thereof; (c) can be exacerbated by chemotherapy, radiation therapy, or a combination thereof; or (d) any combination thereof. In another embodiment, the deficiency (a) is substantially the result of a disease state; (b) comprises a lymphopenia; (c) comprises a myelopenia; (d) comprises a leucopenia; (e) comprises a leukopenia which is neutropenia; (f) comprises erythropenia; (g) comprises megakaryopenia; (h) comprises a deficiency in platelets; (i) comprises a deficiency in lymphocytes; (j) comprises a deficiency in erythrocytes; (k) comprises a deficiency in monocytes; (l) comprises a deficiency in neutrophils; (m) comprises a deficiency in T cells; (n) comprises a deficiency in granulocytes; (o) comprises a deficiency in dendritic cells; or (p) any combination thereof.

In one embodiment of the invention, encompassed is a method of stimulating or enhancing hematopoiesis in a mammal comprising administering one or more therapeutically effective dose(s) of an IL-12 composition according to the invention for a duration to achieve a therapeutic effect comprising the stimulation or enhancement of hematopoiesis. In such a method, (a) the stimulation or enhancement of hematopoiesis involves the IL-12 or IL-12 variant facilitated proliferation of bone marrow cells; or (b) the stimulation or enhancement of hematopoiesis involves the IL-12 or IL-12 variant facilitated proliferation of hematopoietic repopulating cells, hematopoietic progenitor cells, hematopoietic stem cells, or (c) any combination thereof. The hematopoietic repopulating cells can comprise long-term repopulating cells. Moreover, the method can further comprise administration of radiation therapy, administration of chemotherapy, or a combination thereof. In one embodiment, the mammal has (a) a deficiency in one or more hematopoietic cell types or lineages; (b) a hematopoietic deficiency comprising lymphopenia; (c) a hematopoietic deficiency comprising myelopenia; (d) a hematopoietic deficiency comprising leucopenia; (e) a hematopoietic deficiency comprising leukopenia and the leukopenia is neutropenia; (f) a hematopoietic deficiency comprising a erythropenia; (g) a deficiency comprising megakaryopenia; (h) a hematopoietic deficiency comprising a deficiency in platelets; (i) a hematopoietic deficiency comprising a deficiency in monocytes; (k) a hematopoietic deficiency comprising a deficiency in lymphocytes; (l) a hematopoietic deficiency comprising a deficiency in erythrocytes; (m) a hematopoietic deficiency comprising a deficiency in neutrophils; (n) a hematopoietic deficiency comprising a deficiency in T cells; (o) a hematopoietic deficiency comprising a deficiency in granulocytes; (p) a hematopoietic deficiency comprising a deficiency in dendritic cells; or (q) any combination thereof.

In another embodiment of the invention, encompassed is a method for bone marrow preservation or recovery in a mammal comprising administering one or more therapeutically effective dose(s) of an IL-12 composition according to the invention to the mammal, without the use of hemtopoietic repopulating cells, hematopoietic progenitor cells or hematopoietic stem cells, for a duration necessary for bone marrow preservation or recovery. In such a method, the mammal can have bone marrow failure. In addition, the mammal can be suffering from a disease state and near destruction of the bone marrow as a by-product of a treatment regimen to combat the disease state. The administration of therapeutically effective doses of the IL-12 composition of the invention can be for a duration necessary for bone marrow preservation or recovery, which thereby obviates the need for a bone marrow transplant. The bone marrow preservation or recovery can include (a) an increase in hematopoietic repopulating cell; (b) an increase in hematopoietic stem cells; (c) an increase in hematopoietic progenitor cells; (d) an increase in one or more differentiated hematopoietic cells types; (e) an increase in hematopoietic support cells; or (f) any combination thereof. In another embodiment, the mammal can have (a) a deficiency in one or more hematopoietic cell types or lineages; (b) a hematopoietic deficiency comprising lymphopenia; (c) a hematopoietic deficiency comprising myelopenia; (d) a hematopoietic deficiency comprising leucopenia; (e) a hematopoietic deficiency comprising leucopenia wherein the leukopenia is neutropenia; (f) a hematopoietic deficiency comprising a erythropenia; (g) a deficiency comprising megakaryopenia; (h) a hematopoietic deficiency comprising a deficiency in platelets; (i) a hematopoietic deficiency comprising a deficiency in monocytes; (j) a hematopoietic deficiency comprising a deficiency in lymphocytes; (k) a hematopoietic deficiency comprising a deficiency in erythrocytes; (l) a hematopoietic deficiency comprising a deficiency in neutrophils; (m) a hematopoietic deficiency comprising a deficiency in T cells; (n) a hematopoietic deficiency comprising a deficiency in granulocytes; (o) a hematopoietic deficiency comprising a deficiency in dendritic cells; or (p) any combination thereof.

In another embodiment of the invention encompassed is a method for increasing survival in a subject, and/or preserving bone marrow function, and/or promoting hematopoietic recovery or restoration, comprising administering an IL-12 composition according to the invention to the subject following an acute exposure to non-therapeutic whole body ionizing radiation. For example, the acute whole body ionizing radiation can be a nuclear event, and the acute dose can be at least about 3.5 Gy (LD50). In addition, the subject can be a human. In such a method, the composition can be administered at any suitable timepoint, such as (a) between a range of about 1 hour to about 72 hours after the acute radiation exposure; or (b) between a range of about 6 hour to about 24 hours after the acute radiation exposure. In addition, the IL-12 composition can be administered subcutaneously or intramuscularly. In such a method, supportive care can be given to the subject simultaneously or following the administration of the composition. Such supportive care can include the administration of one or more antibiotics, the administration of one or more hematopoietic growth factors, the administration of a blood transfusion, or any combination thereof.

Finally, also encompassed by the invention is a kit for increasing survival in a subject, and/or preserving bone marrow function, and/or promoting hematopoietic recovery or restoration following non-therapeutic acute exposure to whole body ionizing radiation, the kit comprising one or more doses of an IL-12 composition according to the invention.

Both the foregoing general description and the following brief description of the drawings and detailed description are exemplary and explanatory and are intended to provide further explanation of the invention as claimed. Other objects, advantages, and novel features will be readily apparent to those skilled in the art from the following detailed description of the invention.

BRIEF DESCRIPTION OF THE FIGURES

FIG. 6.

DETAILED DESCRIPTION OF THE INVENTION

A. Summary of Embodiments

Figure 1:
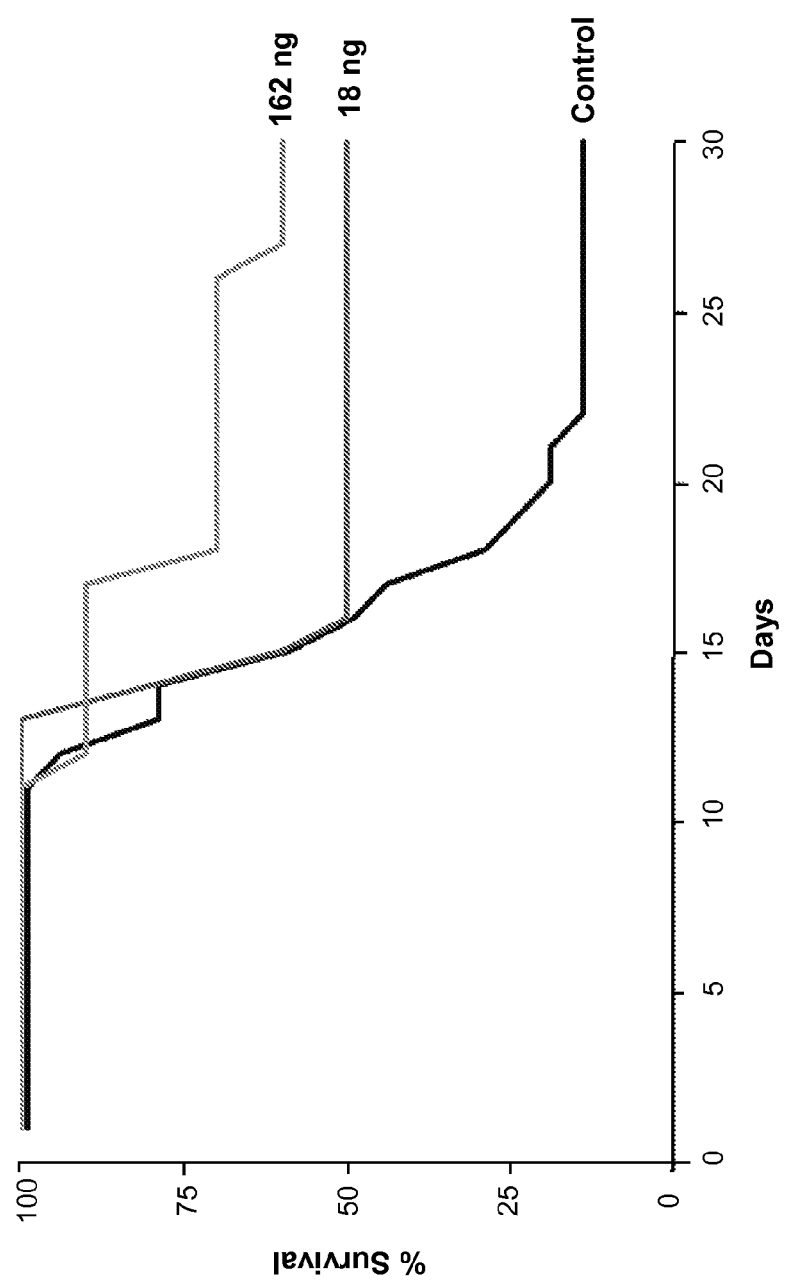
FIG. 1: Shows Kaplan-Meier (K-M) plots for murine RmIL-12 for a sucrose-based formulation following subcutaneous (SC) injection with RmIL-12 at 24 hours after exposure to 7.9 Gy. The results show that IL-12 in a sucrose formulation mitigates the effects of lethal irradiation of mice. Control mice received no IL-12 (line labeled "Control"); Treated mice received 18 ng (line labeled "18 ng") or 162 ng (line labeled "162 ng") IL-12 in a sucrose-based formulation.

In one embodiment of the invention, emcompassed is a pharmaceutical IL-12 composition comprising: (a) about 0.01 to about 250 ng/ml IL-12 or an IL-12 variant; (b) about 0.01% to about 40% at least one stabilizer; (c) about 0.001% to about 20% at least one surfactant; and (d) water, wherein the IL-12 is solubilized and the solution has a pH of about 3.0 up to about 9. The composition can comprise at least one buffer to obtain the desired pH.

In one embodiment of the invention, emcompassed is a pharmaceutical IL-12 composition comprising: (a) about 0.01 to about 250 ng/ml IL-12 or an IL-12 variant; (b) about 0.1 mM to about 250 mM at least one salt as a stabilizer; (c) about 0.001% to about 20% at least one poloxamer; and (d) water, wherein the IL-12 is solubilized and the solution has a pH of about 3.0 up to about 9. The composition can comprise at least one buffer to obtain the desired pH.

In another embodiment, the composition comprises IL-12 or an IL-12 variant in an amount selected from the group consisting of less than about 2000 ng/ml, less than about 1500 ng/ml, less than about 1000 ng/ml, less than about 500 ng/ml, less than about 250 ng/ml, less than about 240 ng/ml, less than about 230 ng/ml, less than about 220 ng/ml, less than about 210 ng/ml, less than about 200 ng/ml, less than about 190 ng/ml, less than about 180 ng/ml, less than about 170 ng/ml, less than about 160 ng/ml, less than about 150 ng/ml, less than about 140 ng/ml, less than about 130 ng/ml, less than about 120 ng/ml, less than about 110 ng/ml, less than about 100 ng/ml, less than about 90 ng/ml, less than about 80 ng/ml, less than about 70 ng/ml, less than about 60 ng/ml, less than about 55 ng/ml, less than about 50 ng/ml, less than about 45 ng/ml, less than about 40 ng/ml, less than about 35 ng/ml, less than about 30 ng/ml, less than about 25 ng/ml, less than about 20 ng/ml, less than about 15 ng/ml, less than about 10 ng/ml, and less than about 5 ng/ml.

In another embodiment, the composition comprises IL-12 or an IL-12 variant in an amount selected from the group consisting of more than about 1 µg/ml, more than about 500 ng/ml, more than about 250 ng/ml, more than about 240 ng/ml, more than about 230 ng/ml, more than about 220 ng/ml, more than about 210 ng/ml, more than about 200 ng/ml, more than about 190 ng/ml, more than about 180 ng/ml, more than about 170 ng/ml, more than about 160 ng/ml, more than about 150 ng/ml, more than about 140 ng/ml, more than about 130 ng/ml, more than about 120 ng/ml, more than about 110 ng/ml, more than about 100 ng/ml, more than about 90 ng/ml, more than about 80 ng/ml, more than about 70 ng/ml, more than about 60 ng/ml, more than about 55 ng/ml, more than about 50 ng/ml, more than about 45 ng/ml, more than about 40 ng/ml, more than about 35 ng/ml, more than about 30 ng/ml, more than about 25 ng/ml, more than about 20 ng/ml, more than about 15 ng/ml, more than about 10 ng/ml, and more than about 5 ng/ml.

In another embodiment, the composition comprises IL-12 or an IL-12 variant in an amount selected from the group consisting of ranges of 2 to 5 µg/ml, 1 to 10 µg/ml, 0.5 to 20 µg/ml, and 0.1 to 50 µg/ml.

The composition can comprise at least one stabilizer and/or at least one surfactant in varying amounts. For example, the composition can comprise at least one stabilizer in an amount selected from the group consisting of less than about 40%, less than about 30%, less than about 25%, less than about 20%, less than about 15%, less than about 10%, less than about 9%, less than about 8%, less than about 7%, less than about 6%, less than about 5%, less than about 4%, less than about 3%, less than about 2%, less than about 1%, and less than about 0.05%. The composition can also comprise at least one stabilizer in an amount selected from the group consisting of less than about 250 mM, less than about 225 mM, less than about 200 mM, less than about 175 mM, less than about 170 mM, less than about 160 mM, less than about 155 mM, less than about 150 mM, less than about 145 mM, less than about 140 mM, less than about 135 mM, less than about 130 mM, less than about 120 mM, less than about 100 mM, less than about 50 mM, and less than about 1 mM. In addition, the composition can comprise at least one surfactant in an amount selected from the group consisting of less than about 20%, less than about 15%, less than about 10%, less than about 9%, less than about 8%, less than about 7%, less than about 6%, less than about 5%, less than about 4%, less than about 3%, less than about 2%, less than about 1%, less than about 0.05%, less than about 0.01%, and less than about 0.005%.

In one embodiment of the invention, the stabilizer is a sugar, such as sucrose or trehalose. In one embodiment of the invention, the surfactant is polysorbate 20. In an exemplary composition, the composition comprises about 6% Trehalose and about 0.04% polysorbate 20, wherein the composition has a pH of at least pH 5.5 and less than pH 6.5.

The pH of the invention can be any pharmaceutically acceptable pH. For example, the composition can have a pH selected from the group consisting of about 3.5 to about 8.5, about 4 to about 8, about 4.5 to about 7.5, about 5.0 to about 7.0, and about 5.5 to about 6.5.

In one embodiment of the invention, the stabilizer is a salt, such as sodium chloride or potassium chloride. In one embodiment of the invention, the surfactant is poloxamer 188. In an exemplary composition, the composition comprises about 150 mM sodium chloride, and about 0.1% poloxamer 188, wherein the composition has a pH of at least pH 5.5 and less than pH 6.5.

In one embodiment of the invention, the composition has a pharmaceutically acceptable EC50 for expression of interferon gamma when peripheral blood mononuclear cells are exposed to the composition. In some embodiments, the composition has an EC50 selected from the group consisting of about 0.1 to 1 picograms, about 0.15 to 0.9 picograms, and about 0.2 to about 0.7 picograms.

In another embodiment of the invention, encompassed are methods using the compositions of the invention. Exemplary methods include first, a method of treating a disease state in a mammal comprising: (a) administering to the mammal a treatment having an associated hematopoietic toxicity; and (b) administering one or more therapeutically effective dose(s) of the composition of claim 1 near the time of administration of the treatment, wherein the administration of the composition of claim 1 to the mammal reduces the hematopoietic toxicity of the treatment.

In a second exemplary method, encompassed is a method of treating a mammal for a deficiency in hematopoiesis comprising administering one or more therapeutically effective dose(s) of the composition of the invention as needed to ameliorate the deficiency.

In a third exemplary method, encompassed is a method of stimulating or enhancing hematopoiesis in a mammal comprising administering one or more therapeutically effective dose(s) of the composition of the invention for a duration to achieve a therapeutic effect comprising the stimulation or enhancement of hematopoiesis.

In a fourth exemplary method, encompassed is a method for bone marrow preservation or recovery in a mammal comprising administering one or more therapeutically effective dose(s) of the composition of the invention to the mammal, without the use of hemtopoietic repopulating cells, hematopoietic progenitor cells or hematopoietic stem cells, for a duration necessary for bone marrow preservation or recovery.

In a fifth exemplary method, encompassed is a method for increasing survival in a subject, and/or preserving bone marrow function, and/or promoting hematopoietic recovery or restoration, comprising administering the composition of the invention to the subject following an acute exposure to non-therapeutic whole body ionizing radiation.

In all of the methods of the invention, the mammal can be a human.

In the methods of the invention, the treatment correlated with a deficiency in hematopoiesis can comprise chemotherapy, radiation therapy, or a combination thereof. The deficiency in hematopoiesis can comprise a deficiency in one or more hematopoietic cell types or lineages.

The methods of the invention can result in amelioration of the deficiency in hematopoiesis, wherein the deficiency is ameliorated by the IL-12 or IL-12 variant facilitated proliferation of one or more types of bone marrow cells. The bone marrow cells can comprise hematopoietic repopulating cells, hematopoietic stem cells, hematopoietic progenitor cells, or any combination thereof.

In the methods and compositions of the invention, the dose of IL-12 or IL-12 variant is selected from the group consisting of less than about 50 µg/ml, less than about 45 µg/ml, less than about 40 µg/ml, less than about 35 µg/ml, less than about 30 µg/ml, less than about 25 µg/ml, less than about 20 µg/ml, less than about 15 µg/ml, less than about 10 µg/ml, less than about 8 µg/ml, less than about 5 µg/ml, less than about 2 µg/ml, less than about 1.5 µg/ml, less than about 1 µg/ml, less than about 500 ng/ml, less than about 250 ng/ml, less than about 240 ng/ml, less than about 230 ng/ml, less than about 220 ng/ml, less than about 210 ng/ml, less than about 200 ng/ml, less than about 190 ng/ml, less than about 180 ng/ml, less than about 170 ng/ml, less than about 160 ng/ml, less than about 150 ng/ml, less than about 140 ng/ml, less than about 130 ng/ml, less than about 120 ng/ml, less than about 110 ng/ml, less than about 100 ng/ml, less than about 90 ng/ml, less than about 80 ng/ml, less than about 70 ng/ml, less than about 60 ng/ml, less than about 55 ng/ml, less than about 50 ng/ml, less than about 45 ng/ml, less than about 40 ng/ml, less than about 35 ng/ml, less than about 30 ng/ml, less than about 25 ng/ml, less than about 20 ng/ml, less than about 15 ng/ml, less than about 10 ng/ml, and less than about 5 ng/ml. In the methods and compositions of the invention, the dose of IL-12 or IL-12 variant is selected from the group consisting of more than about 1 µg/ml, more than about 500 ng/ml, more than about 250 ng/ml, more than about 240 ng/ml, more than about 230 ng/ml, more than about 220 ng/ml, more than about 210 ng/ml, more than about 200 ng/ml, more than about 190 ng/ml, more than about 180 ng/ml, more than about 170 ng/ml, more than about 160 ng/ml, more than about 150 ng/ml, more than about 140 ng/ml, more than about 130 ng/ml, more than about 120 ng/ml, more than about 110 ng/ml, more than about 100 ng/ml, more than about 90 ng/ml, more than about 80 ng/ml, more than about 70 ng/ml, more than about 60 ng/ml, more than about 55 ng/ml, more than about 50 ng/ml, more than about 45 ng/ml, more than about 40 ng/ml, more than about 35 ng/ml, more than about 30 ng/ml, more than about 25 ng/ml, more than about 20 ng/ml, more than about 15 ng/ml, more than about 10 ng/ml, and more than about 5 ng/ml. Dose ranges of IL-12 or IL-12 variant for the methods and compositions of the invention is selected from the group consisting of 2 to 5 µg/ml, 1 to 10 µg/ml, 0.5 to 20 µg/ml, and 0.1 to 50 µg/ml.

In the methods of the invention, the treatment correlated with a deficiency in hematopoiesis can comprise one or more high dose treatment modalities, the treatment can be administered in a dose dense treatment regimen, or any combination thereof. In one embodiment of the invention, the high dose treatment modality comprises administration of radiation therapy; the dose dense treatment regimen comprises administration of radiation therapy; or any combination thereof.

In the methods of the invention, the administration of the composition can result in protection of bone marrow cells from the associated hematopoietic toxicity of the treatment. For example, administration of the composition of the invention can result in chemoprotection of bone marrow cells. In another embodiment, the bone marrow cells can comprise hematopoietic repopulating cells, hematopoietic stem cells, hematopoietic progenitor cells, or any combination thereof.

In the methods of the invention, the treatment correlated with a deficiency in hematopoiesis can be targeted to treating one or more solid tumors, targeted to treating one or more hematopoietic cell disorders, and/or targeted to treating virus infection. Where the treatment is targeted to treating one or more solid tumors, the method can result in an increased remission of the one or more solid tumors, as compared with the treatment intended to target the disease state alone. Where the treatment is targeted to treating one or more hematopoietic cell disorders, the method can result in an increased remission of the one or more hematopoietic cell disorders, as compared with the treatment intended to target the disease state alone. Where the treatment is targeted to treating virus infection, (a) the method can result in a decrease in the virus infection or its associated symptoms; (b) the white blood cell count of the mammal can be increased; (c) the T-cell count of the mammal can be increased; or (d) any combination thereof.

In the methods of the invention, the treatment correlated with a deficiency in hematopoiesis can comprise chemotherapy and (a) the chemotherapy leads to a deficiency in one or more hematopoietic cell types or lineages and the administration of the composition ameliorates the deficiency; (b) the chemotherapy treatment comprises administration of more than one chemotherapy; (c) the composition is administered before the chemotherapy; (d) the composition is administered after the chemotherapy; (e) the composition is administered before or after the chemotherapy; (f) the composition is administered before and after chemotherapy; or (g) any combination thereof.

In the methods of the invention, the treatment correlated with a deficiency in hematopoiesis can comprise radiation therapy and (a) administration of the composition results in radioprotection of bone marrow cells; (b) administration of the composition results in radioprotection of bone marrow cells and the bone marrow cells comprise hematopoietic repopulating cells, hematopoietic stem cells hematopoietic progenitor cells, or any combination thereof; (c) the radiation therapy comprises a near-lethal dose of radiation; (d) the radiation therapy comprises a sub-lethal dose of radiation; (e) the radiation therapy is administered in a dose dense treatment regimen; (f) the composition is administered before the radiation therapy; (g) the composition is administered after the radiation therapy; (h) the composition is administered before or after the radiation therapy; (i) the composition is administered before and after the radiation therapy; (j) the radiation therapy leads to a deficiency in one or more hematopoietic cell types or lineages and the administration of the composition ameliorates the deficiency; or (k) any combination thereof.

One or more therapeutically effective dose(s) of the composition can be administered at various time intervals before, before and after, or after the administration of the treatment.

In the methods of the invention, the deficiency in hematopoiesis can be: (a) substantially the result of a disease state; (b) comprise a lymphopenia; (c) comprise a myelopenia; (d) comprise a leucopenia; (e) comprise a leukopenia which is neutropenia; (f) comprise erythropenia; (g) comprise megakaryopenia; (h) comprise a deficiency in platelets; (i) comprise a deficiency in lymphocytes; (j) comprise a deficiency in erythrocytes; (k) comprise a deficiency in monocytes; (l) comprise a deficiency in neutrophils; (m) comprise a deficiency in T cells; (n) comprise a deficiency in granulocytes; (o) comprises a deficiency in dendritic cells; or (p) any combination thereof.

In the methods of the invention, the stimulation or enhancement of hematopoiesis can involve the IL-12 or IL-12 variant facilitated proliferation of bone marrow cells. In another embodiment, the stimulation or enhancement of hematopoiesis can involve the IL-12 or IL-12 variant facilitated proliferation of hematopoietic repopulating cells, hematopoietic progenitor cells, hematopoietic stem cells, or any combination thereof. The hematopoietic repopulating cells can comprise long-term repopulating cells.

In the methods of the invention, the mammal can have (a) a deficiency in one or more hematopoietic cell types or lineages; (b) a hematopoietic deficiency comprising lymphopenia; (c) a hematopoietic deficiency comprising myelopenia; (d) a hematopoietic deficiency comprising leucopenia; (e) a hematopoietic deficiency comprising leucopenia and the leukopenia is neutropenia; (f) a hematopoietic deficiency comprising a erythropenia; (g) a deficiency comprising megakaryopenia; (h) a hematopoietic deficiency comprising a deficiency in platelets; (i) a hematopoietic deficiency comprising a deficiency in monocytes; (k) a hematopoietic deficiency comprising a deficiency in lymphocytes; (l) a hematopoietic deficiency comprising a deficiency in erythrocytes; (m) a hematopoietic deficiency comprising a deficiency in neutrophils; (n) a hematopoietic deficiency comprising a deficiency in T cells; (o) a hematopoietic deficiency comprising a deficiency in granulocytes; (p) a hematopoietic deficiency comprising a deficiency in dendritic cells; or (q) any combination thereof.

In a method for bone marrow preservation or recovery in a mammal, the mammal can have bone marrow failure. In another method, the mammal can be suffering from a disease state and near destruction of the bone marrow which is a by-product of a treatment regimen to combat the disease state. In yet another embodiment, the administration of therapeutically effective doses of the composition of the invention for a duration necessary for bone marrow preservation or recovery, obviates the need for a bone marrow transplant. In yet another embodiment, bone marrow preservation or recovery includes an increase in hematopoietic repopulating cell, hematopoietic stem cells, hematopoietic progenitor cells, or any combination thereof.

In the methods of the invention, bone marrow preservation or recovery can include (a) an increase in one or more differentiated hematopoietic cells types; (b) includes an increase in hematopoietic support cells; or (c) any combination thereof.

In a method of the invention directed to increasing survival in a subject, and/or preserving bone marrow function, and/or promoting hematopoietic recovery or restoration, comprising administering a composition of the invention to the subject following an acute exposure to non-therapeutic whole body ionizing radiation, the acute whole body ionizing radiation can be a nuclear event. The acute dose can be at least about 3.5 Gy (LD50). In addition, in such a method, the composition can be administered (a) between a range of about 1 hour to about 72 hours after the acute radiation exposure; (b) between a range of about 6 hour to about 24 hours after said acute radiation exposure; (c) subcutaneously or intramuscularly; or (d) any combination thereof. In addition, in such a method, (a) supportive care can be given to the subject simultaneously or following the administration of the composition; (b) supportive care can be given to the subject simultaneously or following the administration of the composition and supportive care comprises the administration of one or more antibiotics; (c) supportive care can be given to the subject simultaneously or following the administration of the composition and supportive care comprises administration of one or more hematopoietic growth factors; (d) supportive care can be given to the subject simultaneously or following the administration of the composition and supportive care comprises the administration of a blood transfusion; or (e) any combination thereof.

In another embodiment, the IL-12 or a variant thereof can be administered at least about 1 hour, at least about 2 hours, at least about 3 hours, at least about 4 hours, at least about 5 hours, at least about 6 hours, at least about 7 hours, at least about 8 hours, at least about 9 hours, at least about 10 hours, at least about 11 hours, at least about 12 hours, at least about 13 hours, at least about 14 hours, at least about 15 hours, at least about 16 hours, at least about 17 hours, at least about 18 hours, at least about 19 hours, at least about 20 hours, at least about 21 hours, at least about 22 hours, at least about 23 hours, at least about 24 hours, at least about 30 hours, at least about 36 hours, at least about 42 hours, at least about 48 hours, at least about 54 hours, at least about 60 hours, at least about 66 hours, or at least about 72 hours after the acute radiation exposure.

In another embodiment of the invention, the survival of the subject is increased, as compared to a subject exposed to the same dosage of radiation and not given IL-12 or a variant thereof, by about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or about 100%.

Finally, in another embodiment of the invention, encompassed is a kit for increasing survival in a subject, and/or preserving bone marrow function, and/or promoting hematopoietic recovery or restoration following non-therapeutic acute exposure to whole body ionizing radiation, the kit comprising one or more doses of a composition of an invention.

B. Definitions

The following definitions are provided to give clarity to language used within the specification. Language used to clarify definitions is meant to be interpreted broadly and generically.

"Interleukin-12 (IL-12)" as used herein includes any recombinant IL-12 molecule that yields at least one of the properties disclosed herein, including native IL-12 molecules, variant IL-12 molecules and covalently modified IL-12 molecules, now known or to be developed in the future, produced in any manner known in the art now or to be developed in the future. Generally, the amino acid sequence of the IL-12 molecule used in embodiments of the invention is the canonical human sequence related to IL-12p70. IL-12 comprises two subunits, IL-12A (p35) and IL-12 B (p40) Polymorphisms, however, are known to exist for IL-12, especially in the p35 subunit. In particular, a known polymorphism can exist at amino acid 247 of the p35 human subunit, where methionine is replaced by threonine. Still other embodiments of the invention include IL-12 molecules where the native amino acid sequence of IL-12 is altered from the native sequence, but the IL-12 molecule functions to yield the properties of IL-12 that are disclosed herein. Alterations from the native, species-specific amino acid sequence of IL-12 include changes in the primary sequence of IL-12 and encompass deletions and additions to the primary amino acid sequence to yield variant IL-12 molecules. An example of a highly derivatized IL-12 molecule is the redesigned IL-12 molecule produced by Maxygen, Inc. (Leong et al., *Proc Natl Acad Sci USA*, 100(3): 1163-8 (Feb. 4, 2003), where the variant IL-12 molecule is produced by a DNA shuffling method. Also included are modified IL-12 molecules included in the methods of invention, such as covalent modifications to the IL-12 molecule that increase its shelf life, half-life, potency, solubility, delivery, etc., additions of polyethylene glycol groups, polypropylene glycol, etc., in the manner set forth in U.S. Pat. No. 4,640,835; 4,496,689; 4,301,144; 4,670,417; 4,791,192 or 4,179,337, each of which is hereby incorporated by reference. One type of covalent modification of the IL-12 molecule is introduced into the molecule by reacting targeted amino acid residues of the IL-12 polypeptide with an organic derivatizing agent that is capable of reacting with selected side chains or the N- or C-terminal residues of the IL-12 polypeptide. Other IL-12 variants included in the present invention are those where the canonical sequence has been altered to increase the glycosylation pattern of the resultant IL-12 molecule, as compared with the native, non-altered IL-12. This method has been used to generate second generation molecules of erythropoietin, referred to as Aranesp. Both native sequence IL-12 and amino acid sequence variants of IL-12 may be covalently modified. Also as referred to herein, the IL-12 molecule can be produced by various methods known in the art, including recombinant methods. Since it is often difficult to predict in advance the characteristics of a variant IL-12 polypeptide, it will be appreciated that some screening of the recovered variant will be needed to select the optimal variant. A preferred method of assessing a change in the properties of variant IL-12 molecules is via the lethal irradiation rescue protocol disclosed below. Other potential modifications of protein or polypeptide properties such as redox or thermal stability, hydrophobicity, susceptibility to proteolytic degradation, or the tendency to aggregate with carriers or into multimers are assayed by methods well known in the art.

Unless indicated otherwise, "about" means plus or minus 10% of the stated value.

The term "buffer" as used herein denotes a pharmaceutically acceptable excipient, which stabilizes the pH of a pharmaceutical preparation. Suitable buffers are well known in the art and can be found in the literature. Pharmaceutically acceptable buffers include but are not limited to histidine-buffers, citrate-buffers, succinate-buffers, acetate-buffers, phosphate-buffers, arginine-buffers or mixtures thereof. The abovementioned buffers are generally used in an amount of about 1 mM to about 100 mM, of about 5 mM to about 50 mM and of about 10-20 mM. The pH of the buffered solution can be at least 4.0, at least 4.5, at least 5.0, at least 5.5 or at least 6.0. The pH of the buffered solution can be less than 7.5, less than 7.0, or less than 6.5. The pH of the buffered solution can be about 4.0 to about 7.5, about 5.5 to about 7.5, about 5.0 to about 6.5, and about 5.5 to about 6.5 with an acid or a base known in the art, e.g. hydrochloric acid, acetic acid, phosphoric acid, sulfuric acid and citric acid, sodium hydroxide and potassium hydroxide. As used herein when describing pH, "about" means plus or minus 0.2 pH units.

The term "surfactant" as used herein denotes a pharmaceutically acceptable excipient which is used to protect protein formulations against mechanical stresses like agitation and shearing. Examples of pharmaceutically acceptable surfactants include polyoxyethylensorbitan fatty acid esters (sold under the trademark TWEEN), polyoxyethylene alkyl ethers (BRIJ), alkylphenylpolyoxyethylene ethers (sold under the trademark TRITON-X), polyoxyethylene-polyoxypropylene copolymer (poloxamer, sold under the trademark PLURONIC), and sodium dodecyl sulphate (SDS). Suitable surfactants include polyoxyethylenesorbitan-fatty acid esters such as polysorbate 20, (sold under the trademark TWEEN 20) and polysorbate 80 (sold under the trademark TWEEN 80). Suitable polyethylene-polypropylene copolymers are those sold under the names PLURONIC F68 or Poloxamer 188. Suitable Polyoxyethylene alkyl ethers are those sold under the trademark BRIJ. Suitable alkylphenolpolyoxyethylene ethers are sold under the tradename TRITON-X. When polysorbate 20 (TWEEN 20) and polysorbate 80 (TWEEN 80) are used they are generally used in a concentration range of about 0.001 to about 1%, of about 0.005 to about 0.2% and of about 0.01% to about 0.1% w/v (weight/volume).

The term "stabilizer" denotes a pharmaceutical acceptable excipient, which protects the active pharmaceutical ingredient and/or the formulation from chemical and/or physical degradation during manufacturing, storage and application. Chemical and physical degradation pathways of protein pharmaceuticals are reviewed by Cleland et al., *Crit. Rev. Ther. Drug Carrier Syst.*, 10(4):307-77 (1993); Wang, *Int. J. Pharm.*, 185(2):129-88 (1999); Wang, *Int. J. Pharm.*, 203 (1-2):1-60 (2000); and Chi et al., *Pharm. Res.*, 20(9):1325-36 (2003). Stabilizers include but are not limited to sugars, amino acids, polyols, cyclodextrines, e.g. hydroxypropyl-.beta.-cyclodextrine, sulfobutylethyl-.beta.-cyclodextrin, .beta.-cyclodextrin, polyethylenglycols, e.g. PEG 3000, PEG 3350, PEG 4000, PEG 6000, albumine, human serum albumin (HSA), bovine serum albumin (BSA), salts, e.g. sodium chloride, magnesium chloride, calcium chloride, chelators, e.g. EDTA as hereafter defined. As mentioned hereinabove, stabilizers can be present in the formulation in an amount of about 10 to about 500 mM, an amount of about 10 to about 300 mM, or in an amount of about 100 mM to about 300 mM.

The term "sugar" as used herein denotes a monosaccharide or an oligosaccharide. A monosaccharide is a monomeric carbohydrate which is not hydrolysable by acids, including simple sugars and their derivatives, e.g. amino sugars. Examples of monosaccharides include glucose, fructose, galactose, mannose, sorbose, ribose, deoxyribose, neuraminic acid. An oligosaccharide is a carbohydrate consisting of more than one monomeric saccharide unit connected via glycosidic bond(s) either branched or in a chain. The monomeric saccharide units within an oligosaccharide can be identical or different. Depending on the number of monomeric saccharide units the oligosaccharide is a di-, tri-, tetra- penta- and so forth saccharide. In contrast to polysaccharides the monosaccharides and oligosaccharides are water soluble. Examples of oligosaccharides include sucrose, trehalose, lactose, maltose and raffinose. Sugars can be present in the formulation at a concentration of greater than 0.1%, 0.5%, 1%, 2%, 3%, 4%, or 5%. Sugars can be present in the formulation at a concentration of less than 20%, 15%, 10%, 9%, 8%, 7%, or 6%. Sugars can be present in the formulation in an amount of about 6%, about 55 to about 7%, about 4 to about 8%, about 2% to about 10%, about 1% to about 10%, about 1% to about 20%, about 0.1% to about 10%, or about 0.1% to about 20%.

The term "polyols" as used herein denotes pharmaceutically acceptable alcohols with more than one hydroxy group. Suitable polyols comprise but are not limited to mannitol, sorbitol, glycerine, dextran, glycerol, arabitol, propylene glycol, polyethylene glycol, and combinations thereof. Polyols can be used in an amount of about 10 mM to about 500 mM, in an amount of about 10 to about 300 mM, or in an amount of about 100 to about 300 mM.

A subgroup within the stabilizers are lyoprotectants. The term "lyoprotectant" denotes pharmaceutical acceptable excipients, which protect the labile active ingredient (e.g., a protein) against destabilizing conditions during the lyophilisation process, subsequent storage and reconstitution. Lyoprotectants include but are not limited to the group consisting of sugars, polyols (such as e.g. sugar alcohols) and amino acids. Lyoprotectants included but art not limited to sugars such as sucrose, trehalose, lactose, glucose, mannose, maltose, galactose, fructose, sorbose, raffinose, neuraminic acid, amino sugars such as glucosamine, galactosamine, N-methylglucosamine ("Meglumine"), polyols such as mannitol and sorbitol, and amino acids such as arginine and glycine. Lyoprotectants are generally used in an amount of about 10 to 500 mM, in an amount of about 10 to about 300 mM, or in an amount of about 100 to about 300 mM.

A subgroup within the stabilizers are antioxidants. The term "antioxidant" denotes pharmaceutically acceptable excipients, which prevent oxidation of the active pharmaceutical ingredient. Antioxidants comprise but are not limited to ascorbic acid, glutathione, cysteine, methionine, citric acid, EDTA. Antioxidants can be used in an amount of about 1 to about 100 mM, in an amount of about 5 to about 50 mM, or in an amount of about 5 to about 20 mM.

The term "tonicity agents" as used herein denotes pharmaceutically acceptable tonicity agents. Tonicity agents are used to modulate the tonicity of the formulation. The formulation can be hypotonic, isotonic or hypertonic. Isotonicity in general relates to the osmotic pressure relative of a solution usually relative to that of human blood serum. The formulation according to the invention can be hypotonic, isotonic or hypertonic but will preferably be isotonic. An isotonic formulation is liquid or liquid reconstituted from a solid form, e.g., from a lyophilised form and denotes a solution having the same tonicity as some other solution with which it is compared, such as physiologic salt solution and the blood serum. Suitable tonicity agents comprise but are not limited to sodium chloride, potassium chloride, glycerine and any component from the group of amino acids, sugars, in particular glucose. Tonicity agents are generally used in an amount of about 5 mM to about 500 mM.

Within the stabilizers and tonicity agents there is a group of compounds which can function in both ways, i.e., they can at the same time be a stabilizer and a tonicity agent. Examples thereof can be found in the group of sugars, amino acids, polyols, cyclodextrines, polyethylenglycols and salts. An example of a sugar which can function as a stabilizer and a tonicity agent is trehalose.

The compositions described herein may also contain "adjuvants" such as preservatives, wetting agents, emulsifying agents and dispersing agents. Prevention of microorganism contamination may be ensured both by sterilization procedures, and by the inclusion of various antibacterial and antifungal agents, for example, paraben, chlorobutanol, phenol, sorbic acid, and the like. Preservatives are generally used in an amount of about 0.001 to about 2% (w/v). Preservatives comprise but are not limited to ethanol, benzyl alcohol, phenol, m-cresol, p-chlor-m-cresol, methyl or propyl parabens, and benzalkonium chloride.

The term "liquid" as used herein in connection with the formulation according to the invention denotes a formulation which is liquid at a temperature of at least about 2 to about 8° C. under atmospheric pressure.

The term "lyophilizate" as used herein in connection with the formulation according to the invention denotes a formulation which is manufactured by freeze-drying methods known in the art. In such a formulation, a solvent (e.g. water) is removed by freezing following sublimation under vacuum and desorption of residual water at elevated temperature. The lyophilisate has usually a residual moisture of about 0.1 to 5% (w/w) and is present as a powder or a physical stable cake. The lyophilizate is characterized by a fast dissolution after addition of a reconstitution medium.

The term "reconstituted formulation" as used herein in connection with the formulation according to the invention denotes a formulation which is lyophilized and re-dissolved by addition of reconstitution medium. Examples of reconstitution medium include but are not limited to water for injection (WFI), bacteriostatic water for injection (BWFI), sodium chloride solutions (e.g. 0.9% (w/v) NaCl), glucose solutions (e.g. 5% glucose), surfactant, containing solutions (e.g. 0.01% polysorbate 20), and a pH-buffered solution (e.g. phosphate-buffered solutions).

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion.

A "therapeutically effective amount or dose" or "sufficient amount or dose" as used herein includes a dose that produces effects for which it is administered, for example, a dose sufficient for increasing survival, and/or preserving bone marrow function, and/or promoting hematopoietic recovery or restoration in a subject that has been exposed to an acute dose of whole body ionizing radiation. The exact dose will depend on the purpose of the treatment and the timing of the IL-12 administration, certain characteristics of the subject to be treated, the total amount or timing of irradiation, and will be ascertainable by one skilled in the art using known techniques (see, e.g., Lieberman, *Pharmaceutical Dosage*

Forms (vols. 1-3, 1992); Lloyd, *The Art, Science and Technology of Pharmaceutical Compounding* (1999); Pickar, *Dosage Calculations* (1999); and *Remington: The Science and Practice of Pharmacy*, 20th Edition, 2003, Gennaro, Ed., Lippincott, Williams & Wilkins).

Generally, a dose of a therapeutic agent, according to the methods and compositions of the present invention, can be expressed in terms of the total amount of drug to be administered (i.e., ng, µg, or mg). Preferably, the dose can be expressed as a ratio of drug to be administered to weight or surface area of subject receiving the administration (i.e., ng/kg, µg/kg, ng/m$^2$, or mg/m$^2$). When referring to a dose in terms of the mass to be administered per mass of subject (i.e., ng/kg), it will be understood that doses are not equivalent between different animals, and thus conversion factors will need to be used to ensure that one animal receives the same dose equivalent as another animal. Suitable factors for the conversion of a mouse "dose equivalent" to a "dose equivalent" of a different animal are given in the look-up table below. Thus, in a preferred embodiment, doses are given in terms of mass to surface area (i.e., ng/m$^2$), which are equivalent for all animals. The following basic conversion factors can be used to convert ng/kg to ng/m$^2$: mouse=3.0, hamster=4.1, rat=6.0, guinea pig=7.7, human=38.0 (*Cancer Chemother Repts.*, 50(4):219 (1966)).

TABLE 1

Conversion factors and equivalent doses for several animals

| Species | Weight (kg) | Total Dose (ng) | Dose (ng/kg) | Dose (ng/m$^2$) | Conversion Factor |
|---|---|---|---|---|---|
| Human | 65 | 25655.82 | 394.7 | 15000 | 0.0794 |
| Mouse | 0.02 | 99.47 | 4973.44 | 15000 | 1.0000 |
| Hamster | 0.03 | 130.2 | 4339.87 | 15000 | 0.8726 |
| Rat | 0.15 | 381.12 | 2540.8 | 15000 | 0.5109 |
| Guinea Pig | 1.00 | 1335 | 1335 | 15000 | 0.2684 |
| Rabbit | 2 | 2381.1 | 1190.55 | 15000 | 0.2394 |
| Cat | 2.5 | 2956.44 | 1182.57 | 15000 | 0.2378 |
| Monkey | 3 | 3681.75 | 1227.25 | 15000 | 0.2468 |
| Dog | 8 | 6720 | 840 | 15000 | 0.1689 |

As used herein, the term "low dose" includes doses less than about 15 µg/m2, or less than about 14 µg/m2, or less than about 13 µg/m$^2$, 12 µg/m$^2$, 11 µg/m$^2$, 10 µg/m$^2$, 9 µg/m$^2$, 8 µg/m$^2$, 7 µg/m$^2$, 6 µg/m$^2$, 5 µg/m$^2$, 4 µg/m$^2$, 3 µg/m$^2$, 2 µg/m$^2$, 1 µg/m$^2$, or less than about 900 ng/m$^2$, 800 ng/m$^2$, 700 ng/m$^2$, 600 ng/m$^2$, 500 ng/m$^2$, 400 ng/m$^2$, 300 ng/m$^2$, 200 ng/m$^2$, or 100 ng/m$^2$.

As used herein, the term "ultralow dose" includes doses less than about 3 µg/m2, 2 µg/m2, 1 µg/m2, or less than about 900 ng/m2, 800 ng/m2, 700 ng/m2, 600 ng/m2, 500 ng/m2, 400 ng/m2, 300 ng/m2, 200 ng/m2, or 100 ng/m2.

"Near the time of administration of the treatment" refers to the administration of IL-12 at any reasonable time period either before and/or after the administration of the treatment, such as one month, three weeks, two weeks, one week, several days, one day, 20 hours, several hours, one hour or minutes. Near the time of administration of the treatment may also refer to either the simultaneous or near simultaneous administration of the treatment and IL-12, i.e., within minutes to one day.

"Disease state" refers to a condition present in a mammal whereby the health and well being of the mammal is compromised. In certain embodiments of the invention, treatments intended to target the disease state are administered to the mammal.

"A treatment" is intended to target the disease state and combat it, i.e., ameliorate the disease state. The particular treatment thus will depend on the disease state to be targeted and the current or future state of medicinal therapies and therapeutic approaches. A treatment may have associated toxicities.

"An associated hematopoietic toxicity" is a toxicity that substantially arises from the administration of the treatment to a mammal that adversely affects the hematopoietic system of the mammal. This adverse effect can be manifested in the mammal broadly whereby many hematopoietic cell types are altered from what is considered to be normal levels, as a result of the treatment, or as a result of the treatment and the disease state combined, or the adverse effect can be manifested in the mammal more specifically whereby only one or a few hematopoietic cell types are altered from what is considered to be normal levels, as a result of the treatment, or as a result of the treatment and the disease state combined.

"Chemotherapy" refers to any therapy that includes natural or synthetic agents now known or to be developed in the medical arts. Examples of chemotherapy include the numerous cancer drugs that are currently available. However, chemotherapy also includes any drug, natural or synthetic, that is intended to treat a disease state. In certain embodiments of the invention, chemotherapy may include the administration of several state of the art drugs intended to treat the disease state. Examples include combined chemotherapy with docetaxel, cisplatin, and 5-fluorouracil for patients with locally advanced squamous cell carcinoma of the head (Tsukuda et al., Int. J. Clin. Oncol., 9 (3):161-6 (June, 2004)), and fludarabine and bendamustine in refractory and relapsed indolent lymphoma (Konigsmann et al., Leuk Lymphoma., 45 (9): 1821-1827 (2004)).

"Radiation therapy" refers to any therapy where any form of radiation is used to treat the disease state. The instruments that produce the radiation for the radiation therapy are either those instruments currently available or to be available in the future.

"High dose treatment modalities" refer to treatments that are high sub-lethal or near lethal. High dose treatment modalities are intended to have an increased ability to combat a disease state, but generally possess increased associated toxicities. Further, generally high dose treatment modalities exhibit increased hematopoietic toxicities, as compared with conventional treatment modalities. The protocols for high dose treatment modalities are those currently used or to be used in the future.

"A dose dense treatment regimen" is generally a treatment regimen whereby the treatment is repeated sequentially in an accelerated manner to achieve the desired treatment outcome, as compared with conventional treatment regimens. The methods of the invention facilitate the use of dose dense treatment regimens by reducing or ameliorating the associated hematopoietic toxicities of the treatment, thereby permitting dose dense treatment regimens to be utilized and increasing the rate of success in treating a particular disease state. (see generally, Hudis et al., Semin. Oncol., 31 (3 Suppl 8): 19-26 (June, 2004); Keith et al., J. Clin. Oncol., 22 (4): 749 (Feb. 15, 2004); author reply 751-3; Maurel et al, Cancer, 100(7): 1498-506 (Apr. 1, 2004); Atkins C D, J. Clin. Oncol., 15; 22 (4): 749-50 (Feb. 15, 2004).)

"Chemoprotection or radioprotection" refers to protection from, or an apparent decrease in, the associated hematopoietic toxicity of a treatment intended to target the disease state.

"An increased remission" refers to a decrease, lessening, reduction, shrinking, diminution, or the like in one or more measurable parameters of a particular disease state.

"Solid tumors" generally refers to the presence of cancer of body tissues other than blood, bone marrow, or the lymphatic system.

"Hematopoietic disorders (cancers)" generally refers to the presence of cancerous cells originated from hematopoietic system.

As used herein, "anemia" refers to a group of hematological conditions associated with reduced levels of red blood cells or general hemoglobin deficiency. Examples of specific anemias include, without limitation, anemia of prematurity, aplastic anemia, fanconi anemia, hemolytic anemia, hereditary spherocytosis, sickle-cell anemia, warm autoimmune 20 hemolytic anemia, cold agglutinin hemolytic anemia, pernicious anemia, myelophthisic anemia or myelophthisis, and anemia of pregnancy. Generally, anemia may be caused by a disease or disorder, or develop in result of a therapy used to treat a disease or condition such as cancer. Non-limiting examples of causes of anemia include, iron deficiency, chronic disease (e.g. chronic infection, chronic immune activation, or malignancy), thalassemia, folic acid deficiency, hypothyroidism, macrocytosis, DNA replication inhibitors (e.g. methotrexate, zidovudine), acute blood loss, chemotherapy, radiation therapy, acute radiation exposure, and the like. Typical treatments for anemia include iron or folic acid supplementation, blood transfusion, administration of erythropoietin (EPO), and the like.

As used herein, "leukopenia" refers to a hematological condition associated with reduced levels of white blood cells. Generally, leukopenia may be caused by a disease or disorder, or develop in result of a therapy used to treat a disease or condition such as cancer or hepatitis C. Non-limiting examples of causes of leukopenia include, leukemia, myelofibrosis, aplastic anemia, influenza, systemic lupus erythematosus, Hodgkin's lymphoma, cancer, typhoid, malaria, tuberculosis, dengue, Rickettsial infections, enlargement 11 of the spleen, folate deficiencies, psittacosis, sepsis, mineral deficiencies, chemotherapy, radiation therapy, acute radiation exposure, certain medications, and the like. Examples of medications that may cause leukopenia include clozapine, immunosuppressive drugs, including sirolimus, mycophenolate mofetil, tacrolimus, and cyclosporine, interferon 5 treatments, such as Rebif, Avonex, and Betaseron, Wellbutrin, Minocycline, and the like. Common treatments for leukopenia include administration of granulocyte colony-stimulating factor (G-CSF) or granulocyte-macrophage colony-stimulating factor (GM-CSF).

As used herein, the term "neutropenia" refers to a hematological conditions associated with reduced levels of neutrophils. Generally, neutropenia may be caused by a 10 disease or disorder, or develop in result of a therapy used to treat a disease or condition such as cancer or hepatitis C. Non-limiting examples of causes of neutropenia include, aplastic anemia, cancer, blood cancer, congenital neutropenia, cyclic neutropenia, folate deficiency, autoimmune neutropenia, viral infection, hemodialysis, chemotherapy, radiation therapy, acute radiation exposure, administration of antiviral medications, and the like. In some 15 embodiments, neutropenia may comprise either acute or chronic neutropenia. One common treatment for neutropenia is administration of granulocyte colony-stimulating factor (G-CSF), such as recombinant G-CSF marketed under the brand name Neupogen®.

As used herein, "thrombocytopenia" refers to a group of hematological conditions associated with reduced levels of platelets. Generally, thrombocytopenia may be caused by a 20 disease or disorder, or develop in result of a therapy used to treat a disease or condition such as cancer. Non-limiting examples of causes of thrombocytopenia include, folic acid deficiency, leukemia or myelodysplastic syndrome, liver failure, sepsis, systemic viral or bacterial infection, dengue fever, various hereditary syndromes, congenital amegakaryocytic thrombocytopenia (CAMT), thrombocytopenia absent radius syndrome, Fanconi anemia, 25 Bernard-Soulier syndrome, May Hegglin anomaly, grey platelet syndrome, Alport syndrome, chemotherapy, radiation therapy, acute radiation exposure, idiopathic thrombocytopenic purpura (ITP), thrombotic thrombocytopenic purpura (TTP), hemolytic-uremic syndrome (HUS), disseminated intravascular coagulation (DIC), paroxysmal nocturnal hemoglobinuria (PNH), antiphospholipid syndrome, systemic lupus erythematosus (SLE), post transfusion 30 purpura, neonatal alloimmune thrombocytopenia (NAITP), hypersplenism, dengue fever, HIV-associated thrombocytopenia, various medications, such as valproic acid, methotrexate, carboplatin, interferon, isotretinoin, H2 blockers and proton pump inhibitors, and the like. Although drug treatments exist for certain subtypes of thrombocytopenia (i.e., ITP, TTP, 12 HIT), treatments for chronic thrombocytopenia are limited and typically include platelet transfusions or bone marrow/ step cell transplantation.

As used herein, "pancytopenia" refers to a hematological condition associated with a reduction in the levels of red blood cells, white blood cells, and platelets. A related 5 condition, bicytopenia, is associated with a reduction in the levels of two of these three cell types. Generally, pancytopenia may be caused by a disease or disorder, or develop in result of a therapy used to treat a disease or condition such as cancer. Specific examples of causes of pancytopenia include, without limitation, hypersplenism, myelofibrosis, aplastic anemia, the malignant form of osteoporosis, familial hemophagocytic syndrome, dyskeratosis 10 congenital, myelodysplastic syndrome, leukemia, leishmaniasis, severe folate or vitamin B12 deficiency, systemic lupus erythematosus, paroxysmal nocturnal hemoglobinuria, viral infections (HIV most common), alimentary toxic aleukia (ATA), copper deficiency, chemotherapy, radiation therapy, acute radiation exposure, and the like. Common treatments for pancytopenia include administration of G-CSF, GM-CSF, EPO, and bone marrow 15 transplants.

Acute Radiation Syndrome" in humans as used herein includes an acute radiation exposure of 2 Gy or greater.

Hematopoietic Syndrome" as used herein includes damage to the bone marrow compartment which results in pancytopenia, i.e., a deficiency in peripheral blood cell counts for all blood cell types, namely white blood cells, red blood cells and platelets. Hematopoietic Syndrome also refers to loss of hematopoietic progenitor and stem cells in the bone marrow compartment.

"Survival" as used herein includes an increase in survival that can be measured in non-human species as compared to control groups, such as mice or non-human primates.

Hematopoietic Recovery" as used herein includes early recovery of peripheral blood cell counts for white blood cells, red blood cells and platelets, as compared to control groups and as measured in non-human species, such as mice or non-human primates.

Preservation of bone marrow function" as used herein includes early recovery of cellularity or colony forming units in the bone marrow compartment, or any other measure of bone marrow function, as compared to control groups and as measured in non-human species, such as mice and non-human primates.

As used herein, the term "cancer" refers to mammalian cancers and carcinomas, for example, human, murine, rodent, and the like, leukemias, sarcomas, adenocarcinomas, 5 lymphomas, solid and lymphoid cancers, etc. Examples of different types of cancer include, but are not limited to, colon cancer, colorectal cancer, gastrointestinal cancer, esophageal squamous cell carcinoma or adenocarcinoma, gastric carcinoma, signet ring cell carcinoma, gastric lymphoma (MALT lymphoma), linitis plastica, duodenal cancer (e.g. adenocarcinoma), cancer of the appendix (e.g. carcinoid or pseudomyxoma peritonei), 10 colon/rectum colorectal polyps, familial adenomatous polyposis, colonic adenocarcinoma, familial adenomatous polyposis, hereditary nonpolyposis colorectal cancer, anal cancer, upper or lower gastrointestinal stromal tumors, Krukenberg tumor, liver hepatocellular carcinoma (e.g. fibrolamellar), hepatoblastoma, hepatocellular adenoma, focal nodular hyperplasia, nodular regenerative hyperplasia, biliary tract neoplasm, cholangiocarcinoma, 15 Klatskin tumor, gallbladder cancer, pancreas adenocarcinoma, pancreatic ductal carcinoma, pancreatoblastoma, primary peritoneal cancer, breast cancer, gastric cancer, bladder cancer, ovarian cancer, thyroid cancer, lung cancer, prostate cancer, uterine cancer, testicular cancer, neuroblastoma, squamous cell carcinoma of the head, neck, cervix and vagina, multiple myeloma, soft tissue and osteogenic sarcoma, liver cancer (i.e., hepatocarcinoma), renal 20 cancer (i.e., renal cell carcinoma), pleural cancer, pancreatic cancer, cervical cancer, anal cancer, bile duct cancer, gastrointestinal carcinoid tumors, esophageal cancer, gall bladder cancer, small intestine cancer, cancer of the central nervous system, skin cancer, choriocarcinoma; osteogenic sarcoma, fibrosarcoma, glioma, melanoma, B-cell lymphoma, non-Hodgkin's lymphoma, Burkitt's lymphoma, Small Cell lymphoma, Large Cell 25 lymphoma, monocytic leukemia, myelogenous leukemia, acute lymphocytic leukemia, and acute myelocytic leukemia, chronic myelocytic leukemia, promyelocytic leukemia, and the like.

"Ameliorate the deficiency" refers to a reduction in the hematopoietic deficiency, i.e., an improvement in the deficiency, or a restoration, partially or complete, of the normal state as defined by currently medical practice. Thus, amelioration of the hematopoitic deficiency refers to an increase in, a stimulation, an enhancement or promotion of, hematopoiesis generally or specifically. Amelioration of the hematopoietic deficiency can be observed to be general, i.e., to increase two or more hematopoietic cell types or lineages, or specific, i.e., to increase one hematopoietic cell type or lineages.

"Bone marrow cells" generally refers to cells that reside in and/or home to the bone marrow compartment of a mammal. Included in the term "bone marrow cells" is not only cells of hematopoietic origin, including but not limited to hematopoietic repopulating cells, hematopoietic stem cell and/or progenitor cells, but any cells that may be derived from bone marrow, such as endothelial cells, mesenchymal cells, bone cells, neural cells, supporting cells (stromal cells), including but not limited to the associated stem and/or progenitor cells for these and other cell types and lineages.

"Hematopoietic cell type" generally refers to differentiated hematopoietic cells of various types, but can also include the hematopoietic progenitor cells from which the particular hematopoietic cell types originate from, such as various blast cells referring to all the cell types related to blood cell production, including stem cells, progenitor cells, and various lineage cells, such as myeloid cells, lymphoid cell, etc.

"Hematopoietic cell lineage" generally refers to a particular lineage of differentiated hematopoietic cells, such as myeloid or lymphoid., but could also refer to more differentiated lineages such as dendritic, erythroid, etc.

"IL-12 facilitated proliferation" of cells refers to an increase, a stimulation, or an enhancement of hematopoiesis that at least partially attributed to an expansion, or increase, in cells that generally reside or home to the bone marrow of a mammal, such as hematopoietic progenitor and/or stem cells, but includes other cells that comprise the microenviroment of the bone marrow niche.

"Stimulation or enhancement of hematopoiesis" generally refers to an increase in one or more hematopoietic cell types or lineages, and especially relates to a stimulation or enhancement of one or more hematopoietic cell types or lineages in cases where a mammal has a deficiency in one or more hematopoietic cell types or lineages.

"Hematopoietic long-term repopulating cells" are generally the most primitive blood cells in the bone marrow; they are the blood stem cells that are responsible for providing life-long production of the various blood cell types and lineages.

"Hematopoietic stem cells" are generally the blood stem cells; there are two types: "long-term repopulating" as defined above, and "short-term repopulating" which can produce "progenitor cells" for a short period (weeks, months or even sometimes years depending on the mammal).

"Hematopoietic progenitor cells" are generally the first cells to differentiate from (i.e., mature from) blood stem cells; they then differentiate (mature) into the various blood cell types and lineages.

"Hematopoietic support cells" are the non-blood cells of the bone marrow; these cells provide "support" for blood cell production. These cells are also referred to as bone marrow stromal cells.

"Bone marrow preservation" means the process whereby bone marrow that has been damaged by radiation, chemotherapy, disease or toxins is maintained at its normal, or near normal, state; "bone marrow recovery" means the process whereby bone marrow that has been damaged by radiation, chemotherapy, disease or toxins is restored to its normal, near normal state, or where any measurable improvement in bone marrow function are obtained; bone marrow function is the process whereby appropriate levels of the various blood cell types or lineages are produced from the hematopoietic (blood) stem cells.

"Bone marrow failure" is the pathologic process where bone marrow that has been damaged by radiation, chemotherapy, disease or toxins is not able to be restored to normal and, therefore, fails to produce sufficient blood cells to maintain proper hematopoiesis in the mammal.

C. Hematopoietic Cell Production

Hematopoietic cell production is described generally in U.S. Pat. Nos. 5,968,513, 5,851,984 and 6,159,462. The morphologically recognizable and functionally capable cells circulating in blood include erythrocytes, macrophage or monocyte, neutrophilic, eosinophilic, and basophilic granulocytes, B-, T, non B-, non T-lymphocytes, and platelets. These mature hematopoietic cells derive from and are replaced, on demand, by morphologically recognizable dividing precursor cells for the respective lineages such as erythroblasts for the erythrocyte series, myeloblasts, promyelocytes and myelocytes for the monocyte/macrophage and granulocyte series, and megakaryocytes for the platelets.

The precursor cells derive from more primitive cells that can simplistically be divided into two major subgroups: stem cells and progenitor cells. The definitions of stem and progenitor cells are operational and depend on functional, rather than on morphological, criteria. Stem cells have extensive self-renewal or self-maintenance capacity, a necessity since an absence or depletion of these cells could result in the complete depletion of one or more cell lineages or cell types, events that would lead within a short time to disease and death. Some of the stem cells differentiate upon need, but some stem cells or their daughter cells produce other stem cells to maintain the precious pool of these cells. Thus, in addition to maintaining their own kind, pluripotential stem cells, or hemtopoietic repopulating cells, are capable of differentiation into several sub-lines of progenitor cells with more limited self-renewal capacity or no self-renewal capacity. These progenitor cells ultimately give rise to the morphologically recognizable precursor cells. The progenitor cells are capable of proliferating and differentiating along one, or more than one, of the myeloid differentiation pathways (Lajtha, L. G. (Rapporteur), Blood Cells, 5: 447 (1979)).

Additionally, chemotherapy and radiation therapy used in the treatment of cancer and certain immunological disorders can cause pancytopenias or combinations of anemia, neutropenia and thrombocytopenia. Thus, the increase or replacement of hematopoietic cells is often crucial to the success of such treatments. (For a general discussion of hematological disorders and their causes, see, e.g., "Hematology" in Scientific American Medicine, E. Rubenstein and D. Federman, eds., Volume 2, chapter 5, Scientific American, New York (1996)).

Furthermore, aplastic anemia presents a serious clinical condition as the overall mortality of all patients with aplastic anemias, in the absence of stem cell therapy, is high. Approximately 60-75% of individuals suffering from the disorder die within 12 months, in the absence of new stem cells. The overall incidence of these diseases is approximately 25 new cases per million persons per year. Although it is extremely unlikely that a single pathogenic mechanism accounts for all aplastic anemias, it is clear that provision of new hematopoietic stem cells is usually sufficient to allow permanent recovery, since transplantation of patients with aplastic anemia with bone marrow obtained from identical twins (i.e., syngeneic) (Pillow et al., N. Engl. J. Med., 275: 94-97 (1966)) or from HLA-identical siblings (i.e., allogeneic) (Thomas et al., The Lancet, pp. 284-289 (Feb. 5, 1972)) can fully correct the disease. However, some patients with aplastic anemia reject the transplanted marrow. This complication is particularly common among patients who have been immunologically sensitized as a result of multiple therapeutic blood transfusions.

The current therapy available for many hematological disorders as well as the destruction of the endogenous hematopoietic cells caused by chemotherapy or radiotherapy is bone marrow transplantation. However, use of bone marrow transplantation is severely restricted since it is extremely rare to have perfectly matched (genetically identical) donors, except in cases where an identical twin is available or where bone marrow cells of a patient in remission are stored in a viable frozen state. Except in such autologous cases, there is an inevitable genetic mismatch of some degree, which entails serious and sometimes lethal complications. These complications are two-fold. First, the patient is usually immunologically incapacitated by drugs beforehand, to avoid immune rejection of the foreign bone marrow cells (host versus graft reaction). Second, when and if the donated bone marrow cells become established, they can attack the patient (graft versus host disease), who is recognized as foreign. Even with closely matched family donors, these complications of partial mismatching are the cause of substantial mortality and morbidity directly due to bone marrow transplantation from a genetically different individual.

Peripheral blood has also been investigated as a source of repopulating cells, or stem cells for hematopoietic reconstitution (Nothdurtt et al., Scand. J. Haematol., 19: 470-481 (1977); Sarpel et al., Exp. Hematol., 7: 113-120 (1979); Ragharachar et al., J. Cell. Biochem., Suppl. 7A: 78 (1983); Juttner et al., Brit. J. Haematol., 61: 739-745 (1985); Abrams et al., J. Cell. Biochem., Suppl. 7A: 53 (1983); Prummer et al., Exp. Hematol., 13: 891-898 (1985)). In some studies, promising results have been obtained for patients with various leukemias (Reiffers et al., Exp. Hematol., 14: 312-315 (1986); Goldman et al., Br. J. Haematol., 45: 223-231 (1980); Tilly et al., The Lancet, pp. 154-155 (Jul. 19, 1986); see also To, L. B. and Juttner, C. A., Brit. J. Haematol., 66: 285-288 (1987), and references cited therein); and with lymphoma (Korbling et al., Blood, 67: 529-532 (1986)). Other studies using peripheral blood, however, have failed to effect reconstitution (Hershko et al., The Lancet, 1: 945-947 (1979); Ochs et al., Pediatr. Res., 15: 601 (1981). Studies have also investigated the use of fetal liver cell transplantation (Cain et al., Transplantation, 41: 32-25 (1986); Ochs et al., Pediatr. Res., 15: 601 (1981); Paige et al., J. Exp. Med., 153: 154-165 (1981); Touraine, J. L., Excerpta Med., 514: 277 (1980); Touraine, J. L., Birth Defects, 19: 139 (1983); see also Good et al., Cellular Immunol., 82: 44-45 (1983) and references cited therein) or neonatal spleen cell transplantation (Yunis et al., Proc. Natl. Acad. Sci. U.S.A., 72: 4100 (1974)) as stem cell sources for hematopoietic reconstitution. Cells of neonatal thymus have also been transplanted in immune reconstitution experiments (Vickery et al., J. Parasitol., 69(3): 478-485 (1983); Hirokawa et al., Clin. Immunol. Immunopathol., 22: 297-304 (1982)).

D. Interleukin-12 (IL-12)

For general descriptions relating to IL-12 see U.S. Pat. Nos. 5,573,764, 5,648,072, 5,648,467, 5,744,132, 5,756, 085, 5,853,714 and 6,683,046. Interleukin-12 (IL-12) is a heterodimeric cytokine generally described as a proinflammatory cytokine that regulates the activity of cells involved in the immune response (Fitz et al., J. Exp. Med., 170: 827-45 (1989)). Generally IL-12 stimulates the production of interferon-γ (INF-γ) from natural killer (NK) cells and T cells (Lertmemongkolchai et al., J. of Immunology, 166: 1097-105 (2001); Cui et al., Science, 278: 1623-6 (1997); Ohteki et al., J. Exp. Med., 189:1981-6 (1999); Airoldi et al., J. of Immunology, 165: 6880-8 (2000)), favors the differentiation of T helper 1 (TH1) cells (Hsieh et al., Science, 260: 547-9 (1993); Manetti et al., J. Exp. Med., 177: 1199-1204 (1993)), and forms a link between innate resistance and adaptive immunity. IL-12 has also been shown to inhibit cancer growth via its immuno-modulatory and anti-angiogenesis effects (Brunda et al., J. Exp. Med., 178: 1223-1230 (1993)); Noguchi et al., Proc. Natl. Acad. Sci. U.S.A., 93: 11798-11801 (1996); Giordano et al., J. Exp. Med., 194: 1195-1206 (2001); Colombo et al, Cytokine Growth factor, Rev., 13: 155-168 (2002); Yao et al., Blood, 96: 1900-1905 (2000)). IL-12 is produced mainly by dendritic cells (DC)

and phagocytes (macrophages and neutrophils) once they are activated by encountering pathogenic bacteria, fingi or intracellular parasites (Reis et al., *J. Exp. Med.,* 186: 1819-1829 (1997); Gazzinelli et al., *J. Immunol.,* 153: 2533-2543 (1994); Dalod et al., *J. Exp. Med.,* 195: 517-528 (2002)). The IL-12 receptor (IL-12 R) is expressed mainly by activated T cells and NK cells (Presky et al., *Proc. Natl. Acad. Sci. U.S.A.,* 93: 14002-14007 (1996); Wu et al., *Eur. J. Immunol.,* 26: 345-50 (1996)).

Generally the production of IL-12 stimulates the production of INF-γ, which, in turn, enhances the production of IL-12, thus forming a positive feedback loop. In in vitro systems, it has been reported that IL-12 can synergize with other cytokines (IL-3 and SCF for example) to stimulate the proliferation and differentiation of early hematopoietic progenitors (Jacobsen S E, et al., *J. Exp. Med.,* 2: 413-8 (1993); Ploemacher et al., *Leukemia,* 7: 1381-8 (1993); Hirao et al., *Stem Cells,* 13: 47-53 (1995)).

However, prior to the present invention, in vivo administration of IL-12 was observed to decrease peripheral blood cell counts and bone marrow hematopoiesis (Robertson et al., *Clinical Cancer Research,* 5: 9-16 (1999); Lenzi et al., *Clinical Cancer Research,* 8: 3686-95 (2002); Ryffel B., *Clin Immunol Immunopathol.,* 83: 18-20 (1997); Car et al., *The Toxicol. Pathol.,* 27: 58-63 (1999)). Using INF-γ receptor knockout mice, Eng et al. and Car et al. demonstrated that high dose IL-12 did not induce the commonly seen toxicity effect, i.e., there was no inhibition of hematopoiesis (Eng et al., *J. Exp Med.,* 181: 1893-8 (1995); Car et al., *American Journal of Pathology,* 147: 1693-707 (1995)). This observation suggests that the general phenomenon of IL-12 facilitated enhancement of differentiated hematopoietic cells, as reported previously, may be balanced in vivo by the production of INF-γ, which acts in a dominant myelosuppressive fashion.

Without being held to any particular theory, the inventors hypothesize that, in contrast to previous reports regarding the mechanistic pathway for IL-12 mediated proliferation of hematopoietic cells, when the hematopoietic system is compromised, as it is during chemotherapy or radiation therapy, or in the case of certain hematopoietic diseases and disorders that lead to one or more hematopoietic deficiencies, the Il-12 mediated pathway leading to the production of INF-γ may be altered. Thus, besides the low doses used in the examples disclosed herein, another possible mechanism for decreased hematopoietic side effects in embodiments of the invention is that when relatively low dose IL-112 is given to a mammal whose hematopoietic system is compromised, the IL-12/INF-γ positive feedback loop may be inhibited. Since INF-γ inhibits hematopoiesis and also appears to be the major cytokine responsible for toxicity, the interruption of INF-γ production may be one of the factors underlying the discovery by the inventors that administration of IL-12 provides a hematopoietic protective and recovery effect without apparent toxicity.

E. Therapeutic Methods of the Invention

The present invention relates to therapeutic methods for treating diseases and disorders in which increased amounts of hematopoietic cells are desirable (e.g., diseases or disorders associated with reduced numbers of one or more hematopoietic cell types or lineages, or diseases where the recommended therapy has associated hematopoietic toxicities, thus leading to reduced numbers of one or more hematopoietic cell types or lineages, such as cancer) by administration of IL-12, derivatives and analogs thereof.

Thus, embodiments of the invention provide for methods of alleviating or treating various hematopoietic cell deficiencies, including deficiencies in hematopoietic repopulating cells, progenitor and stem cells, as well as general bone marrow deficiencies, by the direct administration of IL-12 to a mammal, as disclosed herein.

In the first embodiment of the invention, methods are disclosed for treating a disease state in a mammal by administering a treatment to the mammal that is intended to target the disease state, where the treatment has an associated hematopoietic toxicity, in conjunction with the administration of one or more therapeutically effective dose(s) of IL-12 near the time of administration of the treatment. One effect of the administration of IL-12 to the mammal in this embodiment of the invention is reduction of the hematopoietic toxicity of the treatment, thus permitting high-dose and dose dense protocols to be utilized in designed a particular patient's therapeutic regimen.

In an embodiment of the invention, methods are disclosed for administration of IL-12 directly to a mammal, preferably a human, suffering from a disease or disorder amenable to treatment by increasing production of one or more hematopoietic cell types (e.g., a disease or disorder associated with a hematopoietic cell deficiency). In a third embodiment of the invention, methods of stimulating hematopoiesis in a mammal in need comprising administering one or more therapeutically effective dose(s) of IL-12 for a duration to achieve a therapeutic effect that includes the stimulation of hematopoiesis, wherein the stimulation of hematoapoiesis involves the IL-12 facilitated proliferation of hematopoietic repopulating cells, hematopoietic progenitor cells or hematopoietic stem cells. In a fourth embodiment of the invention, methods are disclosed for bone marrow preservation or recovery in a mammal by administering one or more therapeutically effective dose(s) of IL-12 to the mammal, without the use of bone marrow cells, hematopoietic progenitor cells or hematopoietic stem cells, for a duration necessary for bone marrow preservation or recovery.

A further aspect of certain embodiments of the invention is that the use of IL-12 as an adjuvant or ancillary therapy to alleviate the hematopoietic toxicities associated with various forms of radiation and chemotherapy, permits high-dose and dose dense treatment protocols to be utilized, and thus, achieve greater rates of remission of the particular disease state and overall patient survival.

A particular embodiment of the invention provide for methods of treating a disease state in a mammal. In this embodiment, the disease state can be any disease state that is treated with either any chemotherapy or radiation therapy, or both. In the invention, the combined use of chemotherapeutic agents is preferred, as this clinical protocol is generally thought to be more therapeutically effective.

These methods generally include administering a treatment to the mammal that is intended to target the disease state. In this embodiment, the treatment, which is intended to combat the disease state, also has an associated hematopoietic toxicity. A second component in this embodiment of the invention includes administering a therapeutically effective dose of IL-12 near the time of administration of the treatment. IL-12 can be administered at any point in time near the administration of the treatment that yields the desired therapeutic effect. An overall benefit of practicing this embodiment of the invention is that the administration of IL-12 to the mammal reduces or decreases the hematopoietic toxicity of the treatment, and as a consequence alters the limiting toxic dosage of the various treatment modalities.

In these embodiments, the methods generally involve administering a primary therapeutic to a mammal, along with a secondary therapeutic in the form of IL-112, where the secondary therapeutic, i.e., IL-12 enhances hematopoiesis or improves hematopoietic recovery as compared with the administration of the primary therapeutic alone. The preferred mammal in this embodiment of the invention is a human.

The treatment that is intended to target the disease state can be any currently practiced therapy, or any therapy to be developed that uses either chemotherapy or radiation therapy, or a combined therapy, to attempt to combat the disease state. In the invention, chemotherapy involves the administration of chemical agents, which can be natural or synthetic agent that are provided in any chemical state, e.g. monomer to highly polymeric species. In the invention, radiation therapy includes the administration of relatively high energy wavelengths of light or high energy particles to the mammal as the treatment modality. For either chemotherapy or radiation therapy, high dose therapeutic approaches and dose dense protocols as currently practiced or to be developed in the future can be used in the embodiments of the present invention.

In general, disorders that can be treated by methods of the invention include, but are not limited to, four broad categories. First are diseases resulting from a failure or dysfunction of normal blood cell production and maturation (i.e., aplastic anemia, cytopenias and hypoproliferative stem cell disorders). The second group are neoplastic, malignant diseases in the hematopoietic organs (e.g., leukemia and lymphomas). The third group of disorders comprises those of patients with a broad spectrum of malignant solid tumors of non-hematopoietic origin. Induction of hematopoietic cell proliferation in these patients serves as a bone marrow rescue procedure, without the use of a cellular transplant, which is provided to a patient as an adjuvant therapy to chemotherapy and/or radiation therapy, including otherwise lethal chemotherapy or radiation therapy and dose dense therapeutic protocols. The fourth group of diseases consists of autoimmune conditions, where the enhancement or stimulation of hematopoiesis, leading to increases in hematopoietic cells, can serve as a source of replacement of an abnormal immune system. Particular diseases and disorders which can be treated by induction of hematopoietic cell production in vivo are not limited to those listed in Table 2, and described infra.

TABLE 2

DISEASE STATES OR DISORDERS WHICH CAN BE TREATED BY INCREASING HEMATOPOIESIS

I. Diseases resulting from a failure or dysfunction
of normal blood cell production and maturation hypoproliferative stem cell disorders
hyperproliferative stem cell disorders
aplastic anemia
neutropenia
cytopenia
anemia
pancytopenia
agranulocytosis
thrombocytopenia
red cell aplasia
Blackfan-Diamond syndrome
due to drugs, radiation, or infection
II. Hematopoietic malignancies acute lymphoblastic (lymphocytic) leukemia
chronic lymphocytic leukemia TABLE 2-continued

DISEASE STATES OR DISORDERS WHICH CAN BE TREATED BY INCREASING HEMATOPOIESIS acute myelogenous leukemia
chronic myelogenous leukemia
acute malignant myelosclerosis
multiple myeloma
polycythemia vera
angiogenic myelometaplasia
Waldenstrom's macroglobulinemia
Hodgkin's lymphoma
non-Hodgkin's lymphoma
III. Immunosuppression in subjects with malignant, solid tumors malignant melanoma
non-small cell lung cancer
carcinoma of the stomach
ovarian carcinoma
breast carcinoma
small cell lung carcinoma
retinoblastoma
testicular carcinoma
glioblastoma
rhabdomyosarcoma
neuroblastoma
Ewing's sarcoma
Lymphoma
IV. Autoimmune diseases rheumatoid arthritis
diabetes type I
chronic hepatitis
multiple sclerosis
systemic lupus erythematosus
V. Genetic (congenital) disorders anemias
familial aplastic anemias
Fanconi's syndrome
Bloom's syndrome
pure red cell aplasia (PRCA)
dyskeratosis congenita
Blackfan-Diamond syndrome
congenital dyserythropoietic syndromes I-IV
Shwachmann-Diamond syndrome
dihydrofolate reductase deficiencies
formamino transferase deficiency
Lesch-Nyhan syndrome
congenital spherocytosis
congenital elliptocytosis
congenital stomatocytosis
congenital Rh null disease
paroxysmal nocturnal hemoglobinuria
G6PD (glucose-6-phosphate dehydrogenase) variants 1, 2, 3
pyruvate kinase deficiency
congenital erythropoietin sensitivity deficiency
sickle cell disease and trait
thalassemia alpha, beta, gamma
met-hemoglobinemia
congenital disorders of immunity
severe combined immunodeficiency disease (SCID)
barelymphocyte syndrome
ionophore-responsive combined immunodeficiency
combined immunodeficiency with a capping abnormality
nucleoside phosphorylase deficiency
granulocyte actin deficiency
infantile agranulocytosis
Gaucher's disease
adenosine deaminase deficiency
Kostmann's syndrome
reticular dysgenesis
congenital leukocyte dysfunction syndromes
VI. Others osteopetrosis
myelosclerosis
acquired hemolytic anemias
acquired immunodeficiencies
infectious disorders causing primary or secondary immunodeficiency

TABLE 2-continued

DISEASE STATES OR DISORDERS WHICH CAN BE TREATED BY INCREASING HEMATOPOIESIS bacterial infections (e.g. Brucellosis, Listeriosis, tuberculosis, leprosy)
parasitic infections (e.g. malaria, Leishmaniasis)
fungal infections
disorders involving disproportions in lymphoid cell sets and impaired immune functions due to aging
phagocyte disorders
Kostmann's agranulocytosis
chronic granulomatous disease
Chediak-Higachi syndrome
Willams-Beuren syndrome
neutrophil actin deficiency
neutrophil membrane GP-180 deficiency
metabolic storage diseases
mucopolysaccharidoses
mucolipidoses
miscellaneous disorders involving immune mechanisms
Wiskott-Aldrich Syndrome
alpha 1-antitrypsin deficiency In a preferred embodiment of the invention, IL-12 administration in accordance with the methods of the invention is used to treat a disease resulting from a failure or dysfunction of normal blood cell production and maturation, such as an aplastic anemia, a cytopenia or a hypoproliferative stem cell disorder. These disorders entail failure of stem cells in bone marrow to provide normal numbers of functional blood cells. The aplastic anemias result from the failure of stem cells to give rise to the intermediate and mature forms of red cells, white cells, and platelets. While red cell production is usually most seriously affected, a marked decrease in production of other mature blood cell elements is also seen as some anemias specifically affect production of white cells and/or platelets. The large majority of these anemias are acquired during adult life, and do not have any apparent genetic predisposition. About half of these acquired anemias arise in the absence of any obvious causative factor such as exposure to poisons, drugs or disease processes that impair stem cell function; these are termed idiopathic aplastic anemias. The remaining cases are associated with exposure to an extremely diverse array of chemicals and drugs and also occur as the consequence of viral infections and after pregnancy. Other specific types of aplastic anemia are termed agranulocytosis or thrombocytopenia to indicate that the major deficiency lies in particular white cells or in platelet production, respectively. Additionally, agranulocytosis may be associated with autoimmune syndromes such as systemic lupus erythematosus (SLE) or with other infections, such as neonatal rubella.

In addition, immune deficiencies which are the primary or secondary result of infection by pathogenic microorganisms can be treated by administration of 11-12 according to the methods disclosed in the present invention. Microorganisms causing immune deficiencies which may be treated according to this embodiment of the invention include but are not limited to gram-negative bacilli such as *Brucella* or *Listeria*, the mycobacterium which are the etiological agents of tuberculosis or of Hansen's disease (leprosy), parasites such as *Plasmodium* (the etiological agents of malaria) or *Leishmania*, and fuigi (such as those that cause pneumonia and other lethal infections secondary to immunodeficiencies) (for a discussion of many of these disorders, see *Harrison's Principles of Internal Medicine,* 6th Edition, Wintrobe et al., eds., McGraw-Hill, New York, pp. 798-1044 (1970)).

In another aspect of the invention, methods are provided for increasing survival in a subject, and/or preserving bone marrow function, and/or promoting hematopoietic recovery or restoration comprising the administration of one or more dose of IL-12 to a subject at protracted times following acute exposure to non-therapeutic whole body ionizing radiation, wherein supportive care is given to said subject simultaneously or following administration of IL-12.

Also of significance is the demonstration that exogenous administration of IL-12 can expand long-term repopulating (LTR) hematopoietic stem cells (HSC) in vivo. Thus, without being bound by theory, HSC expansion by exogenous IL-12 can be the mechanism responsible for survival from hematopoietic injury resulting from lethal radiation exposure at later time points, e.g., 24 hours post-irradiation. Another potential mechanism relates to the ability of IL-12 to induce DNA repair and reduce apoptosis in hematopoietic stem cells (HSC) following radiation exposure.

While most bone marrow progenitor and stem cells are susceptible to cell death after high dose radiation, subpopulations of HSC or accessory cells are selectively more radioresistant, presumably because these cells exist in a largely noncycling (GO) state. In humans, these radioresistant cells can play an important role in recovery of hematopoiesis after exposure to doses as high as 6 Gy, albeit with a reduced capacity for self-renewal in the absence of exogenous IL-12.

Another determinant for hematopoietic reconstitution is non-homogeneity of the radiation dose, which can spare some marrow sites that then become the foci of hematopoietic activity. In either case, i.e., either the residual presence of radioresistant HSC or inhomogeneity of the radiation dose, the present findings indicate that a subpopulation of HSC marked by the presence of the IL-12 receptor (IL-12R+) survives and persists after high dose radiation, and moreover, that this IL-12R+HSC subpopulation is activated, expanded, and/or induced to repair itself upon exogenous administration of IL-12.

Following radiation exposure, it has been discovered that IL-12 is effective in mitigating the hematopoietic syndrome associated with acute radiation syndrome. Specifically, embodiments of the present invention provide methods for increasing survival, and/or preserving bone marrow function, and/or promoting hematopoietic recovery by administering one or more effective dose(s) of IL-12 to a subject following acute exposure to ionizing radiation.

1. Supportive Care

Supportive care modalities useful in conjunction with IL-12 for treatment of a subject who has been exposed to an acute dose of whole body ionizing radiation include, without limitation, administration of fluids, one or more antibiotic, blood or blood component transfusions, administration of one or more growth factors or hematopoietic growth factors, combination therapies and the like.

In one embodiment, supportive care comprises the administration of one or more antibiotics. Antibiotic support can be any antibiotic that is useful in preventing infections during periods of low blood cell counts including, without limitation, bactrim, ciprofloxacin, moxifloxacin, and the like. Those of skill in the art will know of other antibiotics useful for supportive care.

In another embodiment, supportive care comprises administration of one or more growth factors, including hematopoietic growth factors. Many suitable hematopoietic growth factors are known in the art including, without limitation, colony stimulating factors (CSF, G-CSF, GM-CSF, M-CSF, IL-3), erythropoietin, IL-1, IL-4, IL-5, IL-6, IL-7, IL-11, and the like. Several FDA-approved hematopoietic growth factors are currently available, and thus may be used in the methods provided herein, such as G-CSF (Neupogen or Neulasta), IL-11, and erythropoietin (Epogen, Procrit or Aranesp). In some embodiments, supportive care comprises the administration of keratinocyte growth factor (KGF or FGF7).

In one particular embodiment, erythropoietin administration can increase survival up to about 50% over and above that of IL-12 alone when super-lethal doses are used with no other supportive care measures, such as antibiotic support or fluids. Super-lethal doses are defined herein as radiation doses at or above 5.5 Gy. Erythropoietin is available as a FDA-approved recombinant protein drug for human use, such as Epogen, Procrit or Aranesp. Generally, dosing with these erythropoietin drugs will be simultaneous with or following the administration of IL-12. Erythropoietin drugs can be repeated as needed, but generally not administered more than every other day, or every third day. Preferably erythropoietin is administered about 48 hours after the last dose of IL-12.

An effective dose of erythropoietin for a human can be about 20 mg/kg, however, lower doses and higher doses are also effective in increasing survival when use as an adjuvant to IL-12 administration. Accordingly, in certain embodiments, erythropoietin is administered at about 1 mg/kg, or at about 2 mg/kg, 3 mg/kg, 4 mg/kg, 5 mg/kg, 10 mg/kg, 15 mg/kg, 20 mg/kg, 25 mg/kg, 30 mg/kg, 40 mg/kg, 50 mg/kg, or more for treatment in a human, or at a dose equivalent amount for treatment in an animal other than a human.

In another embodiment, supportive care comprises the administration of a blood transfusion. As used herein, a blood transfusion may encompass a whole blood transfusion, or alternatively, transfusion of a blood fraction or blood component, for example, a red blood cell transfusion, a platelet transfusion, a white blood cell transfusion. In a related embodiment, supportive care may comprise the administration of a bone marrow or bone marrow stem cell transplant.

For humans, as shown in Table 3, the early signs of hematopoietic syndrome start to occur in the range of radiation doses of 2 Gy or greater. Similarly, at radiation doses between about 5.5-7.5 Gy, pancytopenia and moderate GI damage occurs in humans. Advantageously, when administered according to the methods of the present invention, IL-12 is effective in alleviating the pancytopenia at these radiation dose levels, preserving bone marrow function and will not induce further GI damage. However, the radiation dose rate can also affect the relative level of radiation injury. Thus, two radiation doses given at two different dose rates can show differences in the severity of the relative radiation injury.

TABLE 3

Phases of Radiation Injury*

| Dose Range Gy | Severity | Manifestation of Illness | Prognosis (without Therapy) |
|---|---|---|---|
| 0.5-1.0 | Mild | Slight decrease in blood cell counts | Almost certain survival |
| 1.0-2.0 | Mild to moderate | Early signs of bone marrow damage | Highly probable survival (>90% of victims) |
| 2.0-3.5 | Moderate | Moderate to severe bone marrow damage | Probable survival |
| 3.5-5.5 | Severe | Severe bone marrow damage, slight GI damage | Death within 3.5-6 wk (50% of victims) |
| 5.5-7.5 | Severe | Pancytopenia and moderate GI damage | Death probable within 2-3 wk |
| 7.5-10.0 | Severe | Marked GI and bone marrow damage, hypotension | Death probable within 1-2.5 wk |
| 10.0-20.0 | Severe | Severe GI damage, pneuomonitis, altered mental status, cognitive dysfunction | Death certain within 5-12 d |
| 20.0-30.0 | Severe | Cerebrovascular collapse, fever, shock | Death certain within 2-5 d |

*Modified from Walker RI, Cerveny RJ, eds. (21), GI = gastrointestinal

For other mammals embraced by the methods and compositions of the present invention, for example mice, rats, guinea pigs, hamsters, cats, dogs, cattle, horses, sheep, pigs, rabbits, deer, monkeys, and the like, the radiation dose that can induce hematopoietic syndrome varies with the species and strain. For example, for rhesus monkeys, the LD50 is about 7 Gy. For certain strains of mice, the LD50 is also about 7 Gy, for example Balb-c mice. For other strains of mice, such as C57BL6, the LD50 is about 7.5 Gy. The LD50 can also exhibit differences based on gender or general health status of the animal.

Although it would be difficult to determine the exact extent of radiation injury in an mammal exposed to acute ionizing radiation following a radiation-related disaster, IL-12, when used in accordance with embodiments of the present invention, will increase survival, and/or preserve bone marrow function, and/or promote hematopoietic recovery of peripheral blood cell counts.

Accordingly, in some embodiments of the present invention, IL-12 is administered to a subject that has been exposed to an acute dose of ionizing radiation of at least about 1.0 Gy, or an amount equivalent to an LD10 in humans. In another embodiment, IL-12 is administered to a subject that has been exposed to about 3.5 Gy of ionizing radiation, or a dose equivalent to about LD50 in humans. In yet other embodiments, IL-12 is useful for increasing survival, and/or preserving bone marrow function, and/or promoting hematopoietic recovery of peripheral blood cell counts in a subject exposed to at least about 2.0 Gy, or at least about 3.0 Gy, 4.0 Gy, 5.0 Gy, 6.0 Gy, 7.0 Gy, 8.0 Gy, 9.0 Gy, 10.0 Gy, 11.0 Gy, 12.0 Gy, 13.0 Gy, 14.0 Gy, 15.0 Gy, 20.0 Gy, 25.0 Gy, 30.0 Gy, or higher doses of acute ionizing radiation. Similarly, the dose of ionizing radiation can be expressed in terms of the percent lethal dose, for example, a dose equivalent of about LD1, LD5, LD10, LD20, LD30, LD40, LD50, LD60, LD70, LD80, LD90, LD95, LD99, or LD100.

2. Treatment of Malignancies

Both chemotherapy and radiation therapy, which are used, either singly or together, to combat various forms of cancer, and other disease states, are toxic to an individual's hematopoietic system. Thus, for individuals treated with chemotherapy, radiation therapy, or a combination of these two therapeutic modalities, the individual's blood supply can be substantially depleted. Moreover, this depletion of the blood supply is generally a limiting factor in the use of chemotherapy and/or radiation therapy to combat various cancers and other disease states, and therefore generally precludes the use of high dose or dose dense treatment regimens.

Previously, IL-12 has been reported to play a pivotal role as an immuno-modulator, and has previously been shown to inhibit tumor growth in mice, IL-12 h as been tested in phase I and II human clinical trials for its potential to stimulate an immune response in cancer therapy (Eng et al., *Journal of Experimental Medicine,* 181: 1893-8; Car et al., *American Journal of Pathology,* 147: 1693-707). One of the common side effects of IL-12 therapy, however, is a transient decrease in blood cell counts: lymphopenia is common (Eng et al., *Journal of Experimental Medicine,* 181: 1893-8; Car et al., *American Journal of Pathology,* 147: 1693-707). In animal toxicity studies, lymphopenia is also a common side effect (Neta et al., *J. Immunol.,* 153: 4230-7; Hayes et al., *Blood,* 91: 4645-4651).

In contrast to previous studies, however, the inventors have made the discovery that when IL-12 is administered during certain time "windows" in relation to the time of a primary therapy, such as chemotherapy or radiation therapy, administration of IL-12 increases the nadir of blood cell counts broadly, i.e., increases blood cell counts, without any observable toxic effects of the IL-12 administration.

Thus, the therapeutic methods of the present invention can promote hematopoiesis in general, and in particular, promote hematopoiesis in an individual who has undergone, is undergoing, or will undergo chemotherapy and/or radiation therapy as treatment regimens that target the particular malignancies. Thus, in the particular embodiments of the invention, IL-12 administration is used as an adjuvant or ancillary therapy to one or more primary therapies implemented near the time of administration of the primary therapy. Thus, the present invention enhances hematopoietic recovery, as well as the general recovery, of a subject undergoing one or more therapies that incidentally decreases the individual's blood supply. As used herein, the term "undergoing" encompasses the implementation of a primary therapy before, during and/or after the implementation of the ancillary therapy of the present invention.

Among the individual-derived benefits that are a consequence of using the methods of the present invention as an adjuvant or ancillary therapy to chemotherapy and/or radiation therapy is a decrease in the toxic side effects of these primary therapeutic modalities, as well as enhanced recovery from these toxic side effects. These toxic side effects include depletion of one or more blood components of the subject's hematopoietic system. A particular individual-derived benefit of administering the methods of the present invention is that more aggressive primary treatment modalities can be used to combat the targeted disease state. Thus, the use of the methods of the present invention as an adjuvant or ancillary therapy allows the primary therapy to be administered in a dose dense treatment modality or high dose modality. In turn, the likelihood of success of the primary therapy is substantially increased when therapeutic compositions including IL-12 are administered as an ancillary therapy or combination therapy along with traditional therapeutic modalities. Another use of the therapeutic methods of the present invention is in the treatment of bone marrow failure resulting from certain disease states or is induced by the use of certain treatment modalities, such as aggressive chemotherapy and/or radiation therapy.

Hyperproliferative malignant stem cell disorders as well as non-hematopoietic malignancies can be treated with chemotherapy and/or radiation therapy along with rescue of hematopoietic cells by direct administration IL-12 as disclosed herein. The conditions that can be treated according to the invention include, but are not limited to, the leukemias listed in Table 2 and the solid tumors listed in Table 2.

These malignancies are currently treated by, inter alia, chemotherapy and/or radiation therapy, when feasible, allogeneic bone marrow transplantation. However, allogeneic HLA identical sibling bone marrow is available only to less than one-third of patients, and this treatment is associated with transplantation-related complications such as immuno-deficiency and graft versus host disease. Induction of hematopoietic cell proliferation in vivo via the methods of the invention permits hematopoietic reconstitution of patients lacking suitable allogeneic donors, or in the case of an autologous transplant, eliminates the risk of reintroduction of malignant cells. Thus, the methods of the invention can be administered to a patient who has undergone chemotherapy and/or radiation therapy for treatment of cancer or an immunological disorder. Also included in this embodiment of the invention is the use of administration of IL-12 as an adjuvant therapy to the various therapies used to treat infection, such as HAART therapy and/or radiation therapy, such as total lymphoid irradiation described below.

3. Autoimmune Disorders

Many chronic inflammatory and degenerative diseases are characterized by a continuous immune reaction against the body's own tissues. Such autoimmune disorders include but are not limited to rheumatoid arthritis and other inflammatory osteopathies, diabetes type I, chronic hepatitis, multiple sclerosis, and systemic lupus erythematosus. Autoimmune disorders are often treated by lymphoid irradiation. Administration of 11-12 as disclosed herein can be valuable to repopulate the hematopoietic system after radiotherapy.

Anti-inflammatory drugs such as steroids retard the inflammatory cells which are activated by autoreactive T cells, but do not prevent T cells which recognize self-proteins from activating new inflammatory cells. A more direct approach to treating autoimmune diseases depends on eradication of T cells by irradiation of the lymphoid tissues, and relying on stem cells from the unirradiated bone marrow to repopulate the patient's hematopoietic system. The rationale is that the formation of new populations of mature T cells from bone marrow stem cells may result in absence of T cells that have reactivity to self-specific antigens. This procedure, called total lymphoid irradiation (TLI), has been used to treat intractable rheumatoid arthritis (Strober et al., *Annals of Internal Medicine,* 102: 441-449, 450-458 (1985)). These clinical trials showed that in the majority of otherwise intractable cases, joint disease was significantly alleviated for at least 2-3 years. However, the major drawback to such treatment is failure of stem cells in the bone marrow of these elderly patients to efficiently repopulate the hematopoietic system, resulting in infections and bleeding disorders. Analogous studies have been made of the effects of TLI as an alternative to cytotoxic drugs for treatment of SLE (Strober et al., *Ann. Internal Med.,* 102: 450 (1985)). Studies of the use of TLI to treat intractable SLE have also shown that this treatment alleviates disease activity, but is severely limited by failure of bone marrow stem cells to rapidly and efficiently repopulate the hematopoietic system after irradiation. Thus, the therapeutic methods of the invention can be administered to promote proliferation of the remaining hematopoietic cells to increase the success of TLI therapy.

4. Methods of Administration of IL-12

The invention provides methods of treatment by administration to a subject of one or more effective dose(s) of IL-12 for a duration to achieve the desired therapeutic effect. The subject is preferably a mammal, including, but not limited to, animals such as cows, pigs, horses, chickens, cats, dogs, etc., and is most preferably human.

Various delivery systems are known and can be used to administer IL-12 in accordance with the methods of the invention, e.g., encapsulation in liposomes, microparticles, microcapsules, recombinant cells capable of expressing IL-12, receptor-mediated endocytosis (see e.g., Wu and Wu, *J. Biol. Chem.*, 262: 4429-4432 (1987)), construction of nucleic acid comprising a gene for IL-12 as part of a retroviral or other vector, etc. Methods of introduction include but are not limited to intradermal, intramuscular, intraperitoneal, intravenous, subcutaneous, intranasal, epidural, and oral routes.

In accordance with the methods of the invention, IL-12 can be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local. In addition, it may be desirable to introduce pharmaceutical compositions comprising IL-12 into the central nervous system by any suitable route, including intraventricular and intrathecal injection; intraventricular injection may be facilitated by an intraventricular catheter, for example, attached to a reservoir, such as an Ommaya reservoir. Pulmonary administration can also be employed, e.g., by use of an inhaler or nebulizer, and formulation with an aerosolizing agent. It may be desirable to administer the pharmaceutical compositions comprising IL-12 locally to the area in need of treatment; this may be achieved, for example and not by way of limitation, by topical application, by injection, by means of a catheter, by means of a suppository, or by means of an implant, said implant being of a porous, non-porous, or gelatinous material, including membranes, such as sialastic membranes, or fibers.

Other modes of IL-12 administration involve delivery in a vesicle, in particular a liposome (see Langer, *Science*, 249: 1527-1533 (1990); Treat et al., in *Liposomes in the Therapy of Infectious Disease and Cancer*, Lopez-Berestein and Fidler (eds.), Liss, New York, pp. 353-365 (1989); Lopez-Berestein, ibid., pp. 317-327; see generally ibid.)

Still other modes of administration of IL-12 involve delivery in a controlled release system. In certain embodiments, a pump may be used (see Langer, supra; Sefton, *CRC Crit. Ref. Biomed. Eng.*, 14: 201 (1987); Buchwald et al., *Surgery*, 88: 507 (1980); Saudek et al., *N. Engl. J. Med.*, 321: 574 (1989)). Additionally polymeric materials can be used (see Medical Applications of Controlled Release, Langer and Wise (eds.), CRC Pres, Boca Raton, Fla. (1974); Controlled Drug Bioavailability, Drug Product Design and Performance, Smolen and Ball (eds.), Wiley, N.Y. (1984); Ranger and Peppas, *J. Macromol. Sci. Rev. Macromol. Chem.*, 23: 61 (1983); see also Levy et al., *Science*, 228: 190 (1985); During et al., *Ann. Neurol.*, 25: 351 (1989); Howard et al., *J. Neurosurg.*, 71: 105 (1989)), or a controlled release system can be placed in proximity of the therapeutic target, i.e., the brain, thus requiring only a fraction of the systemic dose (see, e.g., Goodson, in Medical Applications of Controlled Release, supra, vol. 2, pp. 115-138 (1984)). Other controlled release systems are discussed in the review by Langer (*Science*, 249: 1527-1533 (1990)).

5. Forms and Dosages of IL-12

Suitable dosage forms of IL-12 for use in embodiments of the present invention encompass physiologically acceptable carriers that are inherently non-toxic and non-therapeutic. Examples of such carriers include ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts, or electrolytes such as protamine sulfate, disodium hydrogen phosphate, potassium hydrogen phosphate, sodium chloride, zinc salts, colloidal silica, magnesium trisilicate, polyvinyl pyrrolidone, cellulose-based substances, and PEG. Carriers for topical or gel-based forms of IL-12 polypeptides include polysaccharides such as sodium carboxymethylcellulose or methylcellulose, polyvinylpyrrolidone, polyacrylates, polyoxyethylene-polyoxypropylene-block polymers, PEG, and wood wax alcohols. For all administrations, conventional depot forms are suitably used. Such forms include, for example, microcapsules, nano-capsules, liposomes, plasters, inhalation forms, nose sprays, sublingual tablets, and sustained-release preparations.

Suitable examples of sustained-release preparations include semipermeable matrices of solid hydrophobic polymers containing the polypeptide, which matrices are in the form of shaped articles, e.g. films, or microcapsules. Examples of sustained-release matrices include polyesters, hydrogels (for example, poly(2-hydroxyethyl-methacrylate) as described by Langer et al., supra and Langer, supra, or poly(vinylalcohol), polylactides (U.S. Pat. No. 3,773,919), copolymers of L-glutamic acid and .gamma. ethyl-L-glutamate (Sidman et al, supra), non-degradable ethylene-vinyl acetate (Langer et al., supra), degradable lactic acidglycolic acid copolymers such as the LUPRON DEPOT (injectable microspheres composed of lactic acid-glycolicacid copolymer and leuprolide acetate), and poly-D-(−)-3-hydroxybutyric acid. While polymers such as ethylene-vinyl acetate and lactic acid-glycolic acid enable release of molecules for over 100 days, certain hydrogels release proteins for shorter time periods. When encapsulated IL-12 polypeptides remain in the body for a long time, they may denature or aggregate as a result of exposure to moisture at 37° C., resulting in a loss of biological activity and possible changes in immunogenicity. Rational strategies can be devised for stabilization depending on the mechanism involved. For example, if the aggregation mechanism is discovered to be intermolecular S—S bond formation through thiodisulfide interchange, stabilization may be achieved by modifying sulfhydryl residues, lyophilizing from acidic solutions, controlling moisture content, using appropriate additives, and developing specific polymer matrix compositions.

Sustained-release IL-12 containing compositions also include liposomally entrapped polypeptides. Liposomes containing a IL-12 polypeptide are prepared by methods known in the art, such as described in Eppstein et al., *Proc. Natl. Acad. Sci. USA*, 82: 3688-3692 (1985); Hwang et al., *Proc. Natl. Acad. Sci. USA*, 77: 4030 (1980); and U.S. Pat. Nos. 4,485,045 and 4,544,545. Ordinarily, the liposomes are the small (about 200-800 Angstroms) unilamelar type in which the lipid content is greater than about 30 mol. % cholesterol, the selected proportion being adjusted for the optimal Wnt polypeptide therapy. Liposomes with enhanced circulation time are disclosed in U.S. Pat. No. 5,013,556.

For the treatment of disease, the appropriate dosage of a IL-12 polypeptide will depend on the type of disease to be treated, as defined above, the severity and course of the disease, previous therapy, the patient's clinical history and response to the IL-12 therapeutic methods disclosed herein, and the discretion of the attending physician. In accordance with the invention, IL-12 is suitably administered to the patient at one time or over a series of treatments.

Depending on the type and severity of the disease, about 10 ng/kg to 2000 ng/kg of IL-12 is an initial candidate dosage for administration to the patient, whether, for example, by one or more separate administrations, or by continuous infusion. Humans can safely tolerate a repeated dosages of about 500 ng/kg, but single dosages of up to about 200 ng/kg should not produce toxic side effects. For example, the dose may be the same as that for other cytokines such as G-CSF, GM-CSF and EPO. For repeated administrations over several days or longer, depending on the condition, the treatment is sustained until a desired suppression of disease symptoms occurs. However, other dosage regimens may be useful. The progress of this therapy is easily monitored by conventional techniques and assays.

Il-12 may be administered along with other cytokines, either by direct co-administration or sequential administration. When one or more cytokines are co-administered with IL-12, lesser doses of IL-12 may be employed. Suitable doses of other cytokines, i.e. other than IL-12, are from about 1 µg/kg to about 15 mg/kg of cytokine. For example, the dose may be the same as that for other cytokines such as G-CSF, GM-CSF and EPO. The other cytokine(s) may be administered prior to, simultaneously with, or following administration of IL-12. The cytokine(s) and IL-12 may be combined to form a pharmaceutically composition for simultaneous administration to the mammal. In certain embodiments, the amounts of IL-12 and cytokine are such that a synergistic repopulation of blood cells (or synergistic increase in proliferation and/or differentiation of hematopoietic cells) occurs in the mammal upon administration of IL-12 and other cytokine thereto. In other words, the coordinated action of the two or more agents (i.e. the Il-12 and one or more cytokine(s)) with respect to repopulation of blood cells (or proliferation/differentiation of hematopoietic cells) is greater than the sum of the individual effects of these molecules.

Therapeutic formulations of IL-12 are prepared for storage by mixing IL-12 having the desired degree of purity with optional physiologically acceptable carriers, excipients, or stabilizers (Remington's Pharmaceutical Sciences, 16th edition, Osol, A., Ed., (1980)), in the form of lyophilized cake or aqueous solutions. Acceptable carriers, excipients, or stabilizers are nontoxic to recipients at the dosages and concentrations employed, and include buffers such as phosphate, citrate, and other organic acids; antioxidants including ascorbic acid; low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, arginine, or lysine; monosaccharides. disaccharides, and other carbohydrates including glucose, mannose, or dextrins; chelating agents such as EDTA; sugar alcohols such as mannitol or sorbitol; salt-forming counterions such as sodium; and/or non-ionic surfactants such as TWEEN, PLURONICS or polyethylene glycol (PEG).

IL-12 also may be entrapped in microcapsules prepared, for example, by coacervation techniques or by interfacial polymerization (for example, hydroxymethylcellulose or gelatin-microcapsules and poly-(methylmethacylate) microcapsules, respectively), in colloidal drug delivery systems (for example, liposomes, albumin microspheres, microemulsions, nano-particles, and nanocapsules), or in macroemulsions. Such techniques are disclosed in Remington's Pharmaceutical Sciences, supra.

IL-12 to be used for in vivo administration must be sterile. This is readily accomplished by filtration through sterile filtration membranes, prior to or following lyophilization and reconstitution. IL-12 ordinarily will be stored in lyophilized form or in solution. Therapeutic IL-12 compositions generally are placed into a container having a sterile access port, for example, an intravenous solution bag or vial having a stopper pierceable by a hypodermic injection needle.

When applied topically, IL-12 is suitably combined with other ingredients, such as carriers and/or adjuvants. There are no limitations on the nature of such other ingredients, except that they must be physiologically acceptable and efficacious for their intended administration, and cannot degrade the activity of the active ingredients of the composition. Examples of suitable vehicles include ointments, creams, gels, or suspensions, with or without purified collagen. The compositions also may be impregnated into transdermal patches, plasters, and bandages, preferably in liquid or semi-liquid form.

For obtaining a gel formulation, IL-12 formulated in a liquid composition may be mixed with an effective amount of a water-soluble polysaccharide or synthetic polymer such as PEG to form a gel of the proper viscosity to be applied topically. The polysaccharide that may be used includes, for example, cellulose derivatives such as etherified cellulose derivatives, including alkyl celluloses, hydroxyalkyl celluloses, and alkylhydroxyalkyl celluloses, for example, methylcellulose, hydroxyethyl cellulose, carboxymethyl cellulose, hydroxypropyl methylcellulose, and hydroxypropyl cellulose; starch and fractionated starch; agar; alginic acid and alginates; gum arabic; pullullan; agarose; carrageenan; dextrans; dextrins; fructans; inulin; mannans; xylans; arabinans; chitosans; glycogens; glucans; and synthetic biopolymers; as well as gums such as xanthan gum; guar gum; locust bean gum; gum arabic; tragacanth gum; and karaya gum; and derivatives and mixtures thereof. The preferred gelling agent herein is one that is inert to biological systems, nontoxic, simple to prepare, and not too runny or viscous, and will not destabilize the IL-12 molecule held within it.

Preferably the polysaccharide is an etherified cellulose derivative, more preferably one that is well defined, purified, and listed in USP, e.g., methylcellulose and the hydroxyalkyl cellulose derivatives, such as hydroxypropyl cellulose, hydroxyethyl cellulose, and hydroxypropyl methylcellulose. Most preferred herein is methylcellulose.

The polyethylene glycol useful for gelling is typically a mixture of low and high molecular weight PEGs to obtain the proper viscosity. For example, a mixture of a PEG of molecular weight 400-600 with one of molecular weight 1500 would be effective for this purpose when mixed in the proper ratio to obtain a paste.

The term "water soluble" as applied to the polysaccharides and PEGs is meant to include colloidal solutions and dispersions. In general, the solubility of the cellulose derivatives is determined by the degree of substitution of ether groups, and the stabilizing derivatives useful herein should have a sufficient quantity of such ether groups per anhydroglucose unit in the cellulose chain to render the derivatives water soluble. A degree of ether substitution of at least 0.35 ether groups per anhydroglucose unit is generally sufficient. Additionally, the cellulose derivatives may be in the form of alkali metal salts, for example, the Li, Na, K, or Cs salts.

If methylcellulose is employed in the gel, preferably it comprises about 2-5%, more preferably about 3%, of the gel and IL-12 is present in an amount of about 300-1000 mg per ml of gel.

An effective amount of IL-12 to be employed therapeutically will depend, for example, upon the therapeutic objectives, the route of administration, and the condition of the patient. Accordingly, it will be necessary for the therapist to titer the dosage and modify the route of administration as required to obtain the optimal therapeutic effect. Typically, the clinician will administer IL-12 until a dosage is reached that achieves the desired effect. A typical daily dosage for systemic treatment might range from about 10 ng/kg to up to 2000 ng/kg or more, depending on the factors mentioned above. As an alternative general proposition, the IL-12 receptor is formulated and delivered to the target site or tissue at a dosage capable of establishing in the tissue an IL-12 level greater than about 0.1 ng/cc up to a maximum dose that is efficacious but not unduly toxic. This intra-tissue concentration should be maintained if possible by the administration regime, including by continuous infusion, sustained release, topical application, or injection at empirically determined frequencies. The progress of this therapy is easily monitored by conventional assays.

The following examples are given to illustrate the present invention. It should be understood, however, that the invention is not to be limited to the specific conditions or details described in these examples. All printed publications referenced herein are specifically incorporated by reference.

EXAMPLES

Example 1—Materials and Methods for Formulation Test Using Irradiated Mice

Mice:

Female mice approximately 9-10 weeks old were purchased from Harlan Laboratories (Indianapolis, Ind.) and were each at least 20 grams upon receipt. Mice were housed in autoclaved cages, and were maintained in an air-conditioned, specific pathogen-free animal room regulated at a temperature of 21° to 23° C. and a relative humidity of 50% to 60%. Mice were given commercial rodent chow and water ad libitum. Mice were quarantined for one week prior to the start of the study. All experiments in this study were approved by the Institutional Animal Care and Use Committee at BATTS Laboratories (Northridge, Calif.).

Radiation:

Irradiation of the mice was carried out using a Gammacell 40. Treated and untreated mice received 7.9 Gy (790 rads) (n=10 for treated mice). The control group is a combination of mice injected with sucrose or trehalose (n=10 for each; n=20 total). Mice were irradiated in a specially constructed "pie-box" designed to maintain mice placement in the center of the irradiator, so to provide an evenly distributed dose of radiation.

Drug: Recombinant mouse IL-12 (rmIL-12) was manufactured by SBH Sciences (Natick, Mass.) and supplied as a liquid formulated in phosphate-buffered saline (PBS). Prior to use in the study, liquid rmIL-12 was diluted into one of two formulations, namely (1) a sucrose/mannitol or (2) a trehalose-based formulation. The specific composition of each formulation is as follow: (1) 2% Sucrose, 4% Mannitol, 0.02% TWEEN 20, 10 mM Sodium Acetate, pH 5.6, and (2) 6% Trehalose, 0.04% TWEEN 20, 5 mg/ml Sodium phosphate Monobasic anhydrous, 1.2 mg/ml Sodium phosphate Dibasic anhydrous. The doses injected were verified by murine IL-12 ELISA (Biolegend San Diego, Calif.).

Radiomitigation:

Irradiated mice received subcutaneous (SC) injections of murine rmIL-12 24 hours after the irradiation. Mice were observed over the subsequent 30 days for survival and the weight of each mouse was determined twice weekly. All supportive care, including antibiotics, was excluded to increase the stringency of the survival studies.

Statistical Methods:

Power-On the basis of generic power analysis we determined that for alpha=0.05 and power=0.8 with historical estimates of group variance and an effect size of a 3-4 day elevation in survival time of rmIL-12-treated mice vs. control mice, a group size of n=10 sufficed. Later it was found that this same n was adequate for the detection of 40% or greater group increments in survival by chi square analysis and the Fisher exact probability test where appropriate.

Kaplan-Meier Analysis:

The traditional measure of survival time is the Kaplan-Meier survival function. Stratified Kaplan-Meier was employed to examine overall differences in survival time across rmIL-12 and vehicle control groups. Weight loss following radiation treatment was analyzed as a covariate. Subsequent comparisons of individual experimental group vs. control survival times were performed. The analyses under these conditions were sufficiently sensitive to detect as little as a 3-4 day difference in survival time. Subsequent analyses of variance (ANOVAs) with post hoc Tukey tests were performed on the survival time measure to validate the dose response function and to determine which formulation gave the best survival times for a given dose of rmIL-12.

Results:

% group survival analysis-% group survival in the various treatment groups was compared to control % survival by the k means chi square test and the Fisher exact probability test where appropriate Independent Variables:

The variables examined in these studies included dose of rmIL-12 and formulation (sucrose or trehalose).

Example 2

An experiment to further investigate the radiomitigation properties of murine rmIL-12 was conducted using two formulations, a sucrose and trehalose-based formulation. Three doses of murine rmIL-12 were tested using either formulation, along with the respective vehicle control group. The doses investigated were 2, 18 and 162 ng and compared to vehicle alone.

Mice were injected SC with rmIL-12 at 24 hours after exposure to 7.9 Gy. Kaplan-Meier (K-M) plots are shown in FIG. 1 for rmIL-12 in the sucrose-based formulation and in FIG. 2 for RmIL-12 in the trehalose-based formulation.

Figure 2:
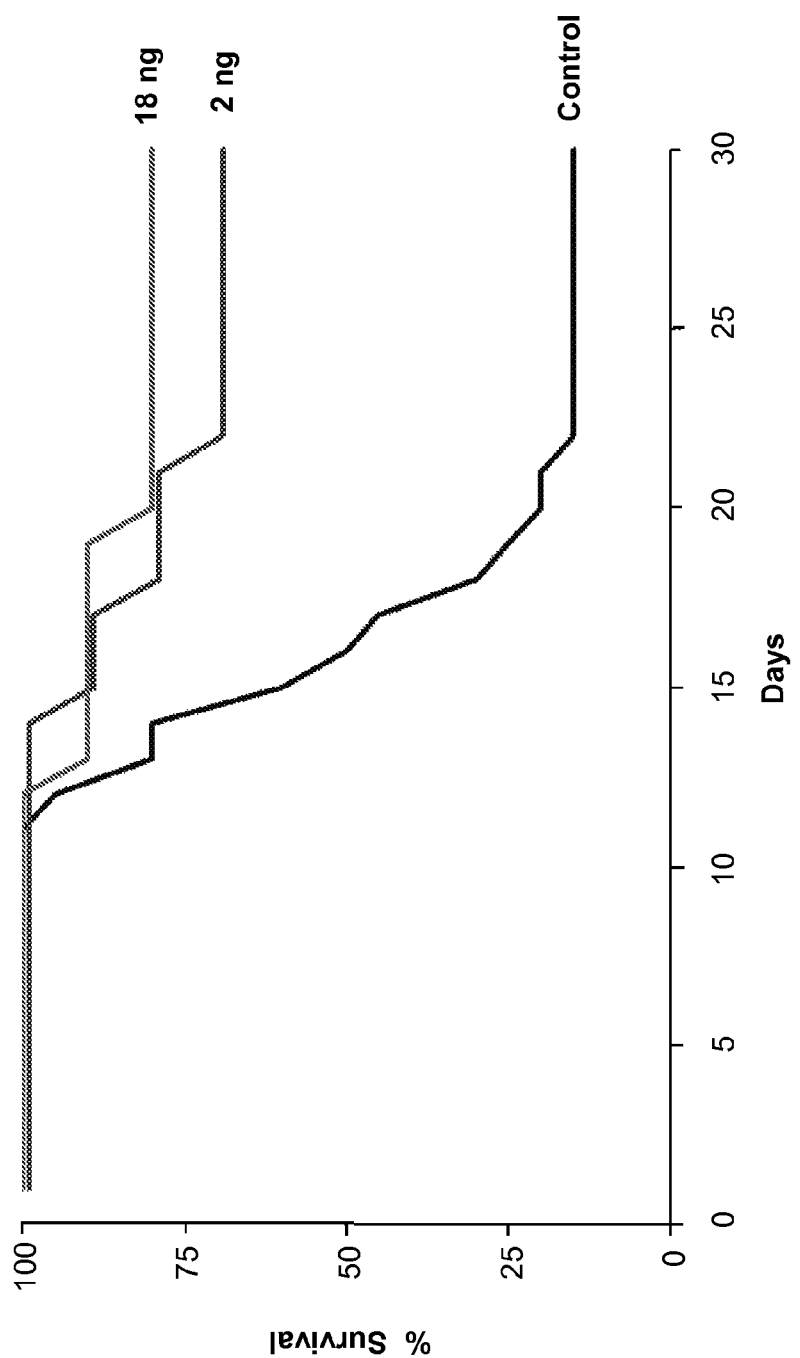
FIG. 2: Shows Kaplan-Meier (K-M) plots for murine RmIL-12 for a trehalose-based formulation following subcutaneous (SC) injection with RmIL-12 at 24 hours after exposure to 7.9 Gy. The results show that IL-12 in a trehalose formulation mitigates the effects of lethal irradiation of mice. Control mice received no IL-12 (line labeled "Control"); Treated mice received 2 ng (line labeled "2 ng") or 18 ng (line labeled "18 ng") IL-12 in a trehalose-based formulation.

As depicted in FIGS. 1 and 2, rmIL-12 in either formulation produced potent radiomitigation effects. The overall survival (defined as % group survival) for rmIL-12 in the sucrose formulation (FIG. 1) was 50% at 18 ng and 60% at 162 ng (p<0.05, Fisher exact probability test) (LD85$_{30}$). For trehalose-formulated rmIL-12 (FIG. 2), the overall survival was 70% at 2 ng (p<0.02, Fisher test) and 80% at 18 ng (p<0.005, Fisher test) (LD85$_{30}$).

Although the 2 ng dose of rmIL-12 in the sucrose-based formulation produced a modest increase in percent group survival, this dose was not significantly different from control survival either by Kaplan-Meier analysis of survival time or chi square analysis of % group survival. Similarly, although a modest increase in group survival was observed for the 162 ng dose in the trehalose-based formulation, survival was not significantly different from control survival percentage or survival time.

In contrast, the 162 ng dose of rmIL-12 in the sucrose formulation significantly elevated both % group survival (Fisher test, $p<0.05$) and survival time (K-M analysis, $p<0.001$) over the control. The 18 ng rmIL-12 formulation in sucrose elevated survival time over controls (K-M, $p<0.04$), but barely missed elevating % group survival (Fisher test, n.s). RmIL-12 at 2 ng in the trehalose formulation elevated both % survival (Fisher test, $p<0.02$) and marginally elevated survival time (K-M analysis, $p<0.07$). The 18 ng dose of IL-12 elevated both % group survival (Fisher test, $p<0.005$) and survival time (K-M analysis, $p<0.03$).

Figure 3:
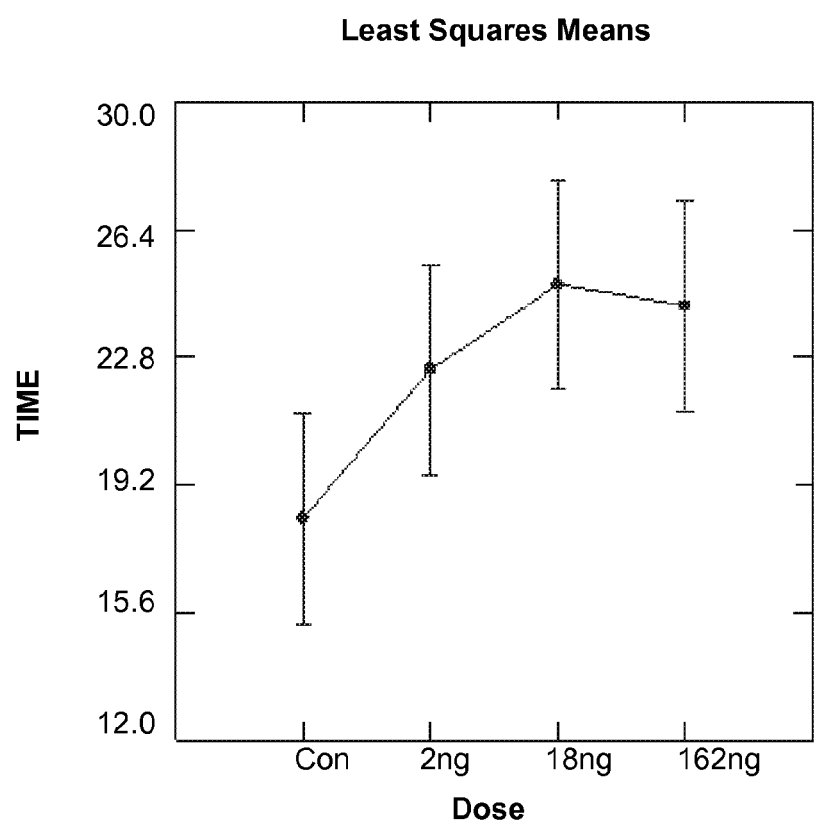
FIG. 3: Shows a graph of survival time vs dose for the experiments shown in FIGS. 1 and 2.
Figure 4:
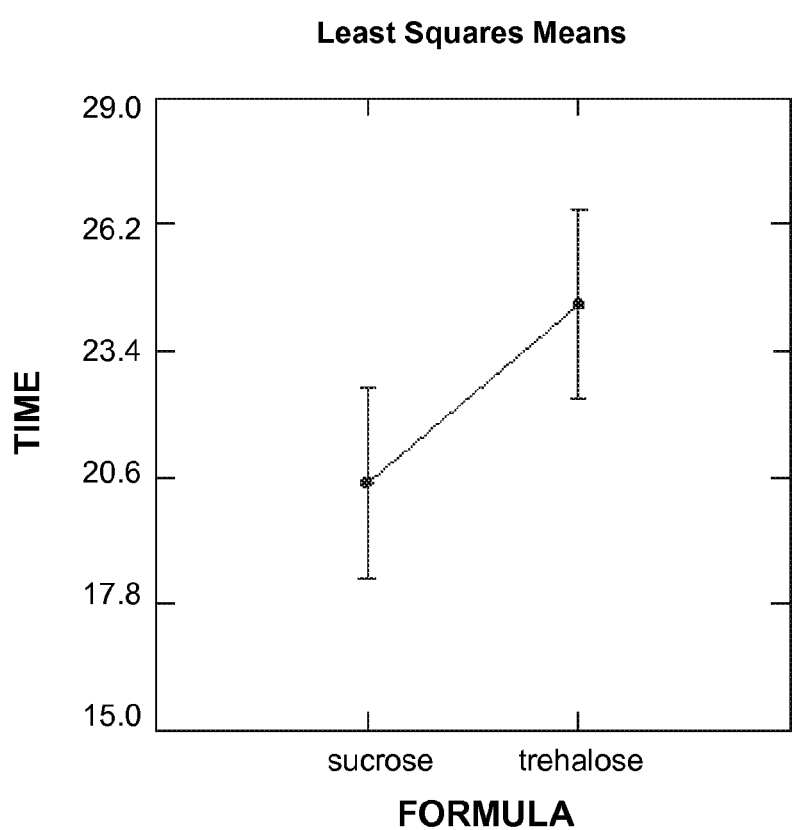
FIG. 4: Shows a graph of survival time vs formulation (sucrose and trehalose) for the experiments shown in FIGS. 1 and 2.

A two factor analysis of variance (ANOVA) was performed on the survival times from the K-M analyses. The factors were dose and formulation type. Both factors were highly significant ($p<0.01$), but the Dose X Formulation interaction was not. The significant formulation factor indicated the surprising and unexpected result that survival time was longer in the trehalose formulation as compared to the sucrose formulation when administered at the same doses. These results suggest greater potency for the trehalose formulation, which is in agreement with the K-M and chi square analyses. The significant dose factor suggests that survival time is dose-related, although maximal survival time is higher with the trehalose formulation (FIG. 3 (survival time vs dose) and FIG. 4 (survival time vs formulation)).

Although rmIL-12 provided statistically significant radiomitigation effects using either the sucrose or the trehalose formulation, rmIL-12 formulation in trehalose added an additional benefit in that this formulation lowers the effective dose required for radiomitigation effects of rmIL-12 about 9-10-fold, i.e., rmIL-12 stabilized by trehalose increases its potency.

rmIL-12 formulated in trehalose allows a targeted, low human dose, which is 100 ng/kg (the 2 ng murine dose can be converted to approximately an 8 ng/kg human dose and the 18 ng murine dose converts to about 72 ng/kg human dose). Further, the data support the notion that the use of trehalose as the formulation for human IL-12 will likely increase the safety profile of the drug during clinical trials.

In conclusion, rmIL-12 possesses potent radiomitigation effects when administered 24 hours after lethal irradiation using two different formulations, namely a sucrose/mannitol formulation (pH 5.6) and trehalose-based formulation (pH 5.6). Unexpectedly and surprisingly, the trehalose formulation significantly increases potency of rmIL-12 relative to the sucrose/mannitol formulation.

Example 3—Materials and Methods for Stability Studies of rHu-IL-12

Formulation Parameters:

Formulation pH, buffers, and tonicity modifiers were tested in formulation studies of recombinant human IL-12 (rHu-IL-12). Various combinations of formulations were created, stored at 25° C. and 40° C. for 24 weeks, and then tested for the level of degradation of rHu-IL-12 using either SE-HPLC, RP-HPLC, or SDS PAGE. Based on the agitation stress study with various surfactants, poloxamer 188 was selected as a surfactant for these studies. Table 4 below lists the formulations used in the study.

TABLE 4

Formulations Tested for Stability after Storage for 24 weeks

| Name | Buffer | pH | Tonicity modifier | Surfactant (0.1%) | IL-12 Conc. (µg/ml) |
|---|---|---|---|---|---|
| DPBS | n/a* | n/a* | n/a* | n/a* | 500 |
| DPBSF | n/a* | n/a* | n/a* | poloxamer 188 | 500 |
| A45N | sodium acetate | 4.5 | 150 mM NaCl | poloxamer 188 | 20 |
| A45T | sodium acetate | 4.5 | 6% Trehalose | poloxamer 188 | 20 |
| A5N | sodium acetate | 5.0 | 150 mM NaCl | poloxamer 188 | 500 |
| A5T | sodium acetate | 5.0 | 6% Trehalose | poloxamer 188 | 500 |
| A55N | sodium acetate | 5.5 | 150 mM NaCl | poloxamer 188 | 20 |
| A55T | sodium acetate | 5.5 | 6% Trehalose | poloxamer 188 | 20 |
| H6N | histidine | 6.0 | 150 mM NaCl | poloxamer 188 | 20 |
| H6T | histidine | 6.0 | 6% Trehalose | poloxamer 188 | 20 |
| P6T | sodium phosphate | 6.0 | 6% Trehalose | poloxamer 188 | 20 |

*Formulation buffer is Dulbecco's phosphate buffered saline

Stress Conditions:

The formulations were tested under the conditions listed in Table 5 below.

TABLE 5

Stress Conditions tested for Formulations

| Stress | Condition | Time Points |
|---|---|---|
| Temperature | −20° C. | 2, 4, 6, 24 weeks |
|  | 5° C. | 0, 2, 4, 6, 24 weeks |
|  | 25° C. | 2, 4, 6, 24 weeks |
|  | 40° C. | 2, 4, 6, 24 weeks |
| Agitation | Vortex | 4 hours |
| Freeze/Thaw | −70° C. to room temp. | 5 cycles |
| UV Exposure | Broadband UV | 24 hours |

Freezing and thawing and UV exposure had no observed effect on degradation of rHU-IL-12 in the formulations (data not shown).

Analysis of Degradation Products:

The amount of degradation in a formulation was analyzed using size exclusion high pressure liquid chromatography (SE-HPLC), reverse-phase high pressure liquid chromatography, and sodium dodecyl sulfate polyacrylamide gel electrophoresis (SDS-PAGE).

SE-HPLC used a mobile phase 100 mM sodium phosphate and 400 mM NaCl at pH 7.0. The column was a TSKGel Super SW3000, 4.6×300 mm. Loads of 2 µg were run at a flow rate of 0.35 mL/min for 20 minutes.

RP-HPLC used a mobile phase A of 0.1% TFA in water, mobile phase B of 0.1% TFA in acetonitrile, a Vydac C18 column. The column temperature was 30° C., the flow rate was 0.5 mL/min, the detector was 214 nm. The gradient is shown below in table 6.

TABLE 6

| Time (min) | RP-HPLC gradient % B |
|---|---|
| 0 | 25 |
| 10 | 25 |
| 67 | 65 |
| 69 | 90 |
| 71 | 25 |
| 90 | 10 |

SDS-PAGE used a variable percentage gel (NuPAGE Novex 4-12% Bis Tris) and was silver stained. Sample load was 1.5 μg.

Example 4—Effect of pH on Stability of IL-12 Formulation

Figure 5:
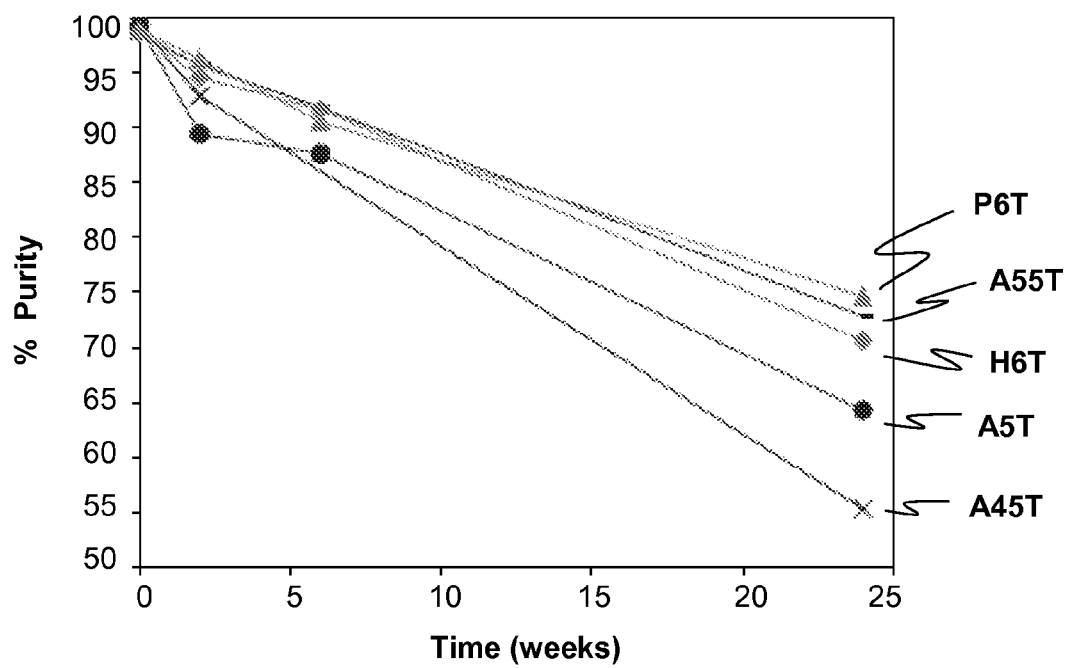
FIG. 5: Shows a graph of the effect of pH on degradation over time of rHu-IL-12 during storage.

Formulations of rHu-IL-12 having a pH range between 4.5 and 6.0 were stored for 24 weeks at 40° C. and then tested using SE-HPLC to determine the effect of pH on degradation of rHu-IL-12 during storage. The formulations contained either sodium acetate, histidine, or sodium phosphate as a buffer, a tonicity modifier of 6% trehalose, the surfactant poloxamer 188, and rHu-IL-12 concentrations of either 20 or 500 μg/ml. FIG. 5 shows the SE-HPLC purity profiles of a select group of the trehalose-containing formulations following storage for 24 weeks at 40° C. Details of the formulations shown in FIG. 5 are listed in table 7 below.

TABLE 7 rHu-IL-12 Formulations Tested

| Name | Buffer | pH | Tonicity modifier | Surfactant | rHu-IL-12 Conc. (μg/ml) |
|---|---|---|---|---|---|
| A45T | sodium acetate | 4.5 | 6% Trehalose | poloxamer 188 | 20 |
| A5T | sodium acetate | 5.0 | 6% Trehalose | poloxamer 188 | 500 |
| A55T | sodium acetate | 5.5 | 6% Trehalose | poloxamer 188 | 20 |
| H6T | histidine | 6.0 | 6% Trehalose | poloxamer 188 | 20 |
| P6T | sodium phosphate | 6.0 | 6% Trehalose | poloxamer 188 | 20 |

Aggregation became more severe at lower pH's, indicating that lower pH leads to lower stability of rHu-IL-12 over a 24 week period. No significant pH effect was observed in formulations at 500 μg/mL of rHu-IL-12. The effects of pH during storage were not as apparent when analyzed by RP-HPLC and SDS-PAGE (data not shown).

Example 4—Effect of Trehalose on rHu-IL-12 Storage Stability

Trehalose and sodium chloride at 6.0% and 150 mM, representing a non-ionic tonicity modifier and an ionic tonicity modifier respectively, were tested as tonicity modifiers in this study.

Figure 6A:
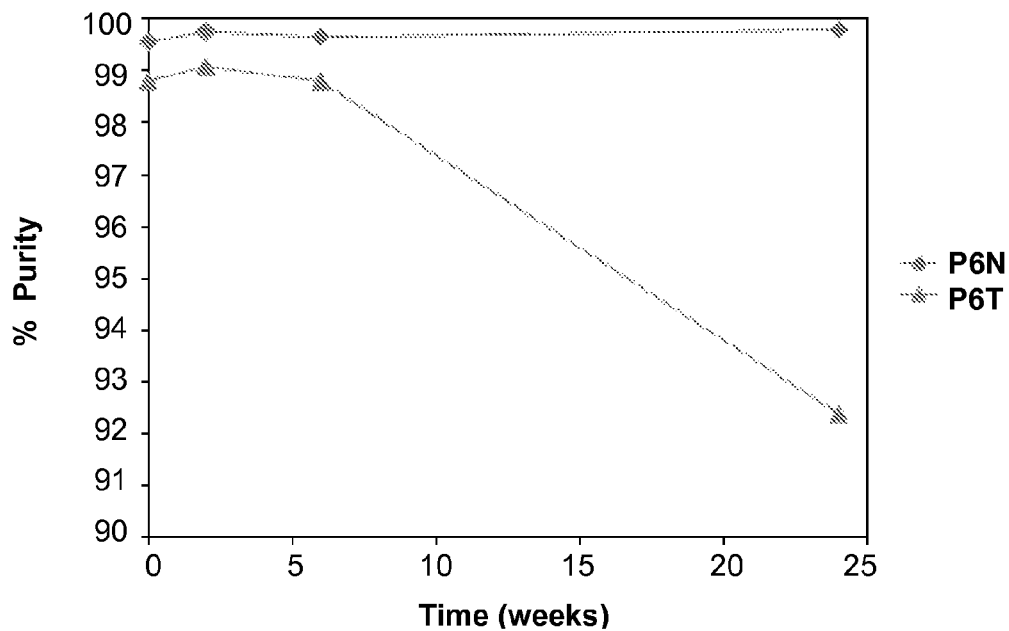
FIG. 6A shows a graph of percent purity of 20 µg/mL rHu-IL-12 (measured by SE-HPLC) stored over 24 weeks at 25° C. using trehalose or NaCl as tonicity modifiers.
Figure 6B:
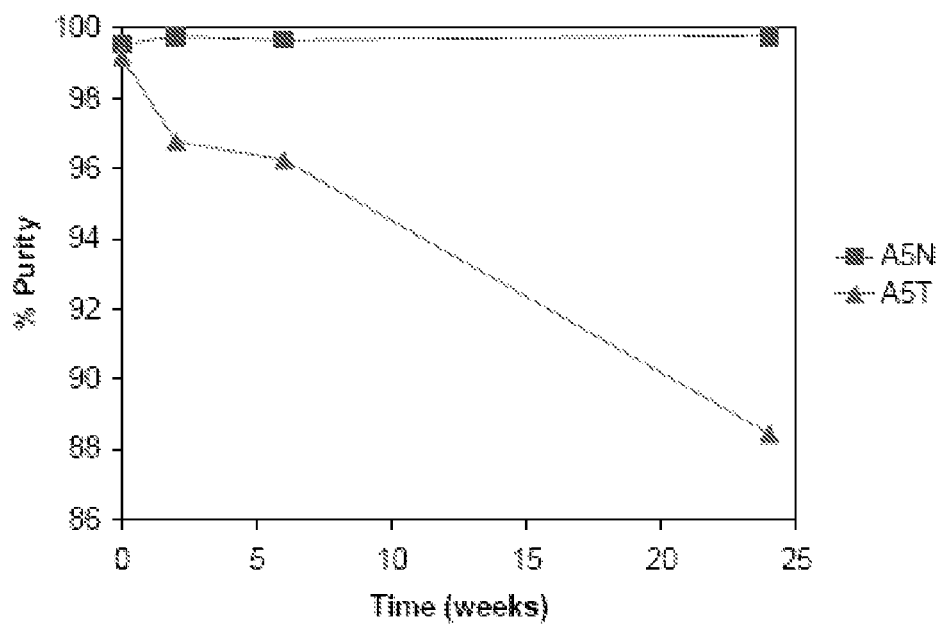
FIG. 6B shows a graph of percent purity of 500 µg/mL rHu-IL-12 (measured by SE-HPLC) stored over 24 weeks at 25° C. using trehalose or NaCl as tonicity modifiers.

Results:

For formulations with 20 μg/mL rHu-IL-12 at all pH's except for pH 4.5, trehalose showed greater aggregation than NaCl when analyzed by SE-HPLC as described in Example 3. FIG. 6A shows SE-HPLC purity data for P6N (150 mM NaCl) and P6T (trehalose) between 0 and 24 weeks at 25° C. The NaCl sample showed virtually no decrease from 100% purity at 24 weeks, while the trehalose sample showed only a 92% purity at 24 weeks. Similarly, 500 μg/mL rHu-IL-12 formulations at 25° C. using 150 mM NaCl (A5N) showed 100% purity at 24 weeks while a comparable trehalose sample (A5T) was only about 88% pure at 24 weeks. (FIG. 6B).

Trehalose also negatively affected the recovery of the product at elevated temperature. 20 μg/mL rHu-IL-12 at 40° C. for 24 weeks in 150 mM NaCl resulted in a concentration of 15 μg/ml (from 20 μg/ml at the start of the study), while the same concentration of rHu-IL-12 in trehalose resulted in a final concentration of 10 μg/ml at 24 weeks. 150 mM NaCl as a tonicity modifier results in greater stability of rHu-IL-12 over time than 6% trehalose.

Example 5—Effect of Buffer on Stability

Histidine and sodium phosphate were compared as buffering agents at pH 6.0 for 24 weeks of storage using 150 mM NaCl for tonicity. After 24 weeks of storage at 25° C., sodium phosphate formulations showed greater purity than histidine when analyzed by SE-HPLC. P6N showed near 100% purity, while H6N had a purity of 96%. When analyzed by RP-HPLC, noticeable loss of recovery and resolution is observed in the histidine formulation.

Example 6—Summary of Formulation Comparisons

Results from the preformulation comparisons of Examples 3-5 showed that the product loses recovery and produces non-covalent aggregates during agitation stress, which can be prevented by adding 0.1% of poloxamer 188 as a surfactant. The product forms soluble aggregates at low pH 4.5-5.5, especially in the presence of trehalose. The product also showed decreased stability when histidine was used as a buffering agent.

Two formulations showed best stability among tested.
(1) Dulbecco's phosphate buffered saline,
(2) Sodium Phosphate (10 mM), NaCl (150 mM), 0.1% (w/v) poloxamer 188, and 20 μg/mL rHu-IL-12, at pH 6.0.

These formulations are stable for at least 6 month when stored at 5° C. Considering that the product rapidly degrades at low pH, it is not recommended that the formulations be stored long-term at frozen temperatures. It is known that the pH of sodium phosphate can decrease upon freezing due to selective crystallization of disodium phosphate component.

Example 7—Potency Assay for IL-12 Formulations

Materials and Methods—

IL-12 in vitro potency assay determines the potency of rHuIL-12 for inducing IFN-γ expression in a purified population of human peripheral blood mononuclear cells (PBMC). Human peripheral blood cells are treated with a single step gradient with Ficoll-Hypaque (LSM-lymphocyte separation medium) to separate white blood cells from red blood cells, and the red blood cells are discarded. The remaining leukocytes are then incubated with anti-CD14 antibody to remove the monocyte and dendritic cell populations, which can produce endogenous IL-12 and confound the results. The cell population remaining following anti-CD14 antibody treatment is highly enriched for lymphocytes Purified human PBMC (obtained using leukophoresis) are aliquoted in RPMI 1640/10% fetal bovine serum into 96 well tissue culture plates at a density of 2.5×10⁵ cells per well then challenging the cells with 27 fM to 27 pM IL-12 at 37° C., 5% $CO_2$ for 16 to 18 hours. IFN-γ expression by the challenged PBMC is then measured using a human IFN-γ specific ELISA kit from BioLegend. An EC50 value for IL-12-induced INF-γ expression is then determined from a four parameter fit of the ELISA response data. The EC50 is the effective concentration at which 50% of the cells respond by producing IFN-γ.

Various formulations of IL-12 as described in Example 3 and listed in Table 4 were assayed for IFN-γ expression after 4 weeks of storage and after 24 weeks of storage, both time points at various temperatures.

Results:

After 4 weeks of storage, the P6N formulation showed one of the lowest EC50 amounts following storage at −20° C. at 0.484 pg. Results for 4 weeks of storage are summarized in Table 8 below.

TABLE 8

EC50 for IL-12 Formulations after 4 weeks storage

| Name | Temp. (° C.) | EC50 at 4 weeks (pg) |
| --- | --- | --- |
| DPBS | +40 | 2.42 |
| DPBSF | +40 | 3.84 |
| A45N | +40 | NA |
| A45T | +40 | 2.41 |
| A5N | +40 | 1.07 |
| A5T | +40 | 0.718 |
| A55N | −20 | 0.767 |
| A55N | +5 | 0.719 |
| A55N | +40 | 1.48 |
| A55N | +40 | 0.759 |
| P6N | −20 | 0.481 |
| P6N | +5 | 1.79 |
| P6N | +40 | 1.05 |
| P6N | +40 | 0.949 |
| P6T | +40 | 2.25 |

After 24 weeks of storage, the P6N formulation showed consistently low EC50 between −20° C. and +25° C. (0.289 pg to 0.379 pg). The EC50 only increased when the storage temperature was at +40° C. (to 0.989 pg). The results are summarized in Table 9 below.

TABLE 9

EC50 of IL-12 Formulations after 24 Weeks Storage

| Name | Temp. (° C.) | EC50 at 24 weeks (pg) |
| --- | --- | --- |
| P6N | Control (unstored) | 0.289 |
| DPBS | Control (unstored) | 0.242 |
| DPBS | +5 | 0.232 |
| DPBSF | +5 | 0.334 |
| DPBSF | +40 | 1.34 |
| P6N | −20 | 0.306 |
| P6N | +5 | 0.372 |
| P6N | +25 | 0.289 |
| P6N | +40 | 0.941 |
| P6T | +5 | 0.469 |
| P6T | +40 | 6.95 |
| A45T | +40 | 5.1 |

Example 8—Materials and Methods for PK/PD Study of Formulation in Primates

A single dose study was performed to determine the pharmacokinetics (PK) and pharmacodynamics (PD) of rHu-IL-12 following subcutaneous (SC) administration at a dose of 1 µg/kg in three different formulations to non-irradiated rhesus monkeys. The biomarkers studied were IL-12, EPO, IFN-γ, IL-15, IL-18 and Neopterin.

Vehicles:

Vehicle 1 (P56TT) was at pH 5.6 and contained 6% trehalose. Vehicle 2 (P6NF) had a pH of 6.0 and contained 10 mM sodium phosphate, 150 mM NaCl, and 0.1% poloxamer 188. Vehicle 3 (p6TF) was at pH 6.0 and contained 10 mM sodium phosphate, 6% trehalose and 0.1% poloxamer 188.

Administration and Sample Collection:

Vehicles containing 1 µg/kg of rHu-IL-12 were administered subcutaneously once per test subject. Following administration of the rHu-IL-12 in three different vehicles (Groups 1-3) blood was collected at selected time points from each animal: 0, 2, 6, 12, 18, 24, 30, 36, 48, 72, 96, 120, 144, 168, and 192 hr. Each blood sample was collected by venipuncture into tubes containing K2-EDTA as anticoagulant and kept on wet ice pending centrifugation (maximum 30 minutes). Samples were centrifuged under refrigeration (approximately +4° C. at 1500 g (RCF)) for 10 minutes. Plasma was aliquoted as appropriate and frozen until analyzed.

ELISA Analysis:

ELISA analysis was performed on the samples using the following commercial kits: Quantikine Human IL-12 (p70) ELISA (R&D Systems—Kit #D1200); Monkey IFN-γ (Mabtech #3420M-1H-6); Quantikine Human EPO ELISA (R&D Systems—Kit #DEP00); Quantikine Human IL-15 ELISA (R&D Systems—Kit #D1500); Human IL-18 ELISA (MBL/R&D Systems—Kit #7620); Neopterin ELISA (GenWay—Kit #40-371-25012).

Pharmacokinetic Analysis:

The pharmacokinetic analysis consisted of assessment of standard parameters including: Tmax, Cmax, area under the curve (AUC), t1/2, elimination rate constant, initial volume of distribution (Vd), and clearance (CL) wherever possible. Plasma concentration versus time data was analyzed by noncompartmental analysis (NCA) with PK Functions for Excel. The nominal blood draw times were utilized, and rHu-IL-12 dose delivered was calculated based on the nominal dose and the mean predose body weight. IL-12, gamma-interferon (IFN-γ), erythropoietin (EPO), IL-15, IL-18 and Neopterin concentration versus time curves were all analyzed using NCA. The lower limits of quantitation for IL-12, IFN-γ, EPO, IL-15, IL-18 and Neopterin were 7.8 pg/mL, 7.8 pg/mL, 25 pg/mL, 3.9 pg/mL, 25.6 pg/mL, and 342 pg/mL, respectively. In many cases these curves involved significant extrapolation for $AUC_{0-\infty}$ calculation, and consequently, $AUC_{0-t}$ was used as a measure of exposure for consistency. No clearance parameters or volume of distribution parameters were calculated for IL-15, IL-18, Neopterin, IFN-γ and EPO.

Example 9—Pharmacokinetics of IL-12 Administered to Primates

Figure 7:
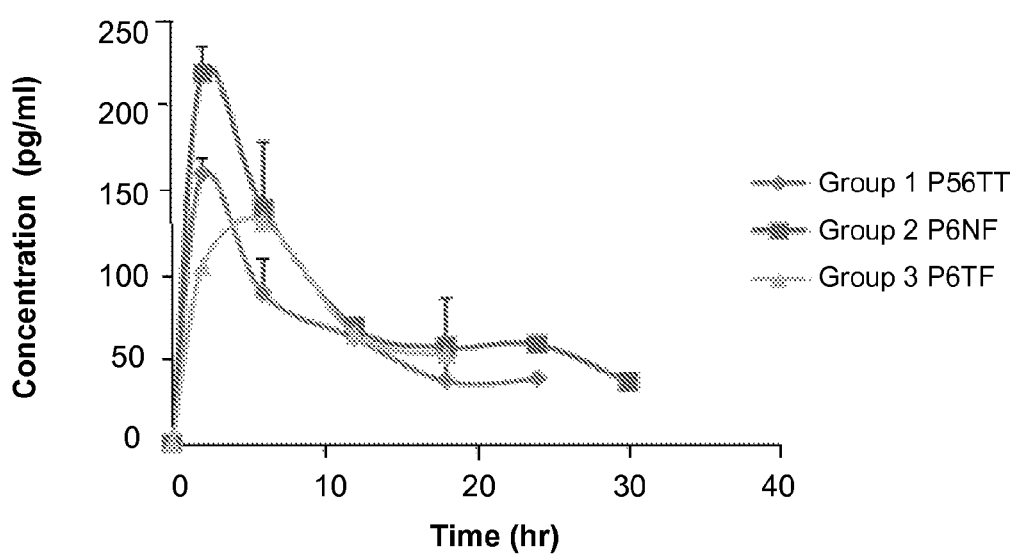
FIG. 7: Shows a graph of IL-12 concentration in blood over time following injection of three different formulations of rHu-IL-12 into primates.

Blood samples from primates treated with rHu-IL-12 in different vehicles were analyzed for IL-12 using ELISA, as described in Example 8. The final IL-12 PK parameters for doses of 1 µg/kg are summarized in Table 10 and FIG. 7 plots the concentration vs. time curve. It is important to indicate that group sizes were very small (n=1-2). Any statistical analysis must be purely descriptive and tentative. Furthermore, due to the sparseness of the data PK parameters could only be calculated for the group average concentrations at each timepoint. In a few cases it was necessary to interpolate a missing concentration based on the immediately preceding and following time point concentrations.

Cmax of IL-12 was highest for the Group 2 formulation P6NF. The confidence interval defined as mean±2 SE would extend from 187 to 250 pg/ml. The Cmax values for the other formulations are clearly lower than the lowest bound of the Group 2 P6NF confidence interval, suggesting this formulation produces a significantly higher Cmax. The best estimate (modal value) for Tmax from these data is 2 hr (actual range=2-6 hr). Half-lives for the three formulations are very similar, extending from approximately 11 to 13 hr. Likewise elimination rate constants are nearly identical for the three formulations. $AUC_{0-t}$ values differed from $AUC_{0-inf}$ values by as much as 40% indicating the sparseness of the data set and the consequent difficulty in extrapolating to the AUC at infinity. For these reasons the $AUC_{0-t}$ values are considered more reliable. With that caveat in mind, the $AUC_{0-t}$ for Group 2 (P6NF) was more than 50% higher than that for the other two formulations. Since the $AUC_{0-t}$ value is a single point estimate based on pooling the available data, no statistical analysis is possible, except to say that Cmax is generally correlated with the AUC. CL/F was numerically lowest in this group consistent with the highest $AUC_{0-t}$. The mean volume of distribution (Vz/F) ranged from about 24 to 33 L. The volume of distribution is suggestive of a low bioavailability (F) and/or a large distribution into extravascular spaces.

TABLE 10

Summary of PK Parameters for IL-12

| ID | $C_{max}$ (pg/ml) | $T_{max}$ (hr) | $T_{1/2}$ (hr) | $AUC_0$ (pg*hr/ml) | $K_{el}$ (1/hr) | $AUC_\infty$ (pg*hr/ml) | $V_d/F$ (ml) | CL/F (ml/hr) |
|---|---|---|---|---|---|---|---|---|
| Group 1 (P56TT) | 159.26 | 2.00 | 10.69 | 1640.48 | 0.06 | 2236.27 | 30354.66 | 1967.80 |
| Group 2 (P6NF) | 218.75 | 2.00 | 12.07 | 2574.92 | 0.06 | 3216.19 | 23828.20 | 1368.10 |
| Group 3 (P6TF) | 131.39 | 6.00 | 12.91 | 1517.86 | 0.05 | 2493.71 | 32869.30 | 1764.40 |

Example 10—Pharmacokinetics of IFN-γ in Primates

Figure 8:
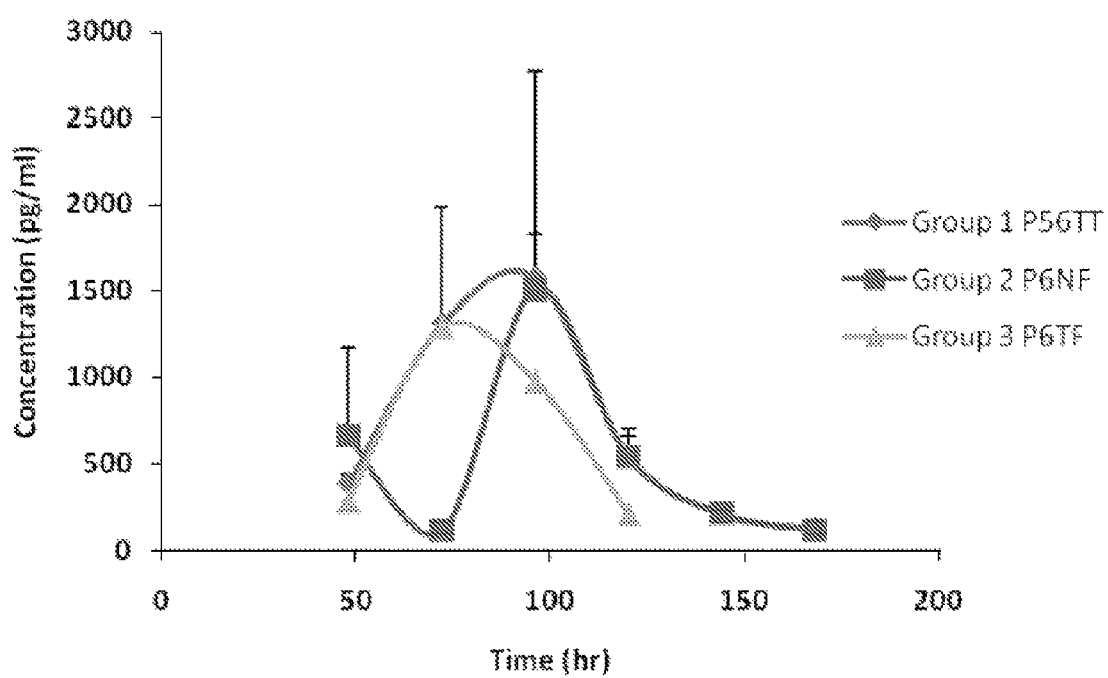
FIG. 8: Shows a graph of IFN-γ concentration in blood over time following injection of three different formulations of rHu-IL-12 into primates.

Blood samples from primates treated with rHu-IL-12 in different vehicles were analyzed for IFN-γ using ELISA, as described in Example 8. The final PK parameters (with the exception of Vd/F and CL/F which are undefined for endogenous, as opposed to administered, molecular species) for IFN-γ following SC administration of a dose of 1 μg/kg rHu-IL-12 are summarized in Table 11 below. The mean plasma concentration versus time data are presented graphically in FIG. 8. Cmax values are not statistically distinguishable among the three formulations, although Group 1 (P56TT) has the numerically highest value. Tmax is 96 hr for all three formulations; therefore the IFN-γ Cmax value is delayed some 94 hr past the IL-12 Cmax. $AUC_{0-t}$ is highest for the Group 1 formulation of rHu-IL-12, consistent with the numerically highest Cmax. This occurs in spite of the fact that $AUC_{0-t}$ for IL-12 is largest for Group 2.

TABLE 11

Summary of PK Parameters for IFN-γ

| ID | Cmax (pg/ml) | Tmax (hr) | AUC0 (pg * hr/ml) | Kel (1/hr) | AUC∞ (pg * hr/ml) |
|---|---|---|---|---|---|
| Group 1 P56TT | 1575.00 | 96.00 | 95596.43 | 0.04 | 98971.02 |
| Group 2 P6NF | 1506.00 | 96.00 | 92426.08 | 0.04 | 95608.38 |
| Group 3 P6TF | 1284.00 | 96.00 | 61694.78 | 0.04 | 67055.32 |

Example 11—Pharmacokinetics of EPO in Primates

Figure 9:
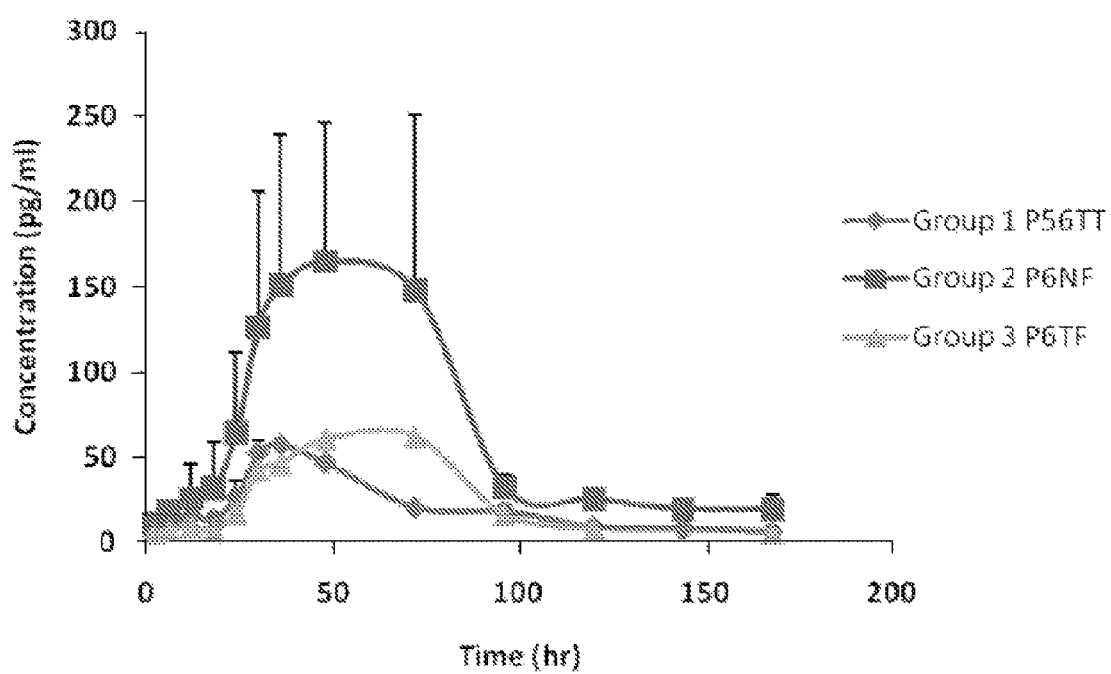
FIG. 9: Shows a graph of EPO concentration in blood over time following injection of three different formulations of rHu-IL-12 into primates.

Blood samples from primates treated with rHu-IL-12 in different vehicles were analyzed for EPO using ELISA, as described in Example 8. The final PK parameters for EPO following SC administration of a dose of 1 μg/kg rHU-IL-12 are summarized in Table 12 below. The mean plasma concentration versus time data are presented graphically in FIG. 9, and demonstrate a positive response to RHu-IL-12 administration. Cmax is highest in Group 2, consistent with the highest IL-12 Cmax for this group, by a factor of nearly 3×, although with this small an n the confidence interval for Group 2 overlaps the Cmax values for the other groups. The range for Tmax is 36-48 hr (based on groups which had n=2; there is a single animal estimate of 72 hr for Group 3 which is probably an outlier value), some 34-46 hr following the Tmax for IL-12 and 48-60 hr before Tmax for IFN-γ. The elimination rate constants were similar in all three groups. $AUC_{0-t}$ for Group 2 was nearly 3× that of either of the other two groups. This is consistent with a higher Cmax in that group, as well as the highest IL-12 AUC and Cmax in that group.

TABLE 12

Summary of PK Parameters for EPO

| ID | Cmax (pg/ml) | Tmax (hr) | AUC0 (pg * hr/ml) | Kel (1/hr) | AUC∞ (pg * hr/ml) |
|---|---|---|---|---|---|
| Group 1 P56TT | 572.30 | 36.00 | 34582.00 | 0.02 | 38018.30 |
| Group 2 P6NF | 1642.90 | 48.00 | 115238.30 | 0.02 | 124745.79 |
| Group 3 P6TF | 620.00 | 72.00 | 42409.60 | 0.03 | 44294.42 |

Example 12—Pharmacokinetics of IL-15 in Primates

Figure 10:
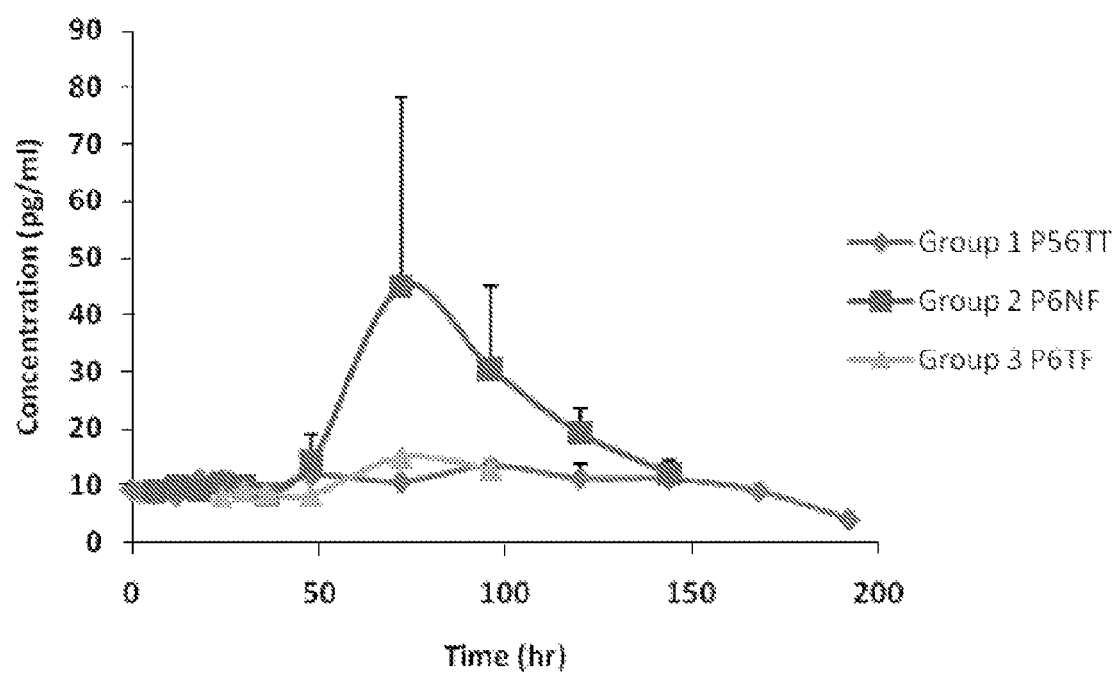
FIG. 10: Shows a graph of IL-15 concentration in blood over time following injection of three different formulations of rHu-IL-12 into primates.

Blood samples from primates treated with rHu-IL-12 in different vehicles were analyzed for IL-15 using ELISA, as described in Example 8. The final PK parameters for IL-15 following SC administration of a dose of 1 µg/kg rHu-IL-12 are summarized in Table 13 below. The mean plasma concentration versus time data are presented graphically in FIG. 10, and demonstrate a positive response to rHu-IL-12 administration. Cmax is highest in Group 2, consistent with the highest IL-12 Cmax for this group, by a factor of nearly 3×. The range for Tmax is 72-96-hr, at least 66 hr following the Tmax for IL-12 (2-6 hrs) but similar to the Tmax for IFN-γ (96 hrs). The elimination rate constants were similar where they could be estimated, but must be interpreted with caution. $AUC_{0-t}$ for Group 2 was much larger than that of either of the other two groups. This is consistent with a higher Cmax in that group, as well as the highest IL-12 AUC and Cmax in that group.

TABLE 13

Summary of PK Parameters for IL-15

| ID | Cmax (pg/ml) | Tmax (hr) | AUC0 (pg * hr/ml) | Kel (1/hr) | AUC∞ (pg * hr/ml) |
|---|---|---|---|---|---|
| Group 1 P56TT | 13.4 | 96 | 1983.006 | 0.011 | 2347.12 |
| Group 2 P6NF | 44.96 | 72 | 2998.605 | 0.018 | 3649.74 |
| Group 3 P6TF | 15 | 72 | 822.732 | NA | NA |

Example 13—Pharmacokinetics of IL-18 in Primates

Figure 11:
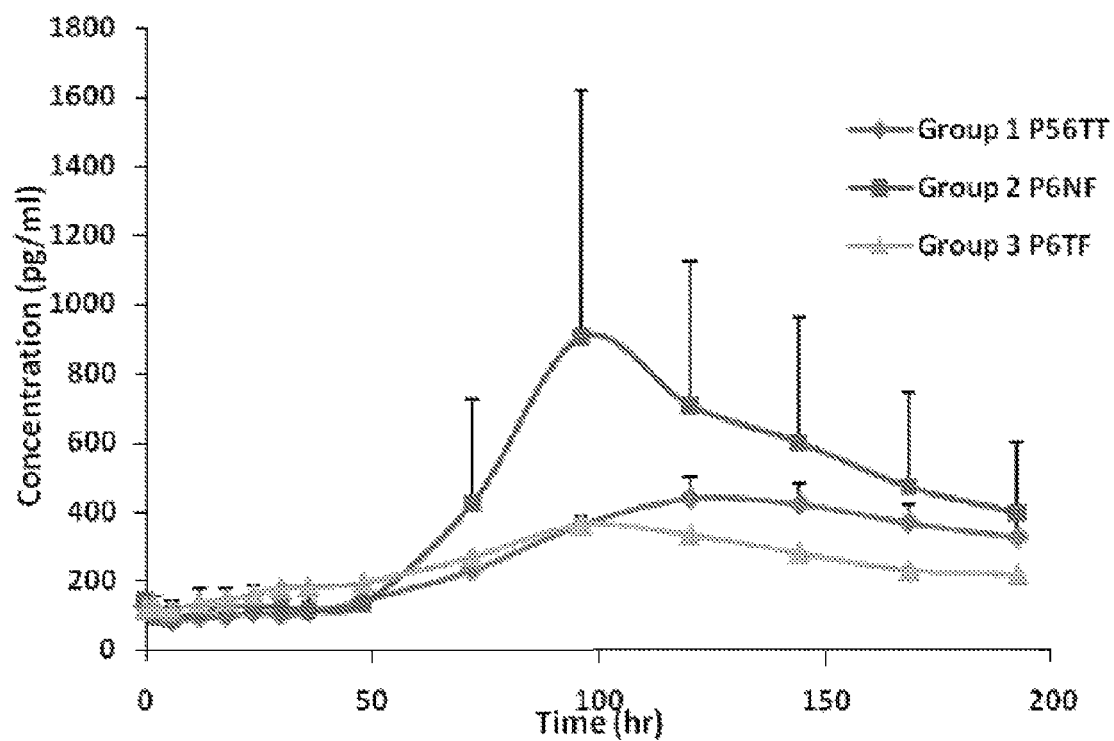
FIG. 11: Shows a graph of IL-18 concentration in blood over time following injection of three different formulations of rHu-IL-12 into primates.

Blood samples from primates treated with rHu-IL-12 in different vehicles were analyzed for IL-18 using ELISA, as described in Example 8. The final PK parameters for IL-18 following SC administration of a dose of 1 µg/kg rHu-IL-12 are summarized in Table 14 below. The mean plasma concentration versus time data are presented graphically in FIG. 11, and demonstrate a positive response to rHu-IL-12 administration. Cmax is highest in Group 2, consistent with the highest IL-12 Cmax for this group, by a factor of over 2×. The range for Tmax is 96-120-hr, at least 90 hr following the Tmax for IL-12 (2-6 hr) but similar to the Tmax for IFN-γ (96 hrs). The elimination rate constants were similar, but must be interpreted with caution. $AUC_{0-t}$ for Group 2 was much larger than that of either of the other two groups. This is consistent with a higher Cmax in that group, as well as the highest IL-12 AUC and Cmax in that group. $AUC_{0-inf}$ values are not reliable since they vary greatly compared to $AUC_{0-t}$, again because of an incomplete decay phase.

TABLE 14

Summary of PK Parameters for IL-15

| ID | Cmax (pg/ml) | Tmax (hr) | AUC0 (pg * hr/ml) | Kel (1/hr) | AUC∞ (pg * hr/ml) |
|---|---|---|---|---|---|
| Group 1 P56TT | 2996 | 120 | 429193.5 | 0.005 | 840252.2 |
| Group 2 P6NF | 3436 | 120 | 471918.8 | 0.01 | 638658.4 |
| Group 3 P6TF | 2919 | 96 | 494440.9 | 0.004 | 971402.3 |

Example 14—Pharmacokinetics of Neopterin in Primates

Figure 12:
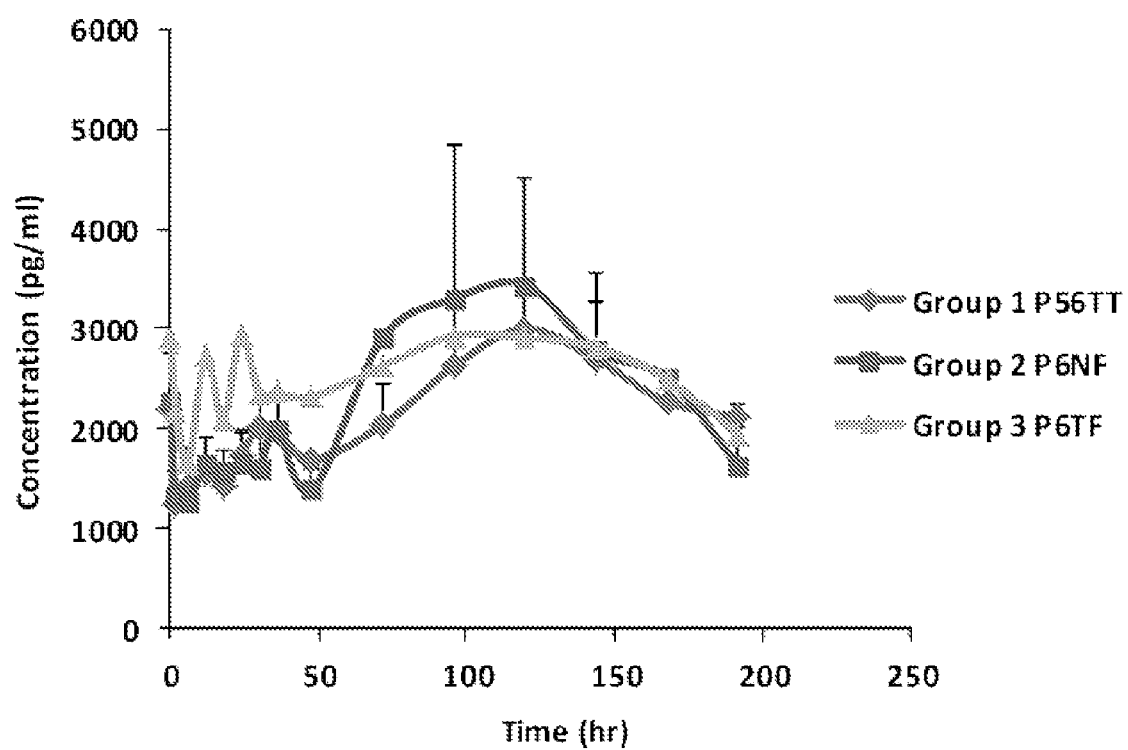
FIG. 12: Shows a graph of Neopterin concentration in blood over time following injection of three different formulations of rHu-IL-12 into primates.

Blood samples from primates treated with rHu-IL-12 in different vehicles were analyzed for Neopterin using ELISA, as described in Example 8. The final PK parameters for Neopterin following SC administration of a dose of 1 µg/kg rHu-IL-12 are summarized in Table 15 below. The mean plasma concentration versus time data are presented graphically in FIG. 12, and demonstrate a positive response to rHu-IL-12 administration. Cmax is highest in Group 2, consistent with the highest IL-12 Cmax for this group, by a factor of about 15%. The range for Tmax is 96-120-hr, at least 90 hr following the Tmax for IL-12 (2-6 hrs) but similar to the Tmax for IFN-γ (96 hrs). The elimination rate constants were similar, but must be interpreted with caution. AUC 0 for Group 2 was larger than that of Group 1, but about 5% smaller than that of Group 3. A high AUC is consistent with a high Cmax in Group 2 as well as the highest IL-12 AUC and Cmax in that group. $AUC_{0-inf}$ values are not reliable since they vary greatly compared to $AUC_{0-t}$, again because of an incomplete decay phase.

TABLE 15

Summary of PK Parameters for IL-15

| ID | Cmax (pg/ml) | Tmax (hr) | AUC0 (pg * hr/ml) | Kel (1/hr) | AUC∞ (pg * hr/ml) |
|---|---|---|---|---|---|
| Group 1 P56TT | 2996.000 | 120.000 | 429193.501 | 0.005 | 840252.244 |
| Group 2 P6NF | 3436.000 | 120.000 | 471918.750 | 0.010 | 638658.360 |
| Group 3 P6TF | 2919.000 | 96.000 | 494440.936 | 0.004 | 971402.259 |

Example 15—Summary Analysis of PK for Three Formulations

A single dose study was performed to determine the pharmacokinetics (PK) and pharmacodynamics (PD) of rHu-IL-12 following subcutaneous (SC) administration at a dose of 1 µg/kg in three different formulations to non-irradiated rhesus monkeys. The biomarkers studied were IL-12, EPO, IFN-γ, IL-15, IL-18 and neopterin. Many PK parameters were similar across formulations within a given biomarker. The volumes of distribution for IL-12 were suggestive of a low bioavailability (F) and/or a large distribution into extravascular spaces.

IFN-γ, EPO. IL-15, IL-18 and neopterin were characterized with plasma concentration versus time curves that showed a positive response to rHu-IL-12 administration. In all cases, these positive responses were delayed in time after rHu-IL-12 was dosed.

Cmax and AUC for IL-12 were generally highest for the Group 2 P6NF formulation. This formulation also gave the numerically highest Cmax and AUC values for EPO, IL-15, and IL-18. The Group 3 P6TF AUC was slightly higher than the Group 2 P6NF formulation for Neopterin. For IFN-γ the Group 1 P56TT formulation produced the numerically highest Cmax and AUC values. But it must be emphasized that group sizes were very small and this last observation might not hold with larger group sizes.

If IL-12 blood level is the most important target variable the P6NF formulation appears to give the highest Cmax and AUC. But if IFN-γ is the main therapeutic effector for IL-12 it is possible that the P56TT formulation may be superior. But even so, this formulation only gives about a 3.5% elevation in AUC over that seen with P6NF. On balance the P6NF formulation is the best choice for future studies. However, it is important to emphasize that the small group size created large standard errors and confidence intervals.

In addition, it is clear that for several cytokines the decay phase was incomplete. These factors together indicate that calculated PK parameters such as elimination rate constants and AUC must be considered estimates.

Unless otherwise defined, all technical and scientific terms used herein have the same meaning as commonly understood by one of ordinary skill in the art to which this invention belongs.

The inventions illustratively described herein may suitably be practiced in the absence of any element or elements, limitation or limitations, not specifically disclosed herein. Thus, for example, the terms "comprising," "including," "containing," etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed.

Thus, it should be understood that although the present invention has been specifically disclosed by preferred embodiments and optional features, modification, improvement and variation of the inventions embodied therein herein disclosed may be resorted to by those skilled in the art, and that such modifications, improvements and variations are considered to be within the scope of this invention. The materials, methods, and examples provided here are representative of preferred embodiments, are exemplary, and are not intended as limitations on the scope of the invention.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

All publications, patent applications, patents, and other references mentioned herein are expressly incorporated by reference in their entirety, including all formulas and figures, to the same extent as if each were incorporated by reference individually. In case of conflict, the present specification, including definitions, will control.

Other embodiments are set forth within the following claims.

I claim:

1. A pharmaceutical interleukin-12 (IL-12) composition consisting essentially of:
    (a) about 15 pg/ml to about 30 pg/ml human IL-12;
    (b) about [50 mM to about 300 mM of at least one stabilizer; wherein the at least one stabilizer is] 150 mM sodium chloride;
    (c) about 0.01% to about 0.2% (weight/volume) of at least one surfactant, wherein the at least one surfactant is poloxamer-188; and
    (d) water,
    wherein the IL-12 is solubilized and the composition has a pH of about 4.5 to about 7.5; wherein the composition does not comprise trehalose;
    wherein in a cell-based assay the composition has a pharmaceutically acceptable EC50 value for IL-12-induced expression of interferon gamma (IFN-gamma), which is the effective concentration at which 50% of the cells respond by producing IFN-gamma; and
    wherein the composition is stable for at least 4 weeks of storage at 25° C.

2. The composition of claim 1, wherein the pH is selected from the group consisting of about 5.0 to about 7.0, about 5.5 to about 6.5, and about 6.0.

3. The composition of claim 1, wherein the composition comprises:
    (a) about 150 mM sodium chloride; and
    (b) about 0.1% poloxamer 188,
    wherein the composition has a pH of at least 5.5 and less than 6.5.

4. The composition of claim 1, wherein the composition further comprises a phosphate buffer in an amount of from about 1 mM to about 100 mM.

5. A kit comprising one or more doses of the composition of claim 1.

6. The kit of claim 5, wherein the composition is present in an aqueous form for injection.

7. The kit of claim 5, wherein the composition is useful for increasing survival in a subject, and/or preserving bone marrow function, and/or promoting hematopoietic recovery or restoration following non-therapeutic acute exposure to whole body ionizing radiation to the subject.

8. The kit of claim 5, wherein the composition is useful for treating a hematopoietic toxicity associated with a cancer therapy.

* * * * *

UNITED STATES PATENT AND TRADEMARK OFFICE
CERTIFICATE OF CORRECTION

PATENT NO. : 9,878,012 B2
APPLICATION NO. : 13/697940
DATED : January 30, 2018
INVENTOR(S) : Lena A. Basile Page 1 of 1

It is certified that error appears in the above-identified patent and that said Letters Patent is hereby corrected as shown below:

In the Claims

In Column 52, Line 6, Claim 1:
"(a) about 15 pg/ml to about 30 pg/ml human IL-12;"
Should read:
-- (a) about 15 micrograms/ml to about 30 micrograms/ml human IL-12; --

In Column 52, Lines 7-9, Claim 1:
"(b) about [50 mM to about 300 mM of at least one stabilizer; wherein the at least one stabilizer is] 150 mM sodium chloride;"
Should read:
-- (b) about 150 mM sodium chloride; --

Signed and Sealed this
Eighteenth Day of June, 2019

Andrei Iancu
*Director of the United States Patent and Trademark Office*